(12) United States Patent
Choi et al.

(10) Patent No.: US 9,842,998 B2
(45) Date of Patent: *Dec. 12, 2017

(54) COMPOUND, AND LIGHT EMITTING DIODE AND ELECTRONIC APPARATUS COMPRISING SAME

(71) Applicant: LMS Co., Ltd., Pyeongtaek-si (KR)

(72) Inventors: Jeong Og Choi, Seoul (KR); Joon Ho Jung, Hwaseong-si (KR); Oh Kwan Kwon, Anyang-si (KR)

(73) Assignee: LMS CO., LTD., Pyeongtaek-si (KR)

( * ) Notice: Subject to any disclaimer, the term of this patent is extended or adjusted under 35 U.S.C. 154(b) by 305 days.

This patent is subject to a terminal disclaimer.

(21) Appl. No.: 14/429,994

(22) PCT Filed: Sep. 18, 2013

(86) PCT No.: PCT/KR2013/008465
§ 371 (c)(1),
(2) Date: Jun. 26, 2015

(87) PCT Pub. No.: WO2014/046494
PCT Pub. Date: Mar. 27, 2014

(65) Prior Publication Data
US 2016/0072074 A1    Mar. 10, 2016

(30) Foreign Application Priority Data

Sep. 21, 2012 (KR) .................. 10-2012-0105153
Feb. 21, 2013 (KR) .................. 10-2013-0018534

(51) Int. Cl.
*H01L 51/50* (2006.01)
*H01L 51/00* (2006.01)
(Continued)

(52) U.S. Cl.
CPC ........ *H01L 51/0072* (2013.01); *C07D 405/14* (2013.01); *C07D 409/14* (2013.01);
(Continued)

(58) Field of Classification Search
CPC .. C07D 409/14; C07D 405/14; C09K 11/025; C09K 11/06; H01L 51/006;
(Continued)

(56) References Cited

U.S. PATENT DOCUMENTS

2009/0096360 A1* 4/2009 Tanaka .................. C09K 11/06
                                                313/504
2009/0134784 A1* 5/2009 Lin ...................... C07D 209/88
                                                313/504
(Continued)

FOREIGN PATENT DOCUMENTS

JP    2008-294161 A    12/2008
JP    2012-049518 A    3/2012
(Continued)

OTHER PUBLICATIONS

Kathryn C. Moss et al., "Tuning the Intramolecular Charge Transfer Emission from Deep Blue to Green in Ambipolar Systems Based on Dibenzothiophene S,S-Dioxide by Manipulation of Conjugation and Strength of the Electron Donor Units," J. Org. Chem., 2010, vol. 75 pp. 6771-6781.
(Continued)

*Primary Examiner* — Gregory Clark
*Assistant Examiner* — Sean M Deguire
(74) *Attorney, Agent, or Firm* — Polsinelli PC

(57) ABSTRACT

In a novel compound, and a light emitting diode and an electronic apparatus including the same, the novel compound is represented by the following Chemical Formula 1.
(Continued)

[Chemical Formula 1]

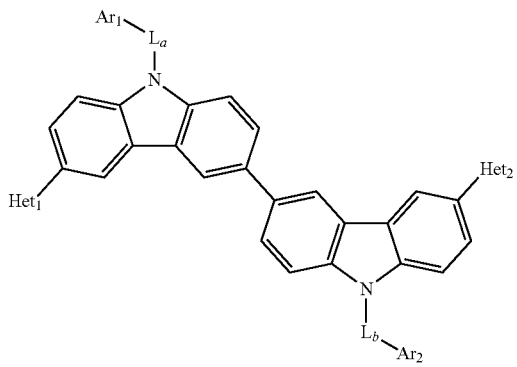

12 Claims, 2 Drawing Sheets

(51) Int. Cl.
C09K 11/06 (2006.01)
C09K 11/02 (2006.01)
C07D 405/14 (2006.01)
C07D 409/14 (2006.01)
C07F 7/08 (2006.01)

(52) U.S. Cl.
CPC .......... *C07F 7/0816* (2013.01); *C09K 11/025* (2013.01); *C09K 11/06* (2013.01); *H01L 51/0052* (2013.01); *H01L 51/0058* (2013.01); *H01L 51/0061* (2013.01); *H01L 51/0073* (2013.01); *H01L 51/0074* (2013.01); *H01L 51/0094* (2013.01); *H01L 51/006* (2013.01); *H01L 51/506* (2013.01); *H01L 51/5056* (2013.01); *H01L 51/5064* (2013.01); *H01L 51/5096* (2013.01)

(58) Field of Classification Search
CPC ............. H01L 51/0072; H01L 51/0073; H01L 51/0074; H01L 51/5056; H01L 51/506; H01L 51/5064; H01L 51/5096
See application file for complete search history.

(56) References Cited

U.S. PATENT DOCUMENTS

2011/0278552 A1  11/2011  Numata et al.
2016/0043326 A1* 2/2016  Choi ................... H01L 51/0072
                                                               257/40

FOREIGN PATENT DOCUMENTS

JP    2012-175025 A    9/2012
KR    2008-0104025 A   11/2008
WO    2012/008281 A1   1/2012

OTHER PUBLICATIONS

Lidan Deng et al., "Molecular designing and DFT investigation of novel alternating donor-acceptor dibenzo[b, d] thiophen-based systems: from monomer to polymer," Struct. Chem., 2012 vol. 23, pp. 97-106 (Published online Aug. 5, 2011).

* cited by examiner

[Fig.1]
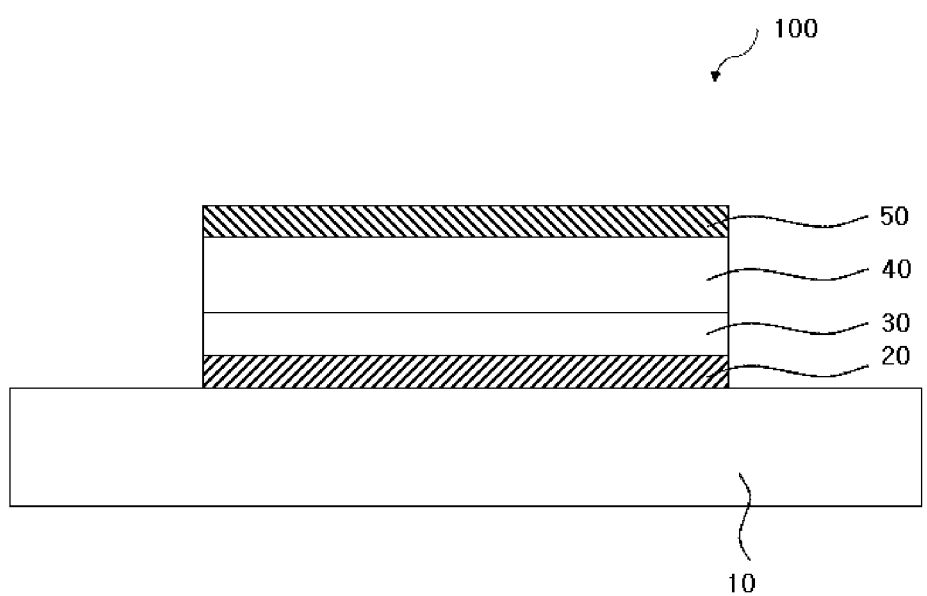

[Fig.2]
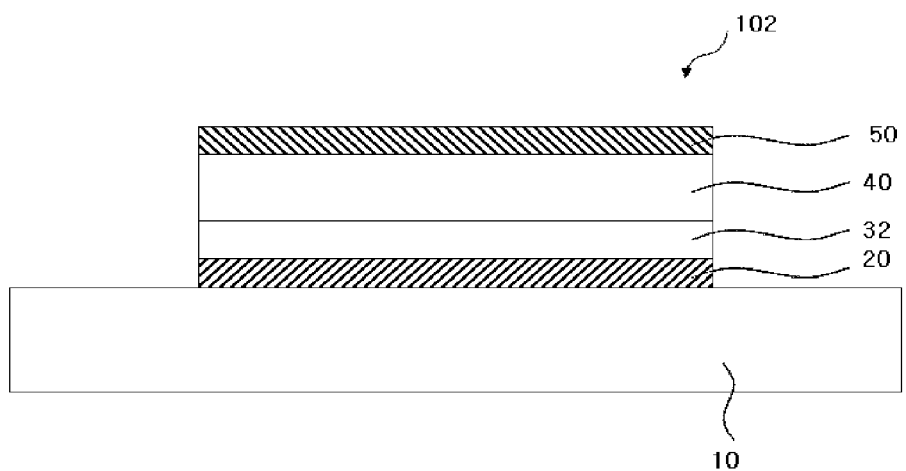
[Fig.3]
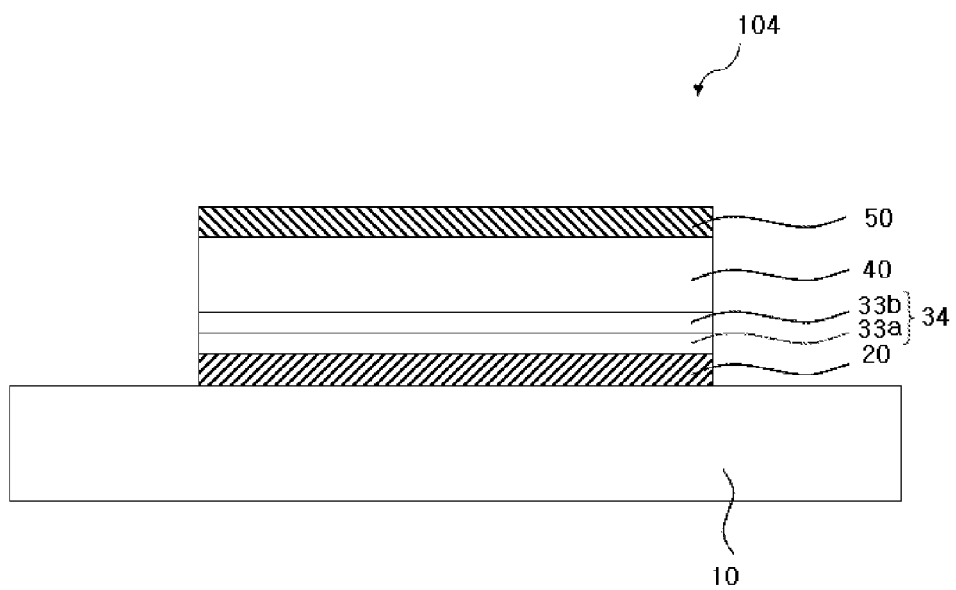

COMPOUND, AND LIGHT EMITTING DIODE AND ELECTRONIC APPARATUS COMPRISING SAME

CROSS-REFERENCE TO RELATED APPLICATIONS

This application is the U.S. national phase of International Application No. PCT/KR2013/008465 filed Sep. 18, 2013, and claims priority to Korean Patent Application Nos. 10-2012-0105153 and 10-2013-0018534 filed Sep. 21, 2012 and Feb. 21, 2013, respectively, the disclosures of which are hereby incorporated in their entirety by reference.

BACKGROUND

Field of the Invention

The present invention relates to a novel compound, and a light emitting diode and an electronic apparatus including the same, and more particularly, to a compound for an organic light emitting diode, and a light emitting diode and an electronic apparatus including the same.

Background Art

Generally, a light emitting diode includes two electrodes facing each other, and a light emitting layer including a light emitting compound interposed between the electrodes. If a current flows between the electrodes, the light emitting compound generates light. In a display device using the light emitting diode, since a separate light source device is not required, a weight, a size, or a thickness of the display device may be reduced. Further, the display device using the light emitting diode has merits in view of excellent viewing angle, contrast ratio, color reproducibility, or the like and low consumption power as compared to a display device using a backlight and a liquid crystal.

The light emitting diode may further include a hole transport layer disposed between an anode and the light emitting layer. The hole transport layer may stabilize an interface between the anode and the light emitting layer and minimize an energy barrier therebetween.

However, the light emitting diode still has problems in that a light emitting life-span is short and power efficiency is low. In order to solve the aforementioned problems, various compounds have been developed as a material of the light emitting diode, but there is a limitation in manufacturing the light emitting diode satisfying all aspects in view of the light emitting life-span, power efficiency, and thermal stability.

SUMMARY OF THE INVENTION

Technical Problem

Therefore, the present invention has been made in an effort to provide a novel compound for improving hole injection and transport abilities of a light emitting diode.

Further, the present invention has been made in an effort to provide a light emitting diode including the compound.

Further, the present invention has been made in an effort to provide an electronic apparatus including the light emitting diode.

Technical Solution

An exemplary embodiment of the present invention provides a compound represented by the following Chemical Formula 1.

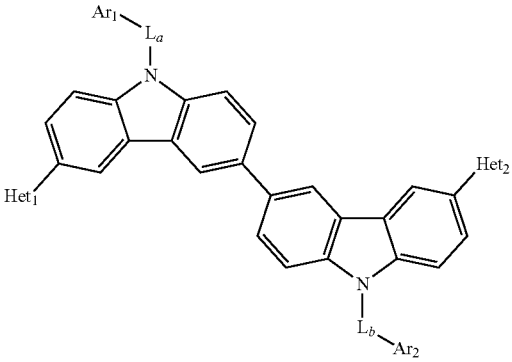

[Chemical Formula 1]

In the Chemical Formula, $L_a$ and $L_b$ each independently represents *-$L_1$-$L_2$-$L_3$-$L_4$-*, $L_1$, $L_2$, $L_3$ and $L_4$ each independently represent a single bond, —O—, —S—, an arylene group having 6 to 20 carbon atoms, a heteroarylene group having 2 to 20 carbon atoms, or a cycloalkylene group having 3 to 20 carbon atoms, $Ar_1$ and $Ar_2$ each independently represent hydrogen, an alkyl group having 1 to 6 carbon atoms, an aryl group having 6 to 20 carbon atoms, a heteroaryl group having 2 to 20 carbon atoms, a cycloalkyl group having 3 to 20 carbon atoms, a heterocycloalkyl group having 2 to 20 carbon atoms, a bicycloalkyl group having 5 to 20 carbon atoms, the following Chemical Formula 2-1, or the following Chemical Formula 2-2.

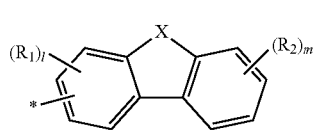

[Chemical Formula 2-1]

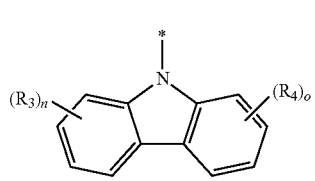

[Chemical Formula 2-2]

$Het_1$ and $Het_2$ each independently represent the following Chemical Formula 3 or the following Chemical Formula 4.

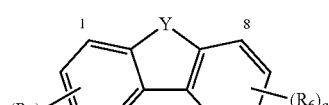

[Chemical Formula 3]

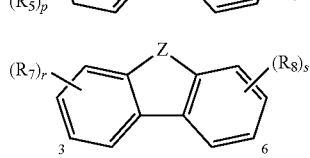

[Chemical Formula 4]

Herein, X represents N—W, O, S, or $Si(R_9)(R_{10})$,

W represents hydrogen, an alkyl group having 1 to 6 carbon atoms, an aryl group having 6 to 20 carbon atoms, a heteroaryl group having 2 to 20 carbon atoms, a cycloalkyl group having 3 to 20 carbon atoms, a heterocycloalkyl group having 2 to 20 carbon atoms, or a bicycloalkyl group having 5 to 20 carbon atoms, Y represents S or O, Z represents S, $R_1$, $R_2$, $R_3$, $R_4$, $R_5$, $R_6$, $R_7$, $R_8$, $R_9$, and $R_{10}$ each independently represent an alkyl group having 1 to 6 carbon atoms, an aryl group having 6 to 20 carbon atoms, or a heteroaryl group having 2 to 20 carbon atoms, l represents an integer of 0 to 3, m, n, and o each independently represent an integer of 0 to 4, any one of p and q represents an integer of 0 to 3 and the other represents an integer of 0 to 4, any one of r and s represents an integer of 0 to 3 and the other represents an integer of 0 to 4, a substituent group represented by Chemical Formula 3 is substituted by the compound of Chemical Formula 1 at carbon position No. 1 or 8, a substituent group represented by Chemical Formula 4 is substituted by the compound of Chemical Formula 1 at carbon position No. 3 or 6, and in the aforementioned definitions of substituents in Chemical Formulas 1 to 4, the alkyl group, the aryl group, the heteroaryl group, the cycloalkyl group, the heterocycloalkyl group, and the bicycloalkyl group are each independently unsubstituted or substituted by one or more substituent groups selected from the group consisting of an alkyl group having 1 to 6 carbon atoms, an alkoxy group having 1 to 6 carbon atoms, an amine group unsubstituted or substituted by one or more alkyl groups having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

In the exemplary embodiment, the compound of Chemical Formula 1 may be represented by the following Chemical Formula 5.

[Chemical Formula 5]

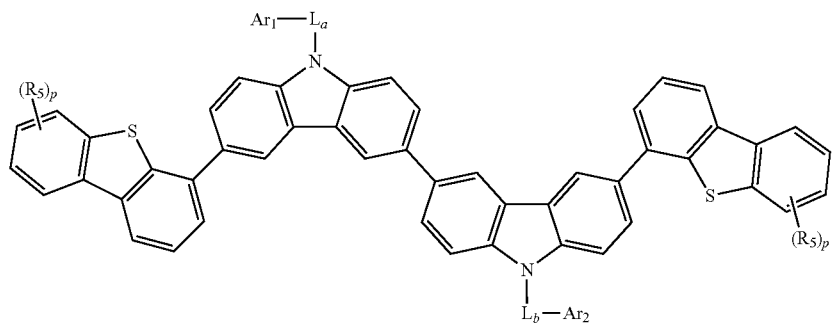

In the Chemical Formula, $Ar_1$, $Ar_2$, $L_a$, $L_b$, $R_5$, and p are the same as those defined in claim 1, $Ar_1$ and $Ar_2$ are the same as each other, and $L_a$ and $L_b$ are the same as each other.

In another exemplary embodiment, the compound of Chemical Formula 1 may be represented by the following Chemical Formula 6.

[Chemical Formula 6]

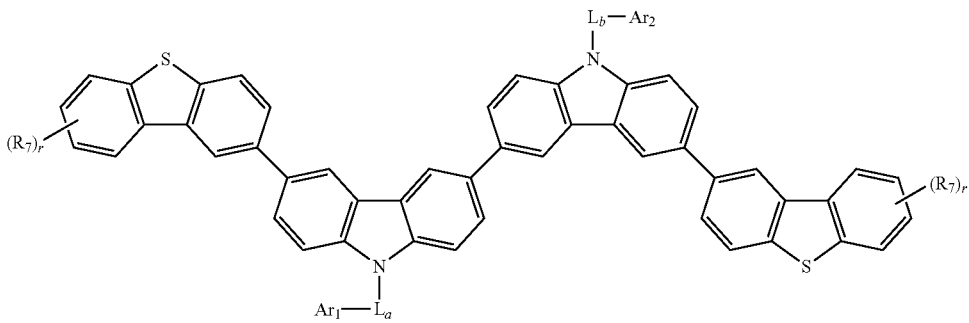

In the Chemical Formula, $Ar_1$, $Ar_2$, $L_a$, $L_b$, $R_7$, and r are the same as those defined in claim 1, $Ar_1$ and $Ar_2$ are the same as each other, and $L_a$ and $L_b$ are the same as each other.

In yet another exemplary embodiment, the compound of Chemical Formula 1 may be represented by the following Chemical Formula 7.

[Chemical Formula 7]

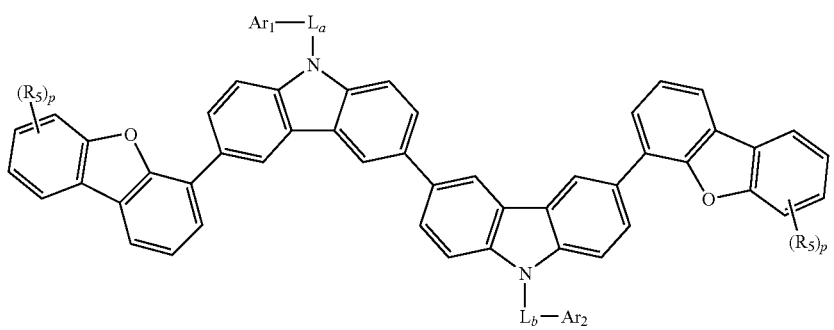

In the Chemical Formula,

Ar$_1$, Ar$_2$, L$_a$, L$_b$, R$_5$, and p are the same as those defined in claims 1, Ar$_1$ and Ar$_2$ are the same as each other, and L$_a$ and L$_b$ are the same as each other.

Another exemplary embodiment of the present invention provides a light emitting diode including a first electrode, a second electrode, a light emitting layer, and a hole transportable layer including the compound represented by Chemical Formula 1. The first electrode and the second electrode may face each other, the light emitting layer may be interposed between the first and second electrodes, and the hole transportable layer may be disposed between the first electrode and the light emitting layer.

In the exemplary embodiment, the hole transportable layer may include a first layer including the compound and a P-type dopant, and a second layer including the compound. For example, the first layer may be disposed between the first electrode and the light emitting layer, and the second layer may be disposed between the first layer and the light emitting layer. In this case, the second layer may further include a dopant of a kind that is substantially the same as or different from the P-type dopant of the first layer.

Yet another exemplary embodiment of the present invention provides an electronic apparatus including a hole transportable layer including the compound represented by Chemical Formula 1.

Effect of the Invention

According to the aforementioned novel compound, and the light emitting diode and the electronic apparatus including the same, the novel compound of the present invention may improve hole injection and/or transport abilities of the light emitting diode.

Further, it is possible to improve light emitting efficiency of the light emitting diode and increase a life-span of the light emitting diode by using the compound. Further, it is possible to improve thermal stability (heat resistance) of the light emitting diode.

BRIEF DESCRIPTION OF DRAWINGS

FIG. 1 is a cross-sectional view for illustrating a light emitting diode according to an exemplary embodiment of the present invention.

FIG. 2 is a cross-sectional view for illustrating a light emitting diode according to another exemplary embodiment of the present invention.

FIG. 3 is a cross-sectional view for illustrating a light emitting diode according to yet another exemplary embodiment of the present invention.

DETAILED DESCRIPTION OF THE INVENTION

Hereinafter, a novel compound according to the present invention will be first described, and a light emitting diode including the compound will be described in more detail with reference to the accompanying drawings.

The compound according to the present invention is represented by the following Chemical Formula 1.

[Chemical Formula 1]

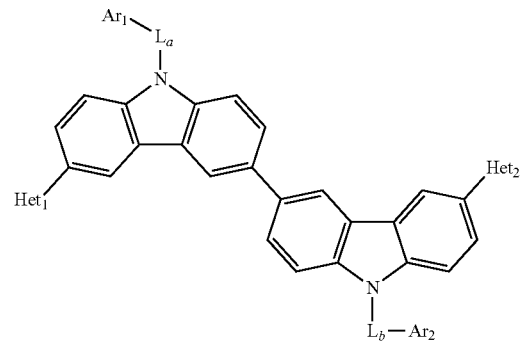

In the Chemical Formula,

L$_a$ and L$_b$ each independently represents *-L$_1$-L$_2$-L$_3$-L$_4$-*,

L$_1$, L$_2$, L$_3$ and L$_4$ each independently represent a single bond, —O—, —S—, an arylene group having 6 to 20 carbon atoms, a heteroarylene group having 2 to 20 carbon atoms, or a cycloalkylene group having 3 to 20 carbon atoms, Ar$_1$ and Ar$_2$ each independently represent hydrogen, an alkyl group having 1 to 6 carbon atoms, an aryl group having 6 to 20 carbon atoms, a heteroaryl group having 2 to 20 carbon atoms, a cycloalkyl group having 3 to 20 carbon atoms, a heterocycloalkyl group having 2 to 20 carbon atoms, a bicycloalkyl group having 5 to 20 carbon atoms, the following Chemical Formula 2-1, or the following Chemical Formula 2-2.

[Chemical Formula 2-1]

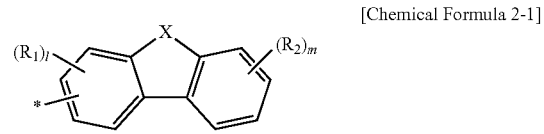

-continued

[Chemical Formula 2-2]

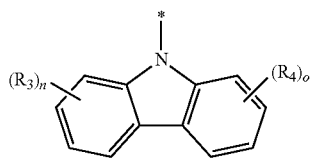

Het$_1$ and Het$_2$ each independently represent the following Chemical Formula 3 or the following Chemical Formula 4.

[Chemical Formula 3]

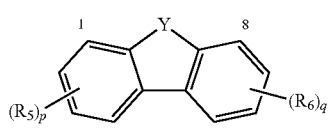

[Chemical Formula 4]

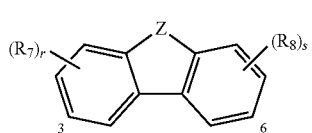

Herein, X represents N—W, O, S, or Si(R$_9$)(R$_{10}$),

W represents hydrogen, an alkyl group having 1 to 6 carbon atoms, an aryl group having 6 to 20 carbon atoms, a heteroaryl group having 2 to 20 carbon atoms, a cycloalkyl group having 3 to 20 carbon atoms, a heterocycloalkyl group having 2 to 20 carbon atoms, or a bicycloalkyl group having 5 to 20 carbon atoms, Y represents S or O, Z represents S, R$_1$, R$_2$, R$_3$, R$_4$, R$_5$, R$_6$, R$_7$, R$_8$, R$_9$, and R$_{10}$ each independently represent an alkyl group having 1 to 6 carbon atoms, an aryl group having 6 to 20 carbon atoms, or a heteroaryl group having 2 to 20 carbon atoms, l represents an integer of 0 to 3, m, n, and o each independently represent an integer of 0 to 4, any one of p and q represents an integer of 0 to 3 and the other represents an integer of 0 to 4, any one of r and s represents an integer of 0 to 3 and the other represents an integer of 0 to 4, a substituent group represented by Chemical Formula 3 is substituted by the compound of Chemical Formula 1 at carbon position 1 or 8, a substituent group represented by Chemical Formula 4 is substituted by the compound of Chemical Formula 1 at carbon position 3 or 6, and in the aforementioned definitions of substituents in Chemical Formulas 1 to 4, the alkyl group, the aryl group, the heteroaryl group, the cycloalkyl group, the heterocycloalkyl group, and the bicycloalkyl group are each independently unsubstituted or substituted by one or more substituent groups selected from the group consisting of an alkyl group having 1 to 6 carbon atoms, an alkoxy group having 1 to 6 carbon atoms, an amine group unsubstituted or substituted by one or more alkyl groups having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

In the present invention, the "aryl group" is defined by a monovalent substituent group derived from aromatic hydrocarbon.

Specific examples of the aryl group may include a phenyl group, a naphthyl group, an anthracenyl group, a naphthacenyl group, a pyrenyl group, a tolyl group, a biphenyl group, a terphenyl group, a chrycenyl group, a spirobifluorenyl group, a fluoranthenyl group, a fluorenyl group, a perylenyl group, an indenyl group, an azulenyl group, a heptalenyl group, a phenalenyl group, a phenanthrenyl group, and the like.

The aryl group has 6 to 20 carbon atoms, for example, 6 to 18 carbon atoms, or 6 to 12 carbon atoms.

The "heteroaryl group" represents an "aromatic heterocycle" derived from a monocycle or a condensed cycle. The heteroaryl group may include at least one, for example, one, two, three, or four of nitrogen (N), sulfur (S), oxygen (O), phosphorus (P), selenium (Se), and silicon (Si) as heteroatoms.

Specific examples of the heteroaryl group may include a nitrogen-containing heteroaryl group including a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolinyl group, a quinolizinyl group, a phthalazinyl group, a naphthylidinyl group, a quinoxalinyl group, a quinazolinyl group, a cinnolinyl group, a pteridinyl group, an imidazotriazinyl group, an acridinyl group, a phenanthridinyl group, a carbazolyl group, a phenanthrolinyl group, a phenazinyl group, an imidazopyridinyl group, an imidazopyrimidinyl group, a pyrazolopyridinyl group, and the like; a sulfur-containing heteroaryl group including a thienyl group, a benzothienyl group, a dibenzothienyl group, and the like; and an oxygen-containing heteroaryl group including a furyl group, a pyranyl group, a cyclopentapyranyl group, a benzofuranyl group, an isobenzofuranyl group, a dibenzofuranyl group, and the like. Further, specific examples of the heteroaryl group may include compounds including at least two heteroatoms, such as a thiazolyl group, an isothiazolyl group, a benzothiazolyl group, a benzothiadiazolyl group, a phenothiazinyl group, an isoxazolyl group, a furazanyl group, a phenoxazinyl group, an oxazolyl group, a benzoxazolyl group, an oxadiazolyl group, a pyrazoloxazolyl group, an imidazothiazolyl group, a thienofuranyl group, and the like.

The heteroaryl group may have 2 to 20 carbon atoms, for example, 3 to 19 carbon atoms, 4 to 15 carbon atoms, or 5 to 11 carbon atoms. For example, if the heteroaryl group includes a heteroatom, the heteroaryl group may have 5 to 21 ring members.

The "alkyl group" is defined by a functional group derived from linear or branched saturated hydrocarbons.

Specific examples of the alkyl group may include a methyl group, an ethyl group, a n-propyl group, an isopropyl group, a n-butyl group, a sec-butyl group, a t-butyl group, a n-pentyl group, a 1,1-dimethylpropyl group, a 1,2-dimethylpropyl group, a 2,2-dimethylpropyl group, a 1-ethylpropyl group, a 2-ethylpropyl group, a n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

The alkyl group has 1 to 20 carbon atoms, for example, 1 to 12 carbon atoms, 1 to 6 carbon atoms, or 1 to 4 carbon atoms.

The "cycloalkyl group" is defined as a functional group derived from monocyclic saturated hydrocarbon.

Specific examples of the cycloalkyl group may include a cyclopropyl group, a cyclobutyl group, a cyclopentyl group, a cyclohexyl group, a cycloheptyl group, a cyclooctyl group, or the like.

The cycloalkyl group has 3 to 20 carbon atoms, for example, 3 to 12 carbon atoms or 3 to 6 carbon atoms.

The "heterocycloalkyl group" is defined as a non-aromatic monocyclic or polycyclic group containing one kind or more heteroatoms as an element of a cycle in addition to the carbon atoms. The heteroatom may include oxygen (O), nitrogen (N), sulfur (S), selenium (Se), or phosphorus (P) atoms, and is not limited thereto. Further, even though the heterocycloalkyl group does not include an aromatic cycle, a bond connecting carbon atoms-carbon atoms or carbon atoms-heteroatoms constituting the cycle of the heterocycloalkyl group may include a double bond.

Specific examples of the heterocycloalkyl group include a 2-pyrrolidinyl group, a 3-pyrrolidinyl group, a piperidinyl group, a 2-tetrahydrofuranyl group, a 3-tetrahydrofuranyl group, a 2-tetrahydrothienyl group, and a 3-tetrahydrothienyl group, but are not limited thereto.

The heterocycloalkyl group has 2 to 20 carbon atoms, for example, 3 to 19 carbon atoms or 5 to 11 carbon atoms. That is, if the heterocycloalkyl group includes a heteroatom, the heterocycloalkyl group has 3 to 21 ring members, for example, 4 to 20 ring members or 6 to 12 ring members.

The "bicycloalkyl group" means a functional group having a structure where at least one carbon atom selected from each of two alkyl cycles is connected to each other.

Specific examples of the bicycloalkyl group may include a bicyclopentyl group, a bicyclohexyl group, a bicycloheptyl group, a bicyclootyl group, a bicyclononyl group, a bicyclodecyl group, or the like.

The bicycloalkyl group has 5 to 20 carbon atoms, for example, 7 to 18 carbon atoms or 7 to 12 carbon atoms.

Further, the "arylene group" may mean a divalent substituent group derived from the aforementioned aryl group.

Further, the "heteroarylene group" may mean a divalent substituent group derived from the aforementioned heteroaryl group.

In the present invention, in heteroaryl having three cycles, a position of the carbon atom that may substitute or be substituted is represented as in the following Chemical Formula based on the heteroatom, and hereinafter, a description will be given based on this.

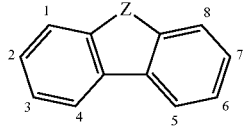

In the aforementioned Chemical Formula, Z represents X of Chemical Formula 2-1, Y of Chemical Formula 3, or Z of Chemical Formula 4.

The abbreviation "Cz" as will be used below represents carbazole, "DBT" represents dibenzothiophene, and "DBF" represents dibenzofuran.

In an exemplary embodiment of Chemical Formula 1, $L_a$ and $L_b$ each independently represents *-$L_1$-$L_2$-$L_3$-$L_4$-*, $L_1$, $L_2$, $L_3$, and $L_4$ each independently represent a single bond or an arylene group having 6 to 20 carbon atoms, $Ar_1$ and $Ar_2$ each independently represent an aryl group having 6 to 20 carbon atoms, a heteroaryl group having 2 to 20 carbon atoms, the following Chemical Formula 2-1, or the following Chemical Formula 2-2.

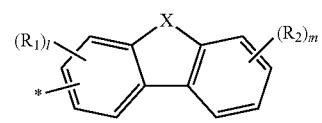

[Chemical Formula 2-1]

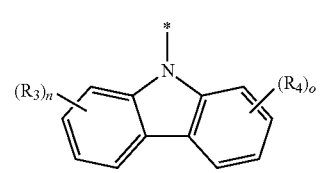

[Chemical Formula 2-2]

$Het_1$ and $Het_2$ each independently represent the following Chemical Formula 3 or the following Chemical Formula 4.

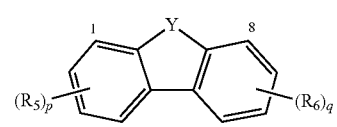

[Chemical Formula 3]

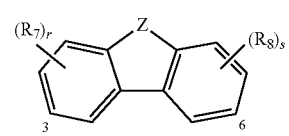

[Chemical Formula 4]

Herein, X represents N—W, O, S, or $Si(R_9)(R_{10})$,

W represents an aryl group having 6 to 20 carbon atoms or a heteroaryl group having 2 to 20 carbon atoms, Y represents S or O, Z represents S, $R_1$, $R_2$, $R_3$, $R_4$, $R_5$, $R_6$, $R_7$, $R_8$, $R_9$, and $R_{10}$ each independently represent an alkyl group having 1 to 6 carbon atoms or an aryl group having 6 to 20 carbon atoms, and m, n, l, o, p, q, r, and s may each independently represent an integer of 0 to 2.

In another exemplary embodiment of Chemical Formula 1, $L_a$ and $L_b$ each independently represent a single bond or an arylene group having 6 to 20 carbon atoms, $Ar_1$ and $Ar_2$ each independently represent an aryl group having 6 to 20 carbon atoms unsubstituted or substituted by an alkyl group having 1 to 6 carbon atoms or an aryl group having 6 to 20 carbon atoms; a heteroaryl group having 2 to 20 carbon atoms unsubstituted or substituted by an alkyl group having 1 to 6 carbon atoms or an aryl group having 6 to 20 carbon atoms; the following Chemical Formula 2-1, or the following Chemical Formula 2-2.

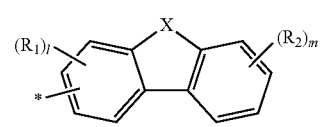

[Chemical Formula 2-1]

[Chemical Formula 2-2]

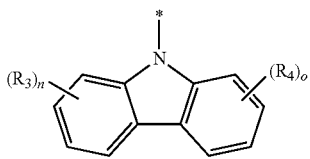

Het₁ and Het₂ each independently represent the following Chemical Formula 3 or the following Chemical Formula 4.

[Chemical Formula 3]

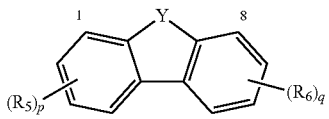

[Chemical Formula 4]

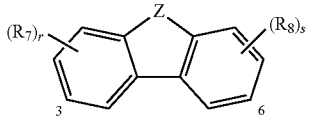

Herein, X represents O, S, or $Si(R_9)(R_{10})$,

Y represents S or O,

Z represents S, $R_1$, $R_2$, $R_3$, $R_4$, $R_5$, $R_6$, $R_7$, $R_8$, $R_9$, and $R_{10}$ each independently represent an alkyl group having 1 to 6 carbon atoms or an aryl group having 6 to 20 carbon atoms, and m, n, l, o, p, and q may each independently represent 0 or 1.

In yet another exemplary embodiment of Chemical Formula 1, $L_a$ and $L_b$ each independently represent a single bond or phenylene, $Ar_1$ and $Ar_2$ each independently represent a phenyl group unsubstituted or substituted by a methyl group or a phenyl group; a naphthyl group; or the following Chemical Formula 2-1.

[Chemical Formula 2-1]

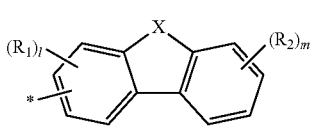

Het₁ and Het₂ each independently represent the following Chemical Formula 3 or the following Chemical Formula 4.

[Chemical Formula 3]

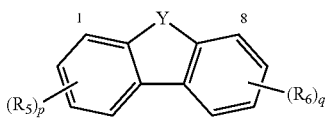

[Chemical Formula 4]

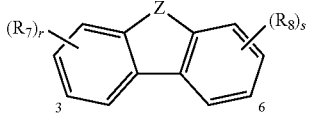

Herein, X represents O, S, or $Si(R_9)(R_{10})$,

Y represents S or O,

Z represents S, $R_5$ and $R_7$ each independently represent a methyl group or a phenyl group, $R_9$ and $R_{10}$ each independently represent a methyl group, p and r each independently represent 0 or 1, and l, m, q, and s may each independently represent 0.

The compound of Chemical Formula 1 may be representatively represented by the following Chemical Formula 5, Chemical Formula 6, or Chemical Formula 7.

[Chemical Formula 5]

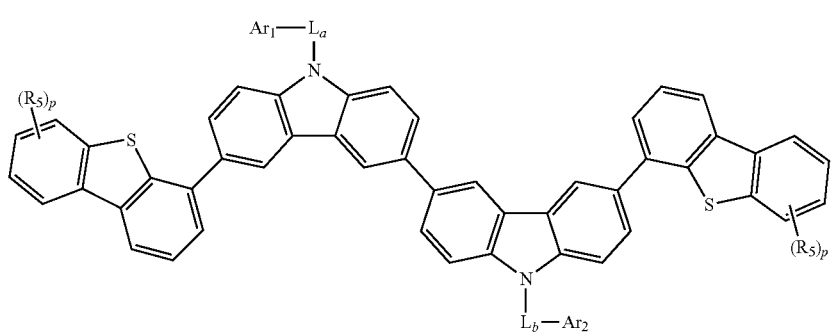

In the Chemical Formula,

Ar$_1$, Ar$_2$, L$_a$, L$_b$, R$_5$, and p are the same as those defined in the above, Ar$_1$ and Ar$_2$ are the same as each other, and L$_a$ and L$_b$ are the same as each other.

[Chemical Formula 6]

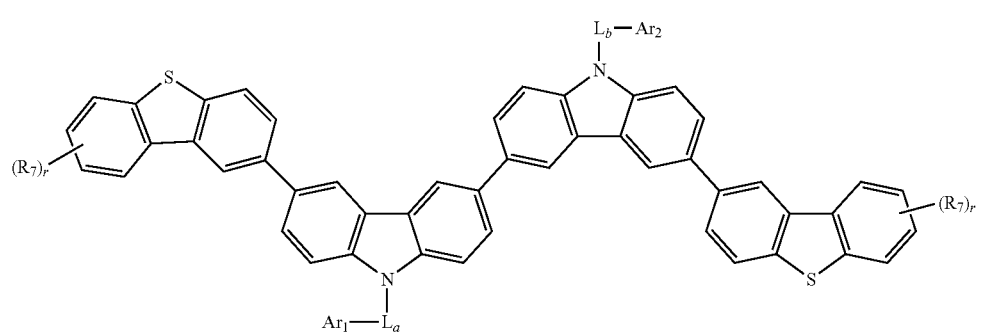

In the Chemical Formula,

Ar$_1$, Ar$_2$, L$_a$, L$_b$, R$_7$, and r are the same as those defined in the above, Ar$_1$ and Ar$_2$ are the same as each other, and L$_a$ and L$_b$ are the same as each other.

[Chemical Formula 7]

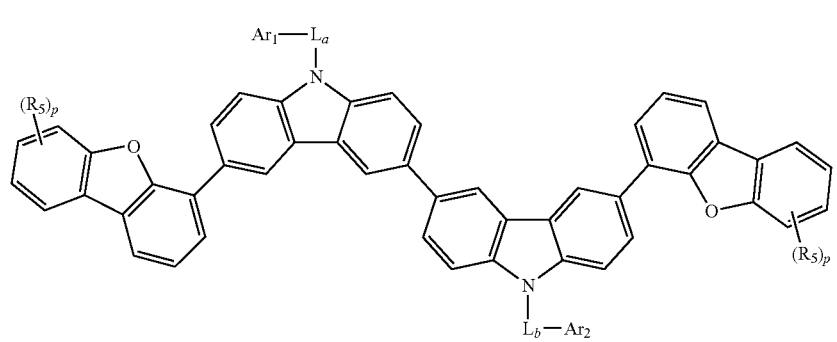

In the Chemical Formula,

Ar$_1$, Ar$_2$, L$_a$, L$_b$, R$_5$, and p are the same as those defined in the above, Ar$_1$ and Ar$_2$ are the same as each other, and L$_a$ and L$_b$ are the same as each other.

Specific examples of the compound represented by Chemical Formula 5 may include compounds represented by the following structure A-1 to structure A-18.

[Structure A-1]

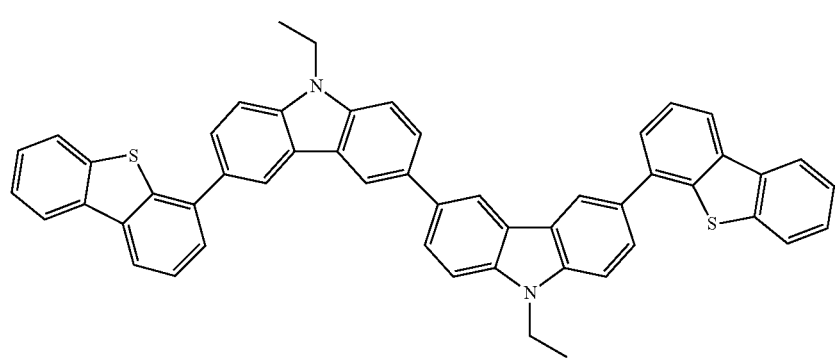

[Structure A-2]
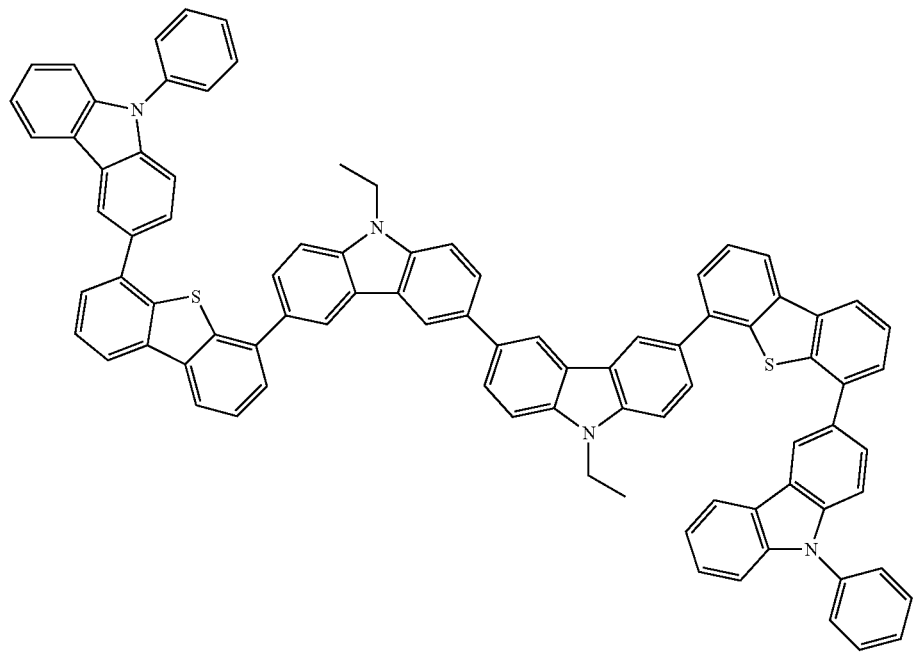
[Structure A-3]
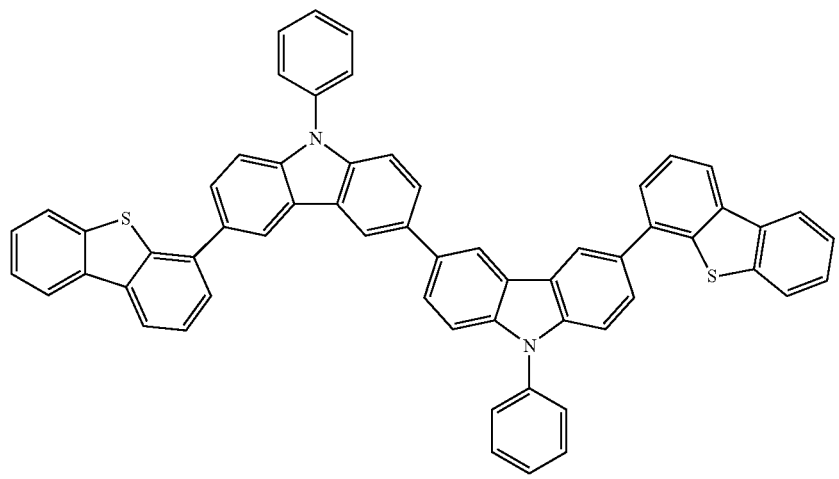

-continued
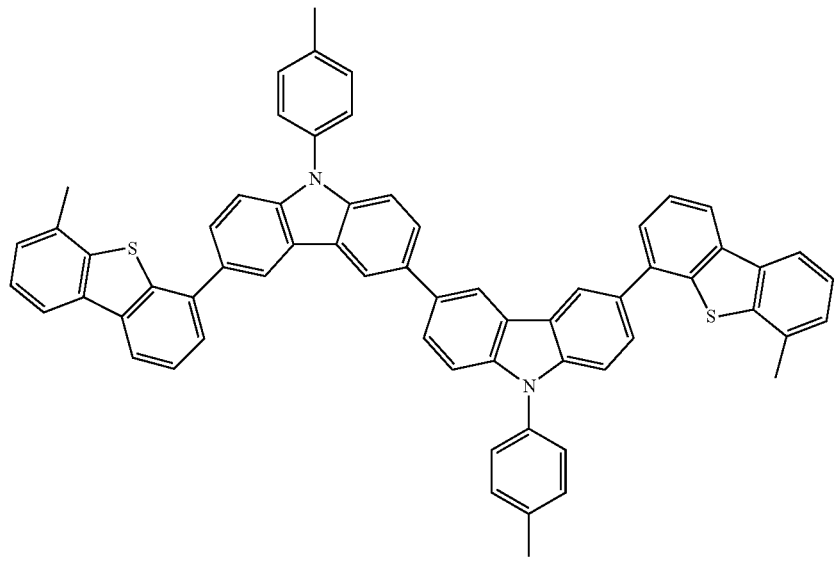
[Structure A-4]
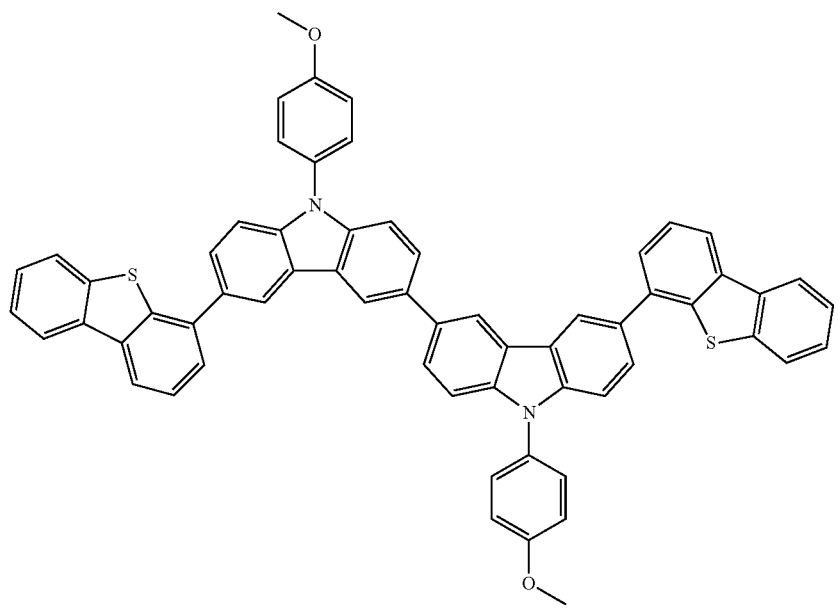
[Structure A-5]

[Structure A-6]
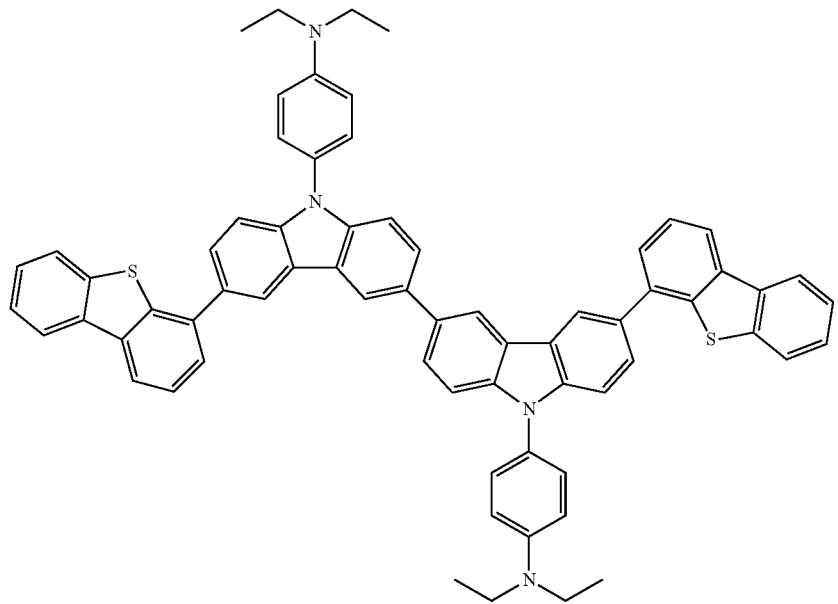
[Structure A-7]
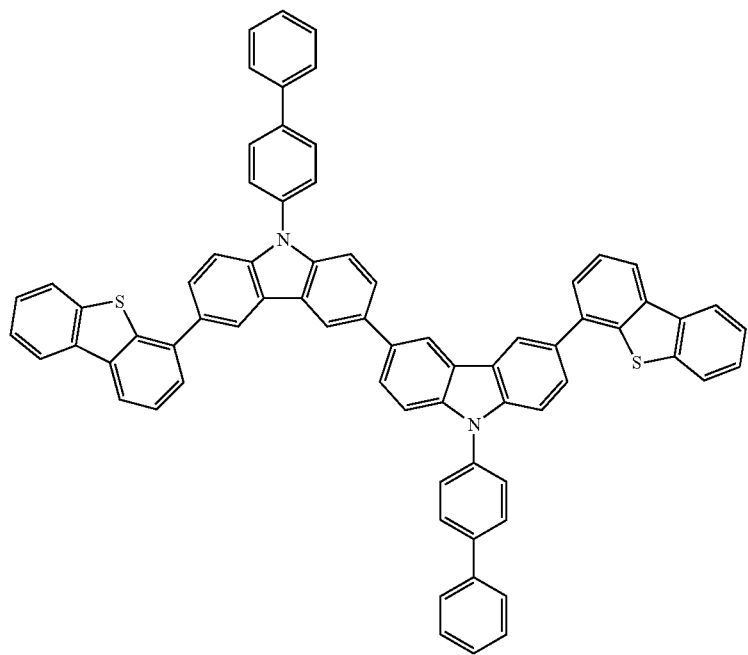

[Structure A-8]
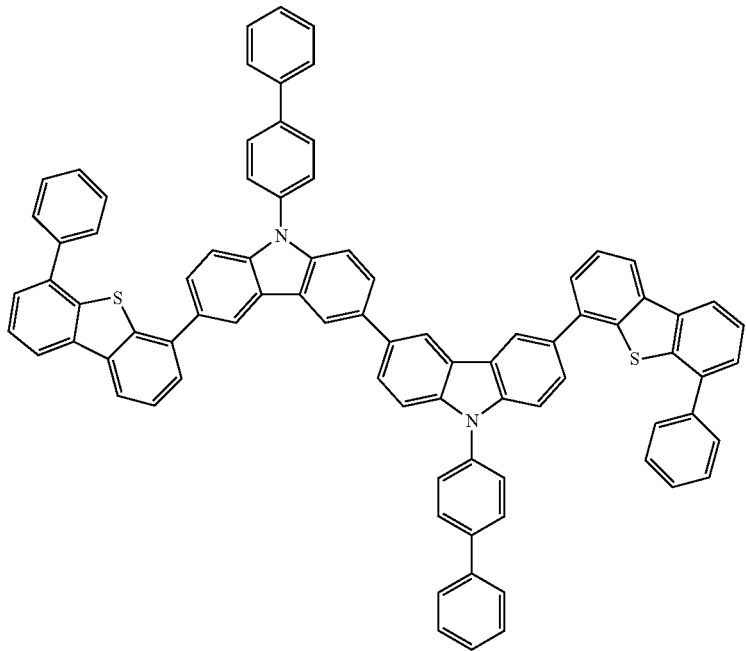
[Structure A-9]
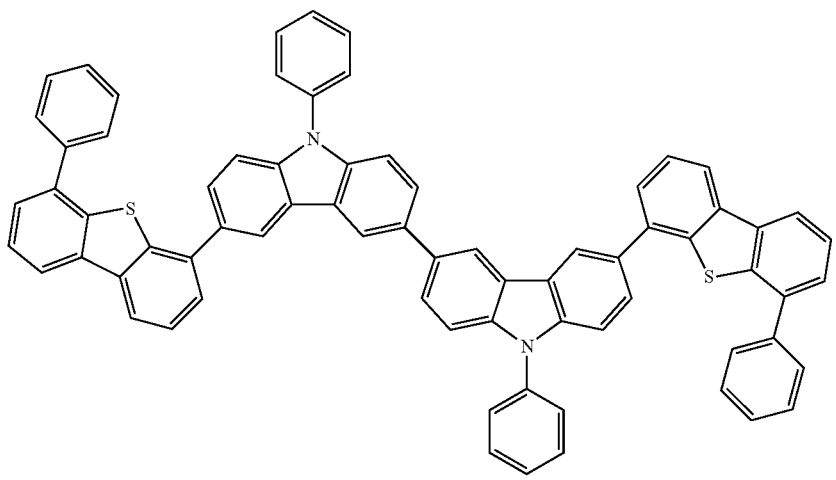

-continued
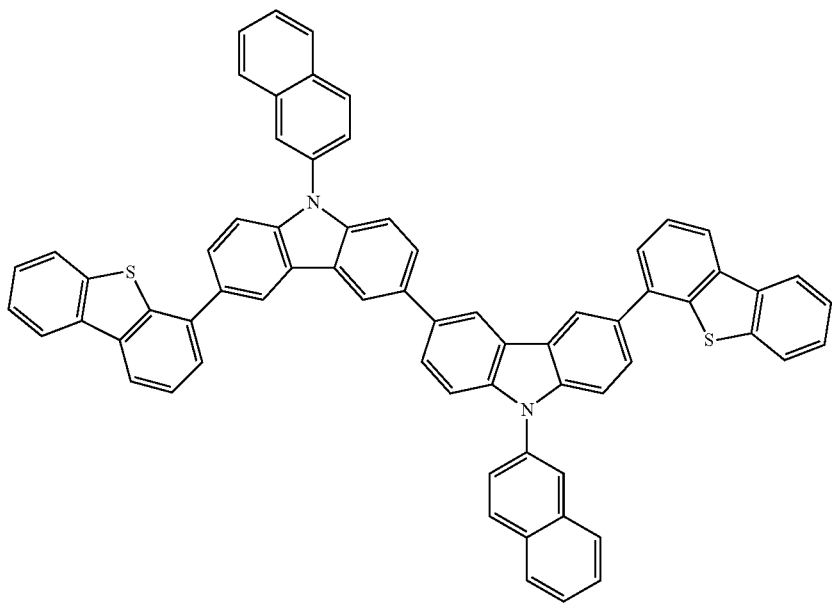
[Structure A-10]
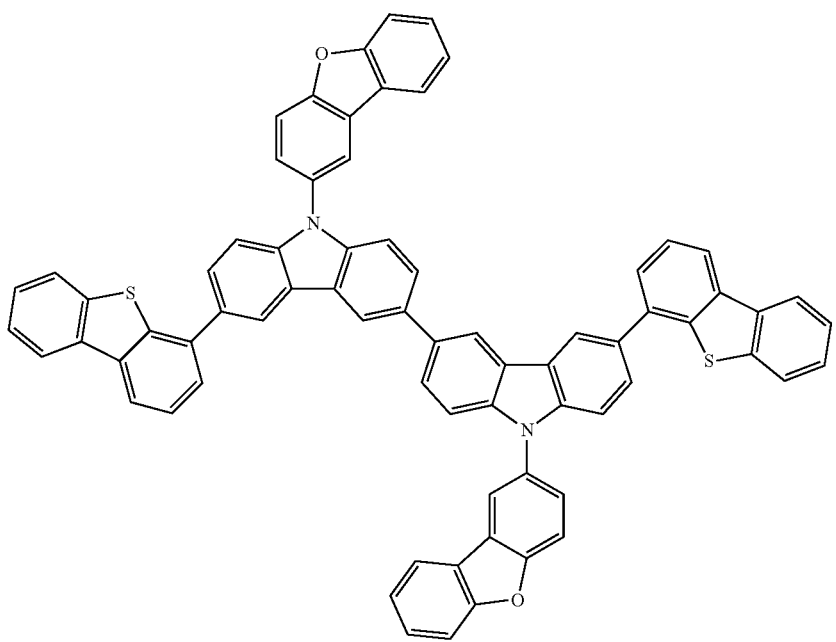
[Structure A-11]

-continued
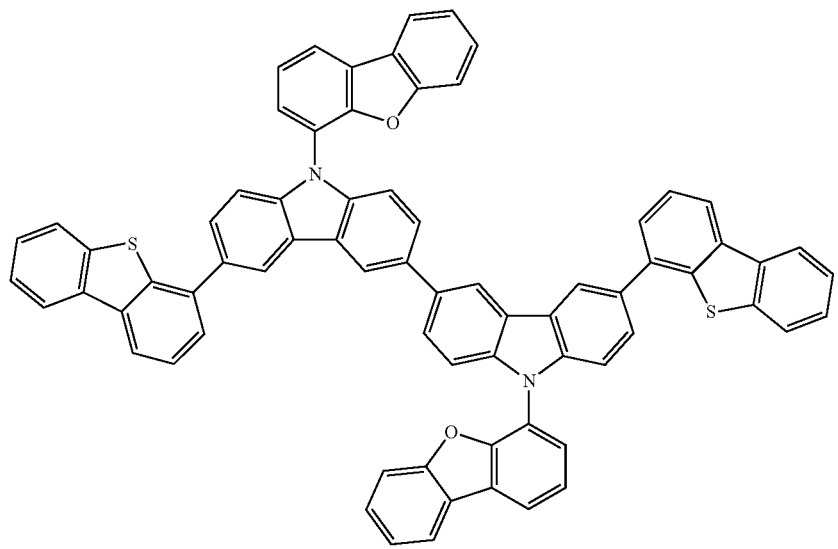
[Structure A-12]
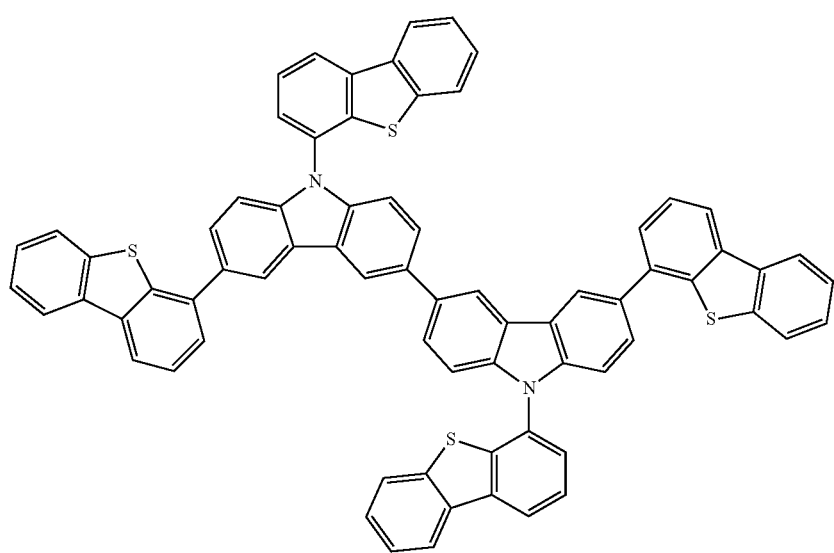
[Structure A-13]

[Structure A-14]
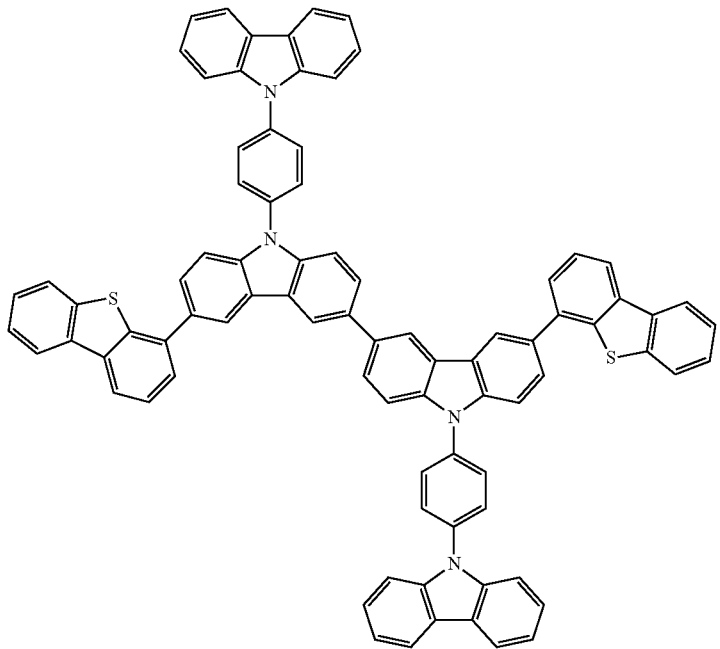
[Structure A-15]
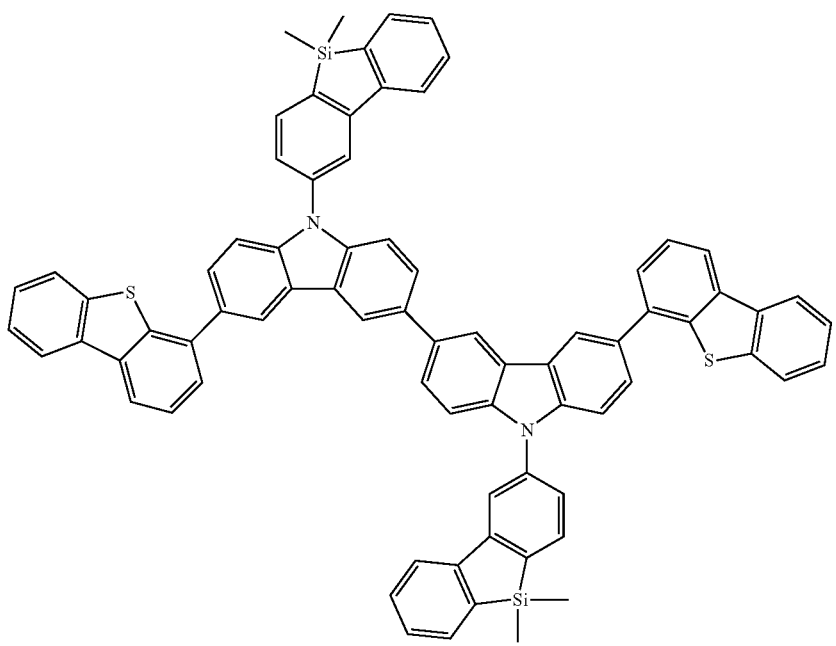

[Structure A-16]
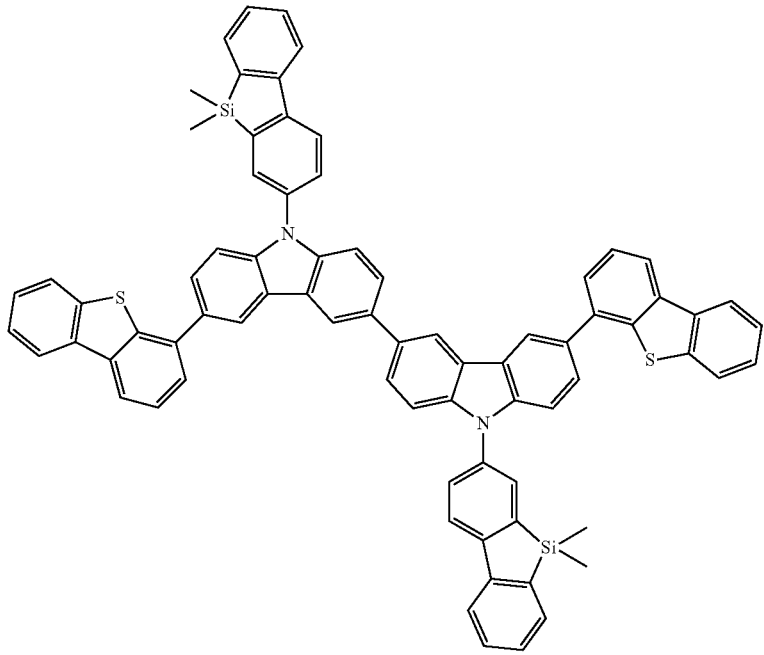
[Structure A-17]
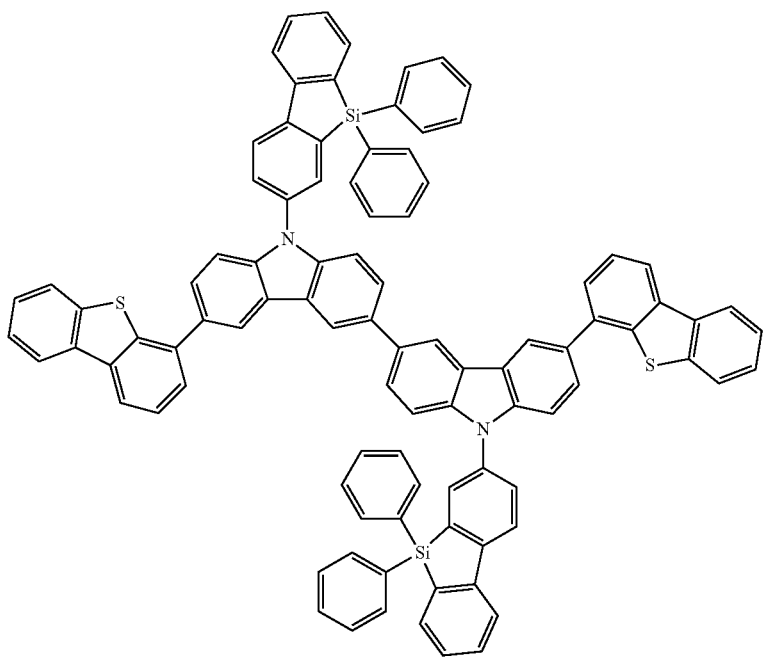

[Structure A-18]
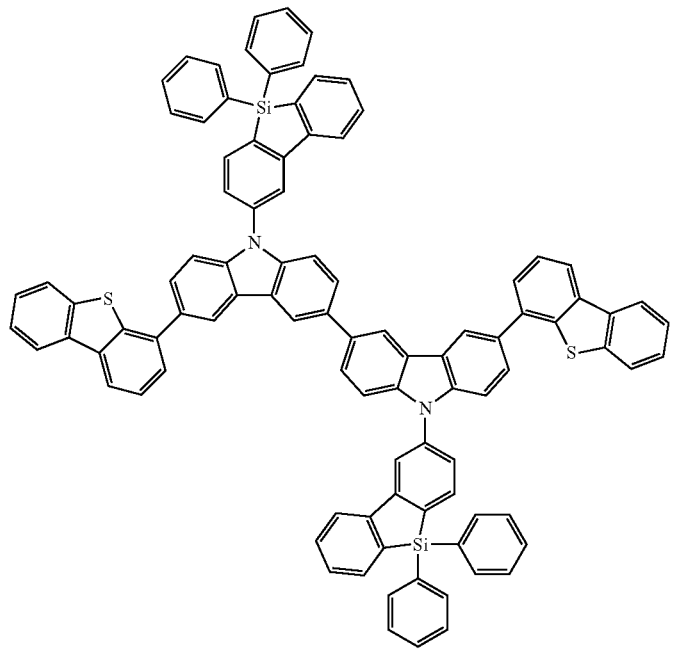
Specific examples of the compound represented by Chemical Formula 6 may include compounds represented by the following structure B-1 to structure B-11.
[Structure B-1]
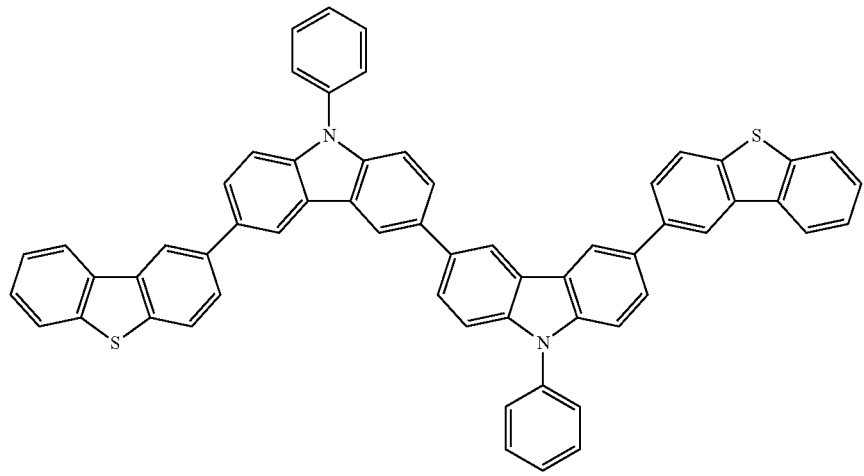

[Structure B-2]
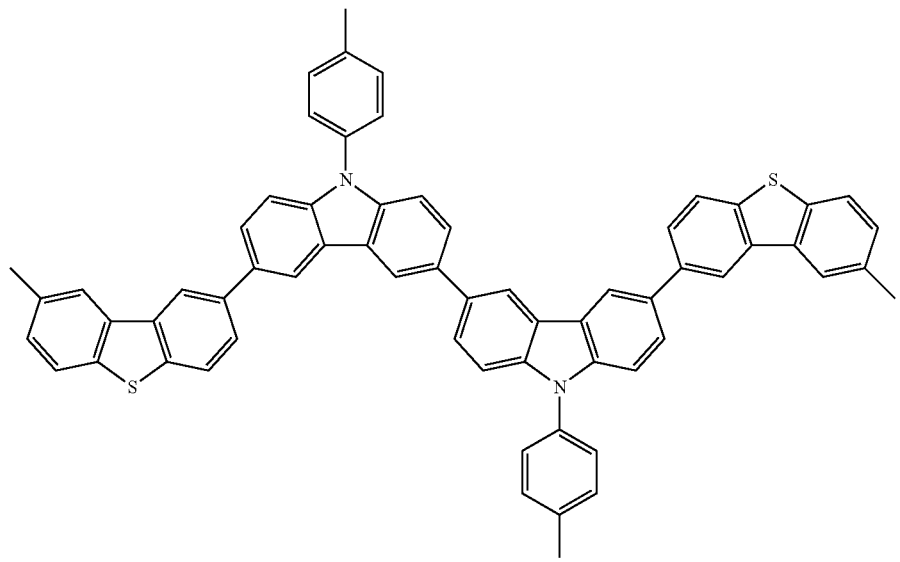
[Structure B-3]
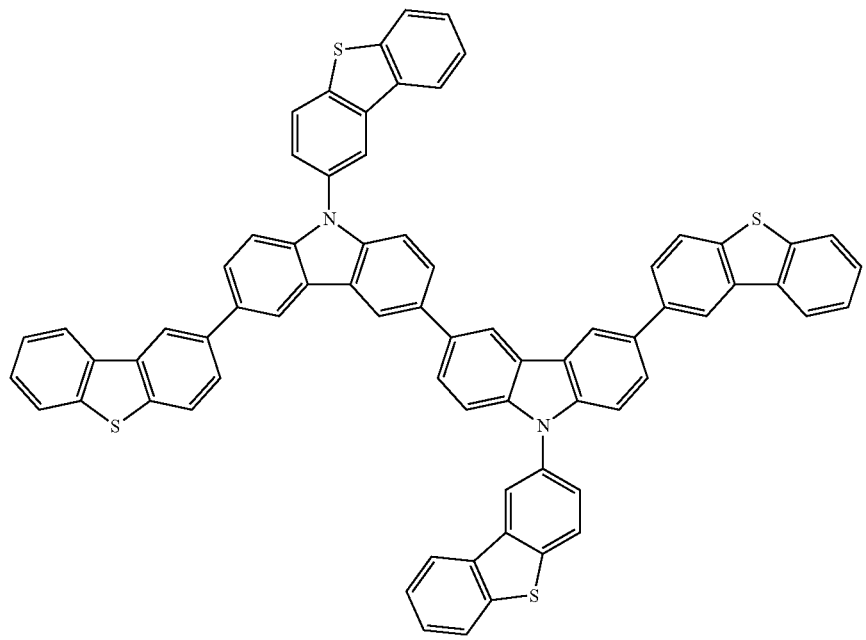

-continued
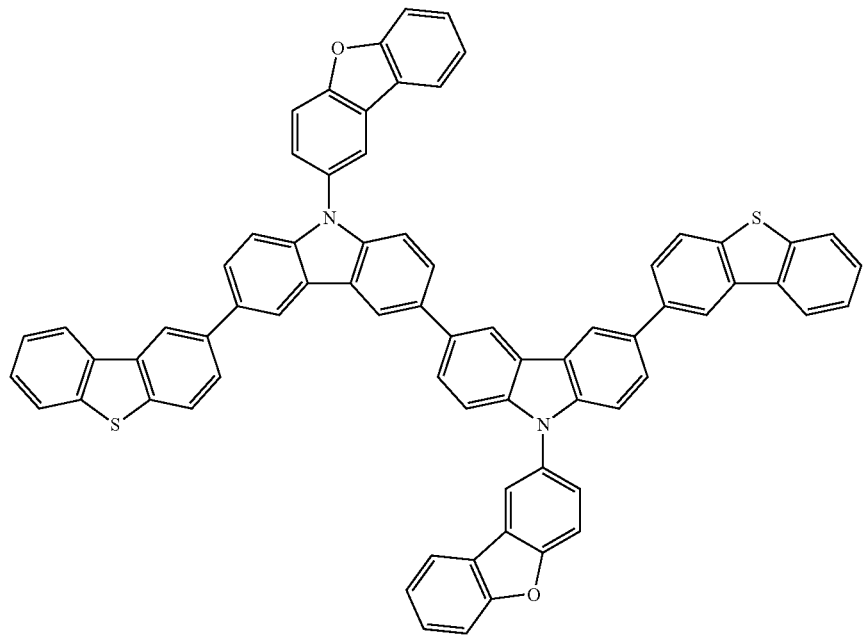
[Structure B-4]
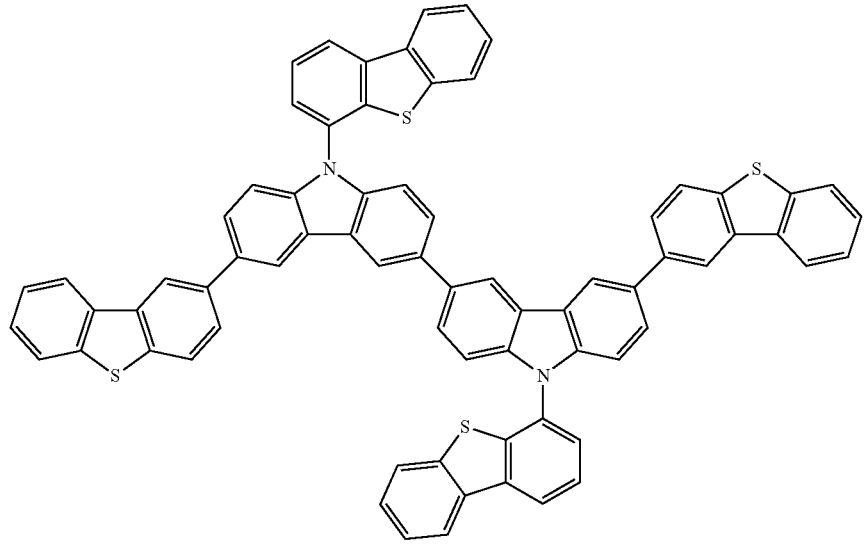
[Structure B-5]

[Structure B-6]
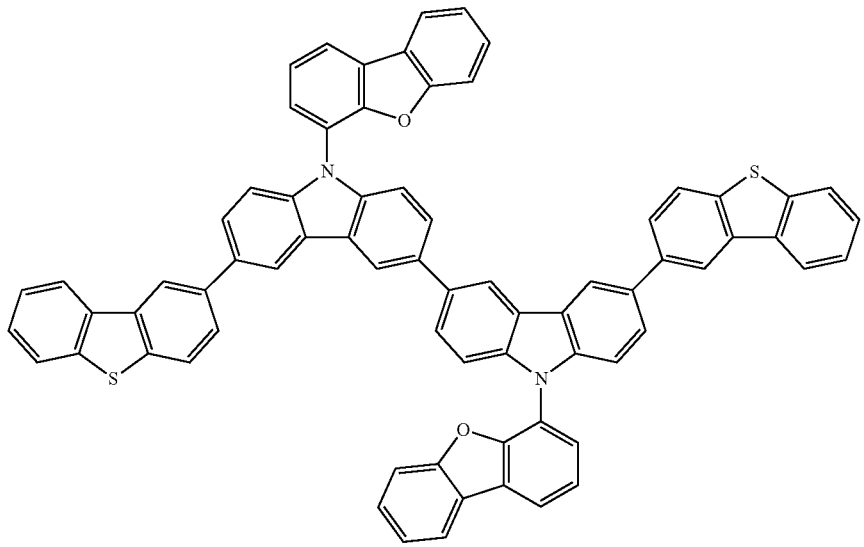
[Structure B-7]
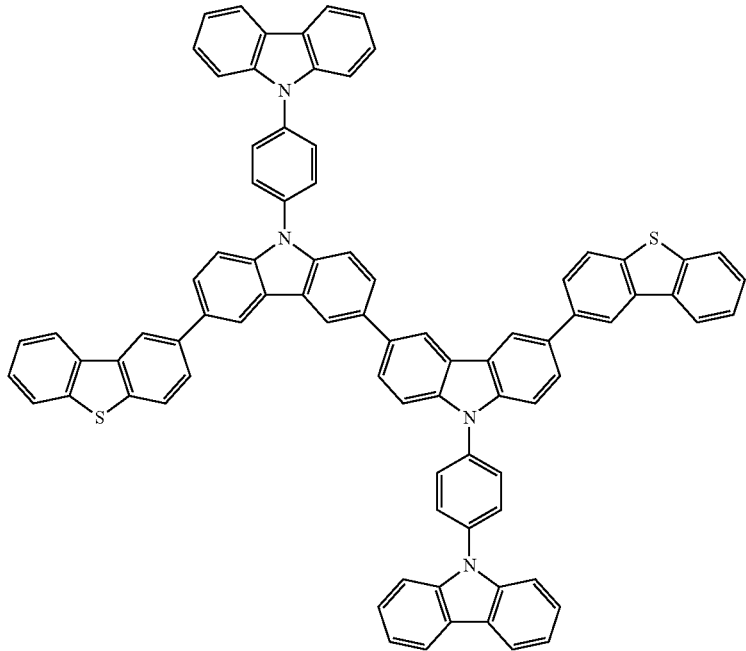

[Structure B-8]
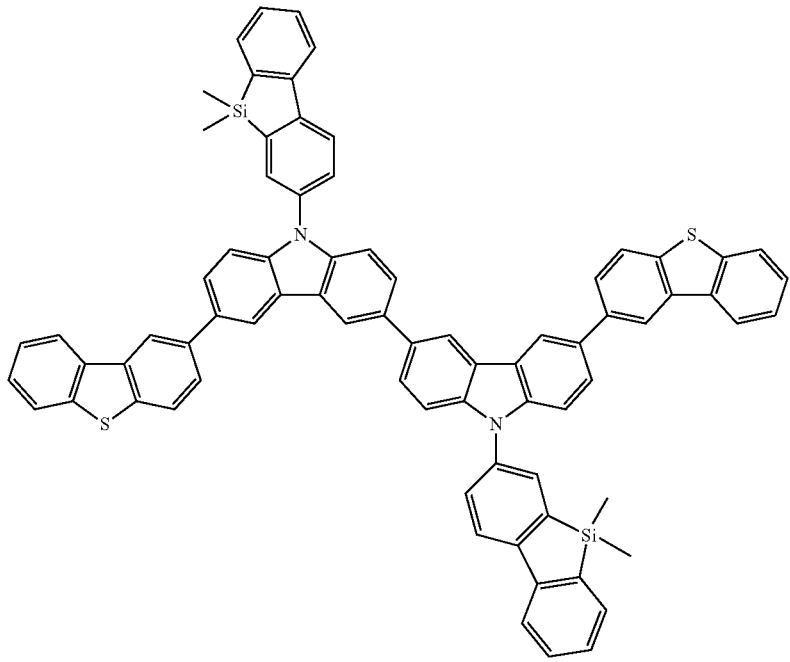
[Structure B-9]
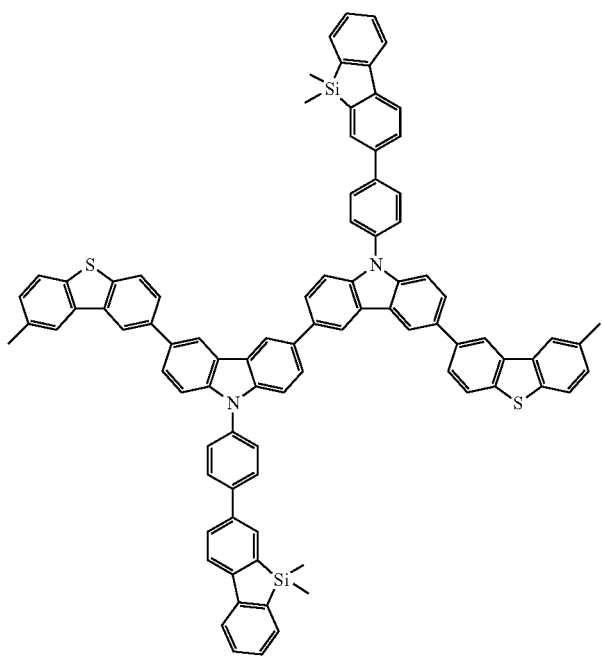

[Structure B-10]
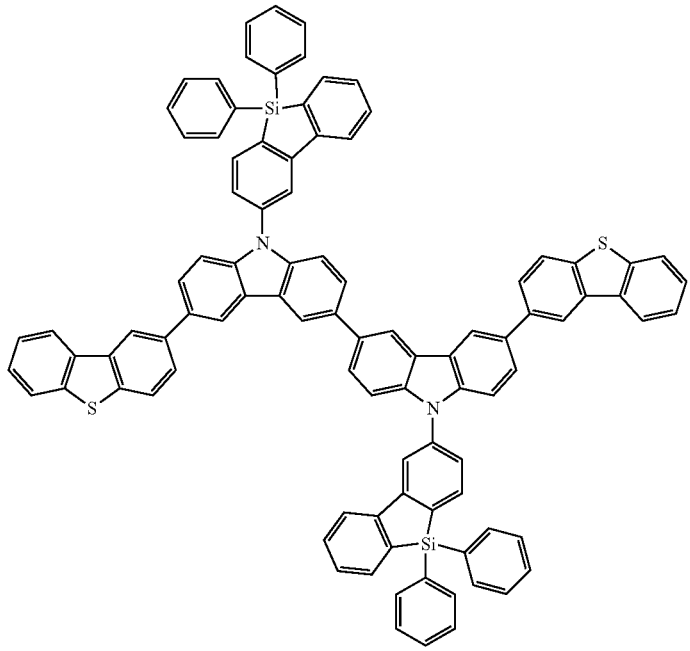
[Structure B-11]
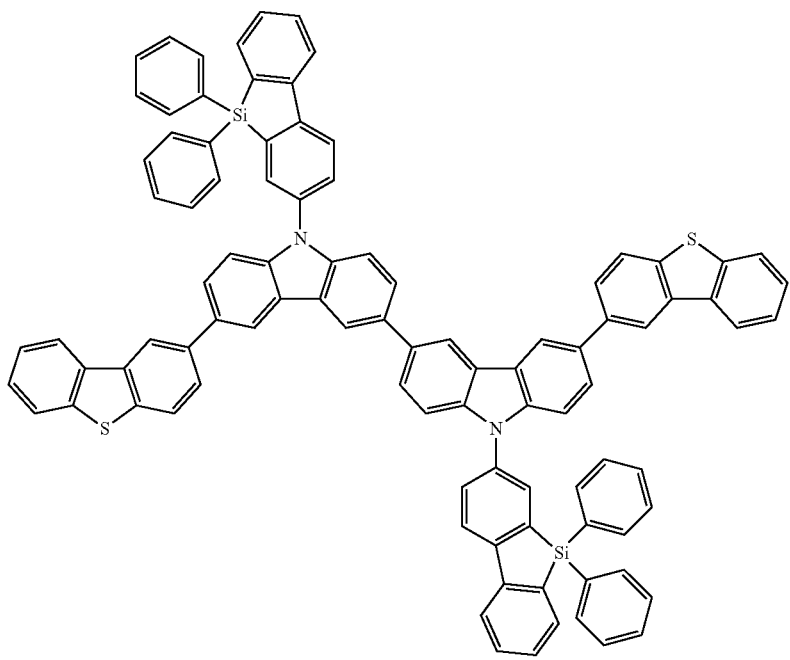
Specific examples of the compound represented by Chemical Formula 7 may include compounds represented by the following structure C-1 to structure C-10.

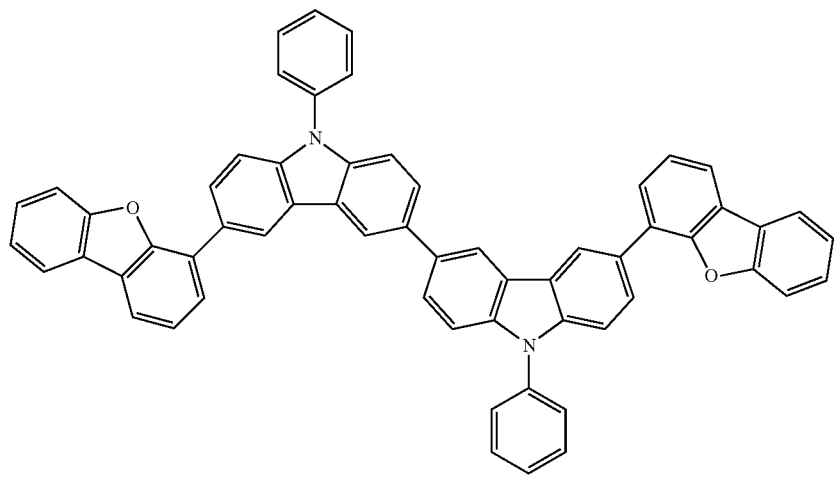
[Structure C-1]
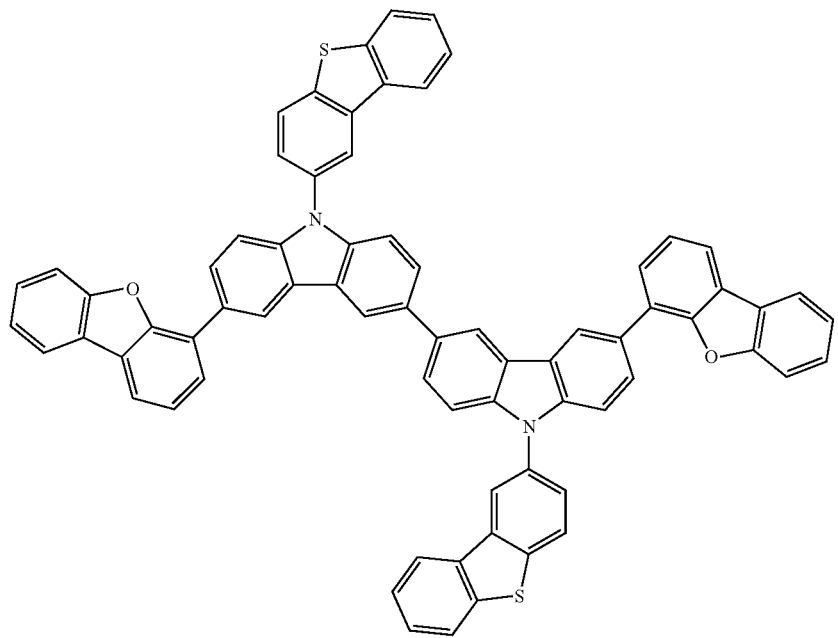
[Structure C-2]

-continued
[Structure C-3]
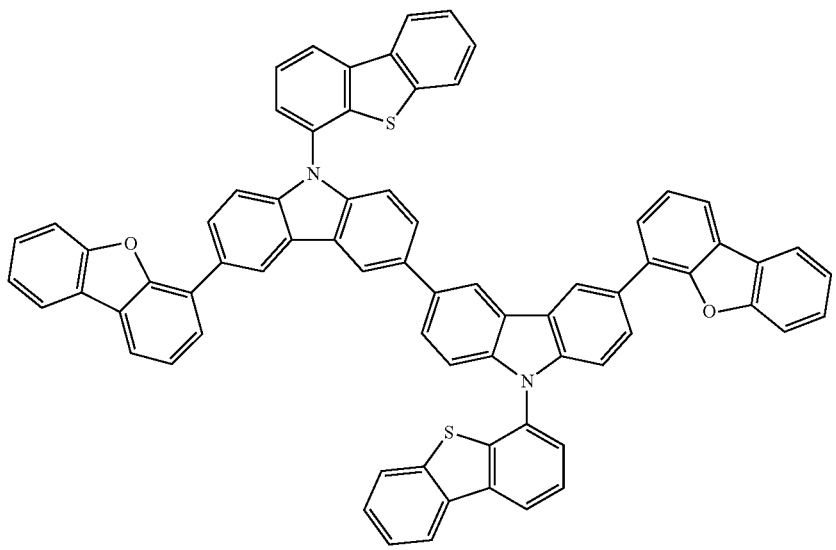
[Structure C-4]
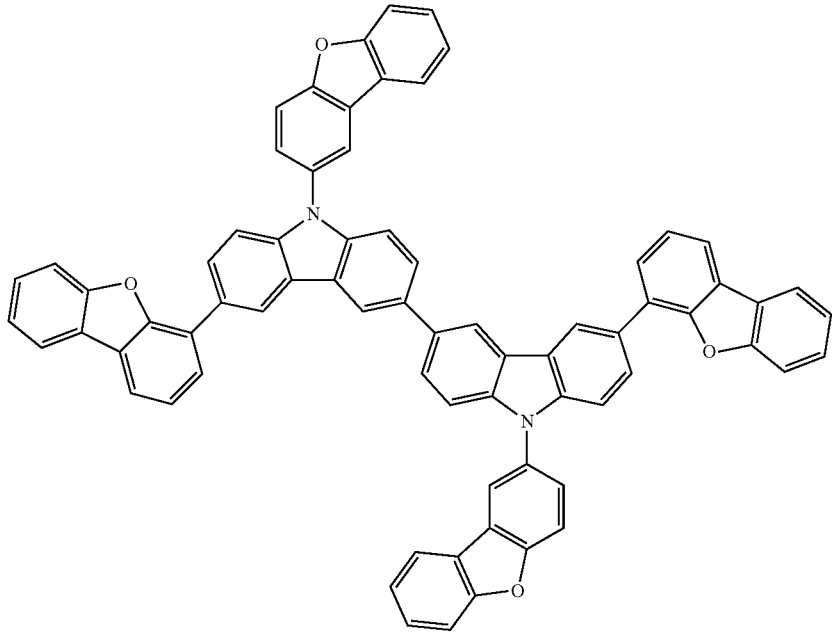

-continued
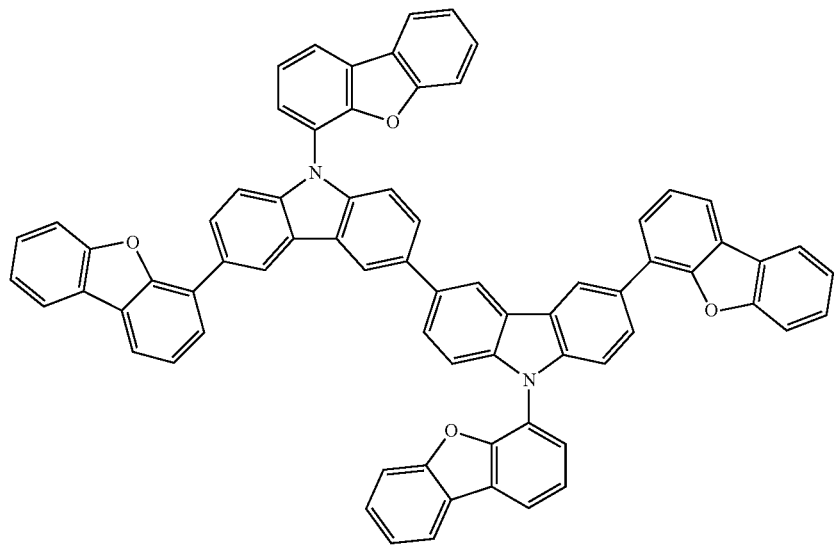
[Structure C-5]
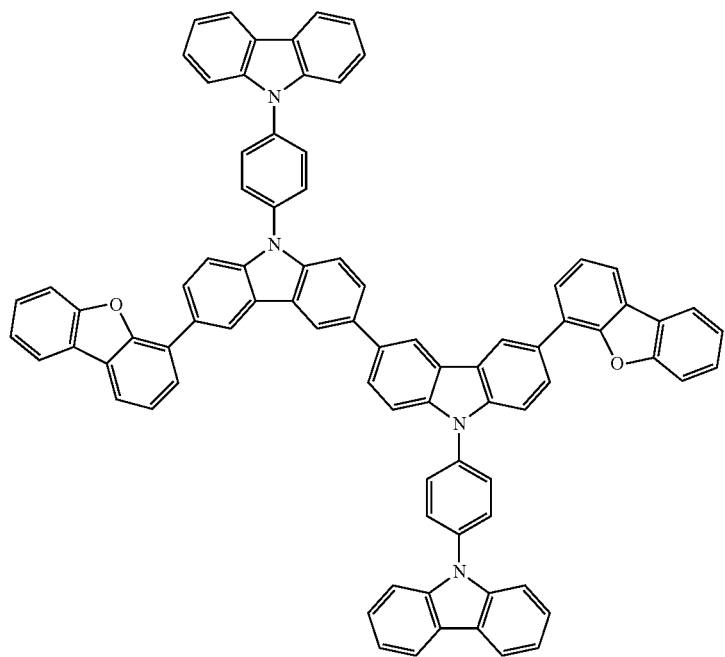
[Structure C-6]

[Structure C-7]
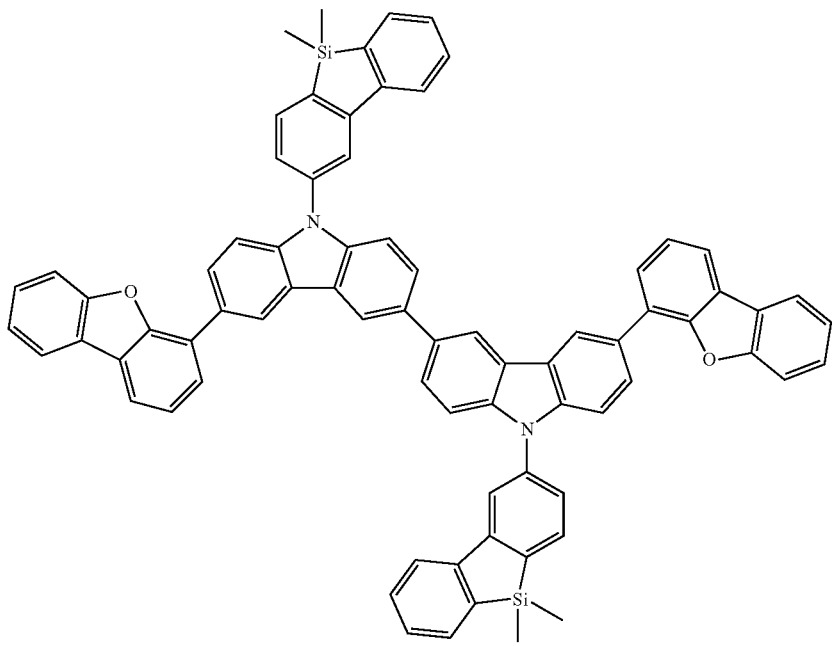
[Structure C-8]
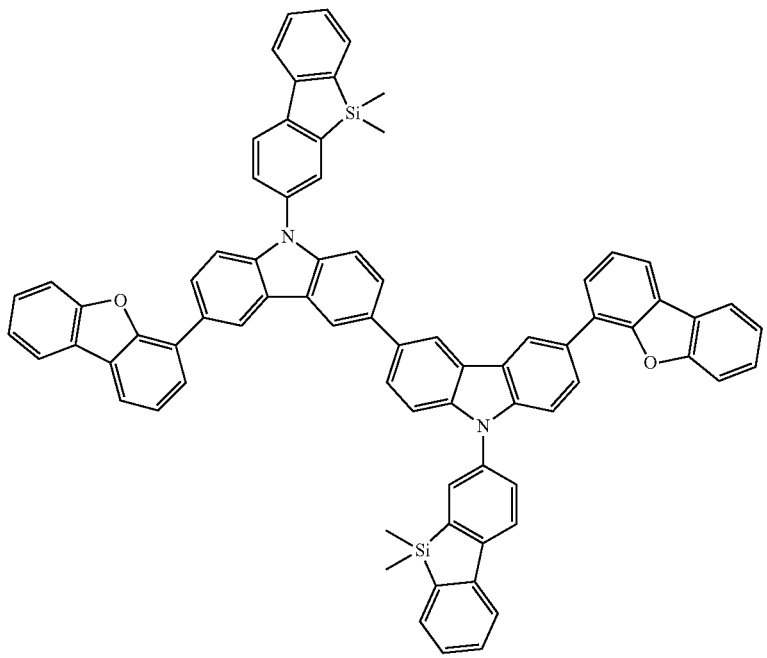

[Structure C-9]

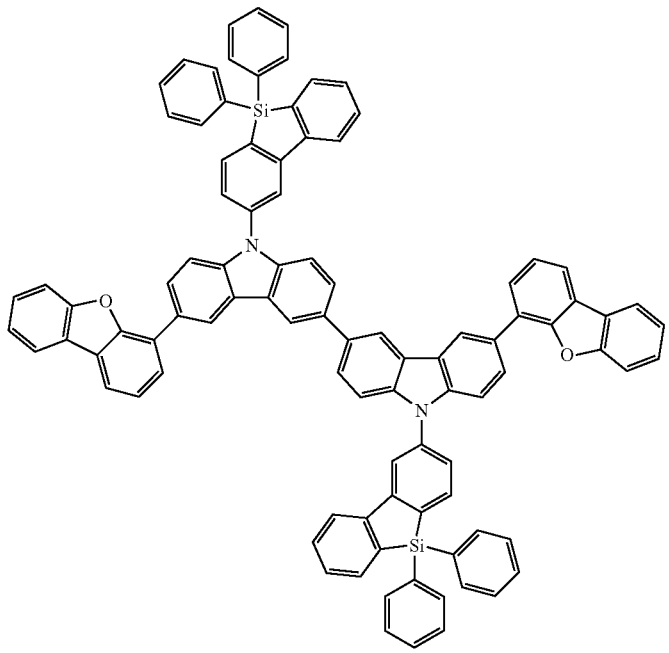

[Structure C-10]

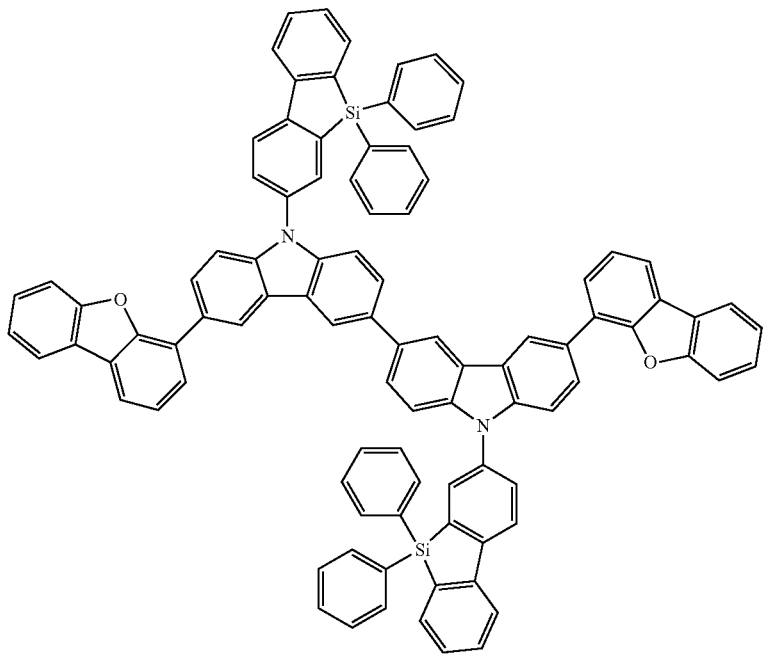

Hereinafter, a light emitting diode including the novel compound according to the present invention will be described with reference to the accompanying drawings. The structure of the light emitting diode including the compound is not limited by the accompanying drawings and the following description.

FIG. 1 is a cross-sectional view for illustrating the light emitting diode according to the exemplary embodiment of the present invention.

Referring to FIG. 1, a light emitting diode 100 includes a first electrode 20, a hole transportable layer 30, a light emitting layer 40, and a second electrode 50 which are formed on a base substrate 10. The light emitting diode 100 may be an organic light emitting diode (OLED).

The first electrode 20 may be formed of a conductive material on the base substrate 10. For example, the first electrode 20 may be a transparent electrode. In this case, the first electrode 20 may be formed of indium tin oxide (ITO). Unlike this, the first electrode 20 may be an opaque (reflective) electrode. In this case, the first electrode 20 may have an ITO/silver (Ag)/ITO structure. The first electrode 20 may become an anode of the light emitting diode 100.

The hole transportable layer 30 is formed on the first electrode 20 to be interposed between the first electrode 20 and the light emitting layer 40. The hole transportable layer 30 includes a compound represented by the following Chemical Formula 1 as a hole transportable compound.

[Chemical Formula 1]

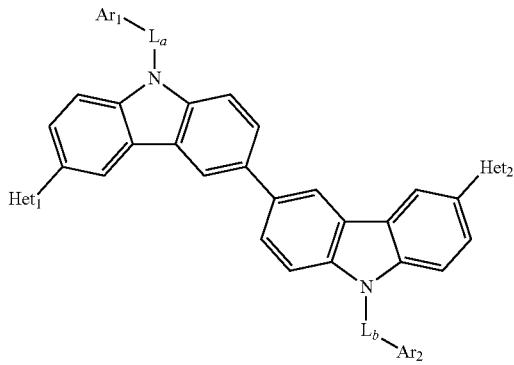

The compound represented by Chemical Formula 1 is the novel compound according to the present invention, and is substantially the same as that described in the above. Accordingly, a specific description of $Ar_1$, $Ar_2$, $L_a$, $L_b$, $Het_1$, and $Het_2$ will be omitted.

A wavelength of light emitted from the light emitting layer 40 may be changed according to a kind of compound forming of the light emitting layer 40.

The second electrode 50 may be formed of a conductive material on the light emitting layer 40. In the case where the first electrode 20 is a transparent electrode, the second electrode 50 may be an opaque (reflective) electrode. In this case, the second electrode 50 may be an aluminum electrode. Unlike this, in the case where the first electrode 20 is an opaque electrode, the second electrode 50 may be a transparent or translucent electrode, and in this case, the second electrode 50 may have a thickness of 100 Å to 150 Å, and may be made of an alloy including magnesium and silver. The second electrode 50 may become a cathode of the light emitting diode 100.

Between the light emitting layer 40 and the second electrode 50, as an electron transportable layer, an electron transport layer and/or an electron injection layer may be formed.

In the case where a current flows between the first and second electrodes 20 and 50 of the light emitting diode 100, holes injected from the first electrode 20 to the light emitting layer 40 and electrons injected from the second electrode 50 to the light emitting layer 40 are combined to form excitons. In a process where the exciton is transferred to a bottom state, light having a wavelength of a specific region band is generated. In this case, the exciton may be a singlet exciton or a triplet exciton. Accordingly, the light emitting diode 100 may provide light to the outside.

Although not illustrated in the drawings, the light emitting diode 100 may further include an electron transport layer (ETL) and an electron injection layer (EIL) disposed between the light emitting layer 40 and the second electrode 50. The electron transport layer and the electron injection layer may be sequentially laminated to be formed on the light emitting layer 40.

Further, the light emitting diode 100 may further include a first blocking layer (not illustrated) disposed between the first electrode 20 and the light emitting layer 40, and/or a second blocking layer (not illustrated) disposed between the light emitting layer 40 and the second electrode 50.

For example, the first blocking layer may be an electron blocking layer (EBL) which is disposed between the hole transportable layer 30 and the light emitting layer 40 to prevent the electrons injected from the second electrode 50 from flowing through the light emitting layer 40 into the hole transportable layer 30. Further, the first blocking layer may be an exciton blocking layer preventing the exciton formed in the light emitting layer 40 from being diffused in a direction of the first electrode 20 to become extinct without light emission. Further, the first blocking layer may be an exciton dissociation blocking layer (EDBL). The exciton dissociation blocking layer may prevent the exciton formed in the light emitting layer 40 from becoming extinct without light emission through an exciton dissociation process at an interface between the light emitting layer 40 and the hole transportable layer 30. In order to prevent dissociation of the exciton at the interface, the compound forming of the first blocking layer may be selected to have a HOMO value at a level that is similar to that of the compound forming of the light emitting layer 40.

In this case, the first blocking layer may include the aforementioned compound according to the present invention.

The second blocking layer may be a hole blocking layer (HBL) which is disposed between the light emitting layer 40 and the second electrode 50 and specifically between the light emitting layer 40 and the electron transport layer to prevent the holes from flowing from the first electrode 20 through the light emitting layer 40 into the electron transport layer. Further, the second blocking layer may be an exciton blocking layer preventing the exciton formed in the light emitting layer 40 from being diffused in a direction of the second electrode 50 to become extinct without light emission.

If a thickness of each of the first and second blocking layers is adjusted to be attuned to a resonance length of the light emitting diode 100, light emitting efficiency may be increased, and the thickness may be adjusted so that the exciton is formed at the center of the light emitting layer 40.

Referring to FIG. 2, a light emitting diode 102 includes a first electrode 20, a hole transportable layer 32, a light emitting layer 40, and a second electrode 50 which are formed on a base substrate 10. Since the light emitting diode is substantially the same as that illustrated in FIG. 1 with the exception of the hole transportable layer 32, an overlapping description will be omitted.

The hole transportable layer 32 includes the compound represented by Chemical Formula 1, and a P-type dopant. Since the compound included in the hole transportable layer 32 is substantially the same as that described in the above, an overlapping specific description will be omitted.

The P-type dopant may include a P-type organic dopant, and/or a P-type inorganic dopant.

Specific examples of the P-type organic dopant may include compounds represented by the following Chemical Formulas 8 to 12, hexadecafluorophthalocyanine (F16CuPc), 11,11,12,12-tetracyanonaphtho-2,6-quinodimethane (TNAP), 3,6-difluoro-2,5,7,7,8,8-hexacyano-quinodimethane (F2-HCNQ), tetracyanoquinodimethane (TCNQ), or the like. The examples may be used alone or in combination of two or more thereof.

[Chemical Formula 8]

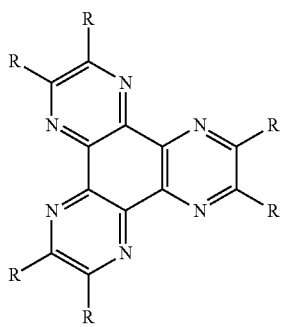

In Chemical Formula 8, R may represent a cyano group, a sulfone group, a sulfoxide group, a sulfonamide group, a sulfonate group, a nitro group, or a trifluoromethyl group.

[Chemical Formula 9]

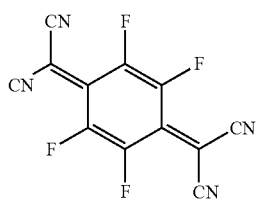

[Chemical Formula 10]

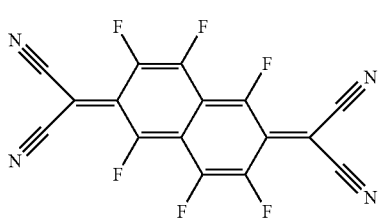

[Chemical Formula 11]

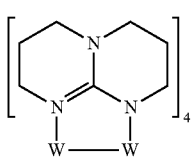

[Chemical Formula 12]

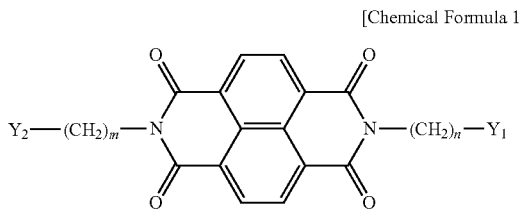

In Chemical Formula 12, m and n may each independently represent an integer of 1 to 5, and $Y_1$ and $Y_2$ may each independently represent an aryl group having 6 to 20 carbon atoms or a heteroaryl group having 2 to 20 carbon atoms. In this case, in Chemical Formula 12, hydrogen of the aryl group or the heteroaryl group represented by $Y_1$ and $Y_2$ may be unsubstituted or substituted by an alkyl group having 1 to 5 carbon atoms, an alkoxy group having 1 to 5 carbon atoms, or a hydroxyl group, and hydrogens of substituted or unsubstituted $Y_1$ and $Y_2$ may be each independently unsubstituted or substituted by a halogen group.

For example, the compound represented by Chemical Formula 12 may include a compound represented by the following Chemical Formula 12a or the following Chemical Formula 12b.

[Chemical Formula 12a]

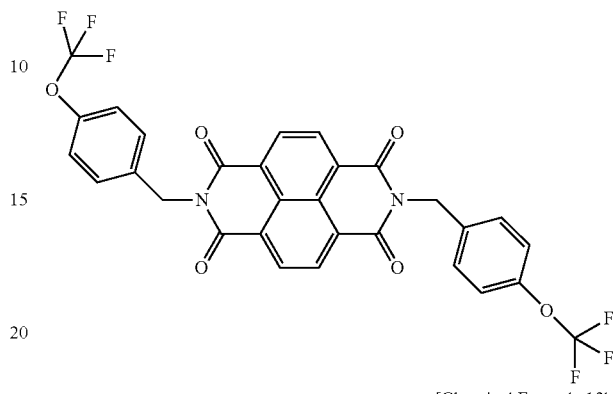

[Chemical Formula 12b]

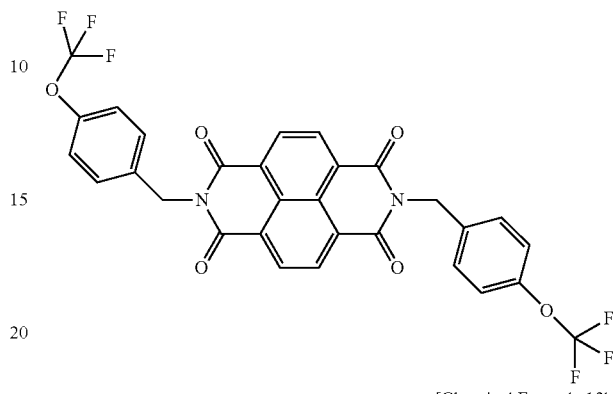

Examples of the P-type inorganic dopant may include metal oxides, metal halides, or the like. Specific examples of the P-type inorganic dopant may include $MoO_3$, $V_2O_5$, $WO_3$, $SnO_2$, $ZnO$, $MnO_2$, $CoO_2$, $ReO_3$, $TiO_2$, $FeCl_3$, $SbCl_5$, $MgF_2$, or the like. The examples may be used alone or in combination of two or more thereof.

A content of the P-type dopant may be about 0.5 parts by weight to about 20 parts by weight based on 100 parts by weight of the novel compound according to the present invention, which is a hole transportable compound. For example, the content of the P-type dopant may be about 0.5 parts by weight to about 15 parts by weight or about 0.5 parts by weight to about 5 parts by weight based on 100 parts by weight of the hole transportable compound. Unlike this, the content of the P-type dopant may be about 1 part by weight to 10 parts by weight, 1 part by weight to 5 parts by weight, 1.5 parts by weight to 6 parts by weight, or 2 parts by weight to 5 parts by weight based on 100 parts by weight of the hole transportable compound.

In the case where the content of the P-type dopant is about 0.5 parts by weight to about 20 parts by weight based on 100 parts by weight of the hole transportable compound, the P-type dopant may not degrade physical properties of the hole transportable compound and may prevent generation of an excessive leakage current. Further, energy barriers at interfaces with upper and lower layers coming into contact with the hole transportable layer 32 may be reduced by the P-type dopant.

Although not illustrated in the drawings, the light emitting diode 102 may further include the electron transport layer, the electron injection layer, the first blocking layer, and/or the second blocking layer. Since the layers are substantially the same as those described in the light emitting diode 100 of FIG. 1, a specific description will be omitted. In the case where the light emitting diode 102 includes the first blocking layer, the first blocking layer may include the aforementioned compound according to the present invention.

Meanwhile, the light emitting diode 100 illustrated in FIG. 1 may further include an interlayer (not illustrated). The interlayer may be disposed between the first electrode 20 and the hole transportable layer 30 of FIG. 1, and may be formed of the compound used as the P-type dopant described in FIG. 2.

Referring to FIG. 3, a light emitting diode 104 includes a first electrode 20, a hole transportable layer 34, a light emitting layer 40, and a second electrode 50 which are formed on a base substrate 10. Since the light emitting diode is substantially the same as that illustrated in FIG. 1 with the exception of the hole transportable layer 34, an overlapping description will be omitted.

The hole transportable layer 34 includes a first layer 33a coming into contact with the first electrode 20, and a second layer 33b disposed between the first layer 33a and the light emitting layer 40. That is, the hole transportable layer 34 may have a two-layered structure. Further, the hole transportable layer 34 may have a multilayered structure of two layers or more including the first and second layers 33a and 33b.

The first and second layers 33a and 33b may include the same kind of hole transportable compound. By using components of the hole transportable compounds included in the first layer 33a and the second layer 33b to be the same as each other, physical and chemical defects that may occur at an interface between heteromaterials may be reduced, and thus holes may be easily injected into the light emitting layer. In another aspect, if the same host material is used in the first layer 33a and the second layer 33b, since the first layer 33a and the second layer 33b may be continuously formed in one chamber, a manufacturing process is simplified and a manufacturing time may be shortened. Moreover, there is a merit in that since physical properties such as a glass transition temperature between the adjacent layers become similar to each other, durability of the element may be increased.

The first layer 33a includes the novel compound according to the present invention represented by Chemical Formula 1 as the hole transportable compound, and the P-type dopant. The first layer 33a is substantially the same as the hole transportable layer 32 described in FIG. 2 with the exception of the thickness. Accordingly, an overlapping description will be omitted.

The second layer 33b includes the novel compound according to the present invention represented by Chemical Formula 1 as the hole transportable compound, and the hole transportable compound constituting the second layer 33b may be the same as the hole transportable compound constituting the first layer 33a. Since the second layer 33b is substantially the same as the hole transportable layer 30 described in FIG. 1 with the exception of the thickness, an overlapping detailed description will be omitted.

Unlike this, the first and second layers 33a and 33b may include different kinds of hole transportable compounds. The hole transportable compounds constituting the first and second layers 33a and 33b are the novel compounds according to the present invention represented by Chemical Formula 1, and $Ar_1$, $Ar_2$, $L_a$, $L_b$, $Het_1$, and $Het_2$ may be each independently different from each other. In this case, the compound constituting each of the first and second layers 33a and 33b may be selected to have a HOMO value for effectively transferring holes to the light emitting layer 40.

Additionally, the second layer 33b may further include the P-type dopant together with the hole transportable compound. In this case, the kinds of the P-type dopants doped on the first layer 33a and the second layer 33b may be different from each other, and even though the same kind is used, doping amounts may be different from each other. For example, the content P1 of the P-type dopant doped on the first layer 33a and the content P2 of the P-type dopant doped on the second layer 33b may satisfy a relationship of the following Equation 1.

$$P1/P2 \geq 1 \qquad \text{[Equation 1]}$$

In Equation 1,

"P1" is the content of the doped P-type dopant based on 100 parts by weight of the hole transportable compound in the first layer 33a, and "P2" is the content of the doped P-type dopant based on 100 parts by weight of the hole transportable compound in the second layer 33b.

For example, the content of the P-type dopant doped on the first layer 33a may be in the range of 0.3 to 20 parts by weight, 1 to 15 parts by weight, 2 to 10 parts by weight, or 4 to 6 parts by weight based on 100 parts by weight of the hole transportable compound. Further, the content of the P-type dopant doped on the second layer 33b may be in the range of 0.3 to 20 parts by weight, 0.5 to 10 parts by weight, 1 to 8 parts by weight, or 2 to 4 parts by weight based on 100 parts by weight of the hole transportable compound.

Further, although not illustrated in the drawings, the light emitting diode 104 may further include the electron transport layer, the electron injection layer, the first blocking layer, and/or the second blocking layer. Since the layers are substantially the same as those described in the light emitting diode 100 of FIG. 1, a specific description will be omitted.

Each of the aforementioned light emitting diodes 100, 102, and 04 may include the novel compound according to the present invention represented by Chemical Formula 1, and thus the light emitting diodes 100, 102, and 104 may have excellent thermal stability, and simultaneously light emitting efficiency may be improved and a life-span may be lengthened.

FIGS. 1 to 3 illustrate that the light emitting diodes 100, 102, and 104 are directly formed on the base substrate 10, but a thin film transistor as a driving element driving a pixel may be disposed between the first electrode 20 and the base substrate 10 of each of the light emitting diodes 100, 102, and 104. In this case, the first electrode 20 may become a pixel electrode connected to the thin film transistor. In the case where the first electrode 20 is the pixel electrode, the first electrodes 20 may be disposed to be separated from each other in a plurality of pixels and a partition wall pattern formed along an edge of the first electrode 20 may be formed on the base substrate 10 to isolate layers laminated on the first electrodes 20 disposed in the pixels that are adjacent to each other from each other. That is, although not illustrated in the drawings, the light emitting diodes 100, 102, and 104 may be used in a display device displaying an image without a backlight.

Further, the light emitting diodes 100, 102, and 104 may be used as a lighting device.

As described above, the light emitting diodes 100, 102, and 104 exemplified in the present invention may be used in various electronic apparatus such as the display device or the lighting device.

EXAMPLES

Hereinafter, the novel compounds according to the present invention will be described in more detail through specific Examples according to the present invention. The Examples exemplified below are set forth only for the detailed description of the invention, but are not to be construed to limit the scope of the right.

Example 1

30 minutes. Further, potassium carbonate ($K_2CO_3$) (150.2 mmol, 20.8 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.80 mmol, 0.87 g) was added to the 1 L three-neck round bottom flask, light was blocked and reflux was performed for 6 hours. The reaction mixture was cooled, extracted and concentrated by using ethyl acetate (EA) and distilled water, dissolved in 100 mL of tetrahydrofuran (THF), and added to 1 L of methanol,

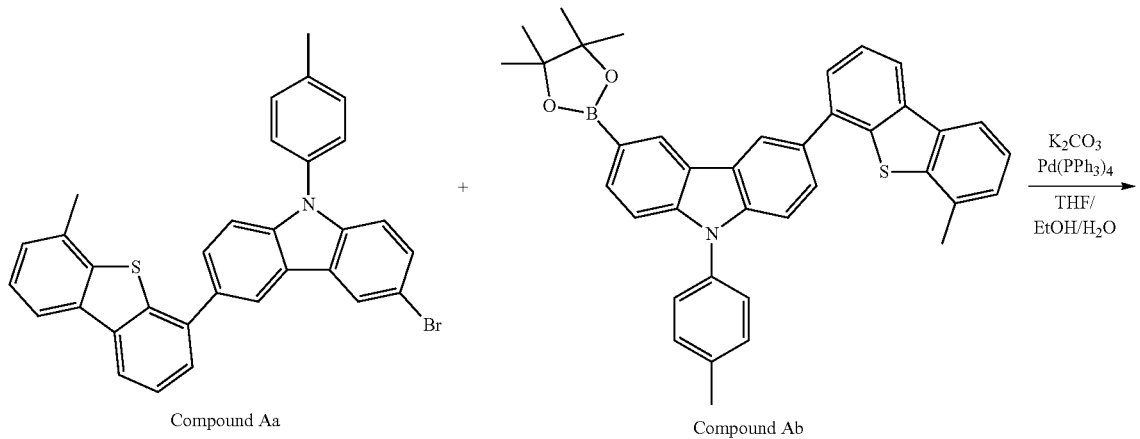

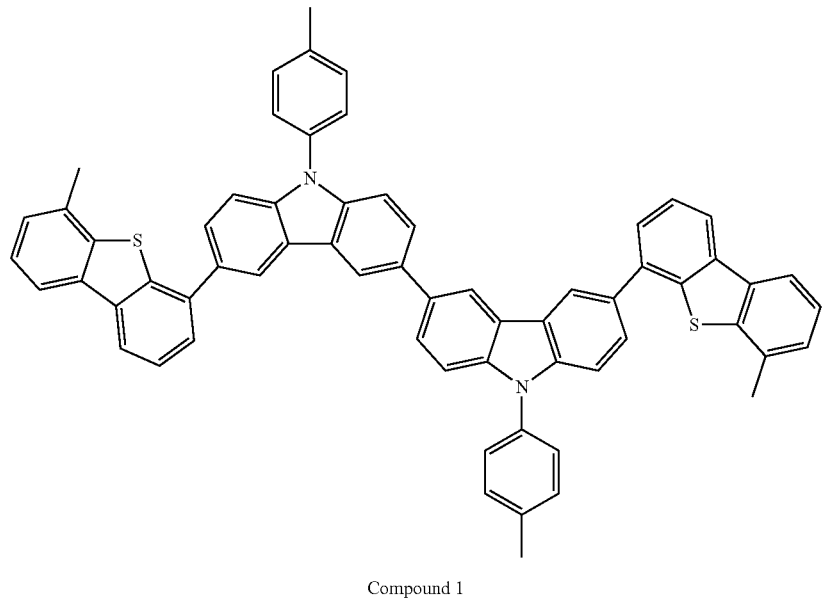

Compound 1

After nitrogen was charged in the 1 L three-neck round bottom flask, compound Aa (37.6 mmol, 20.0 g), compound Ab (41.3 mmol, 23.9 g), 200 mL of tetrahydrofuran (THF), and 100 mL of ethanol (EtOH) were added and agitated for followed by agitation for 20 minutes and filtration to obtain 27.2 g of compound 1 that was the light grey solid (yield 80%).

MALDI-TOF: m/z=904.3319 ($C_{64}H_{44}N_2S_2$=904.29)

Example 2

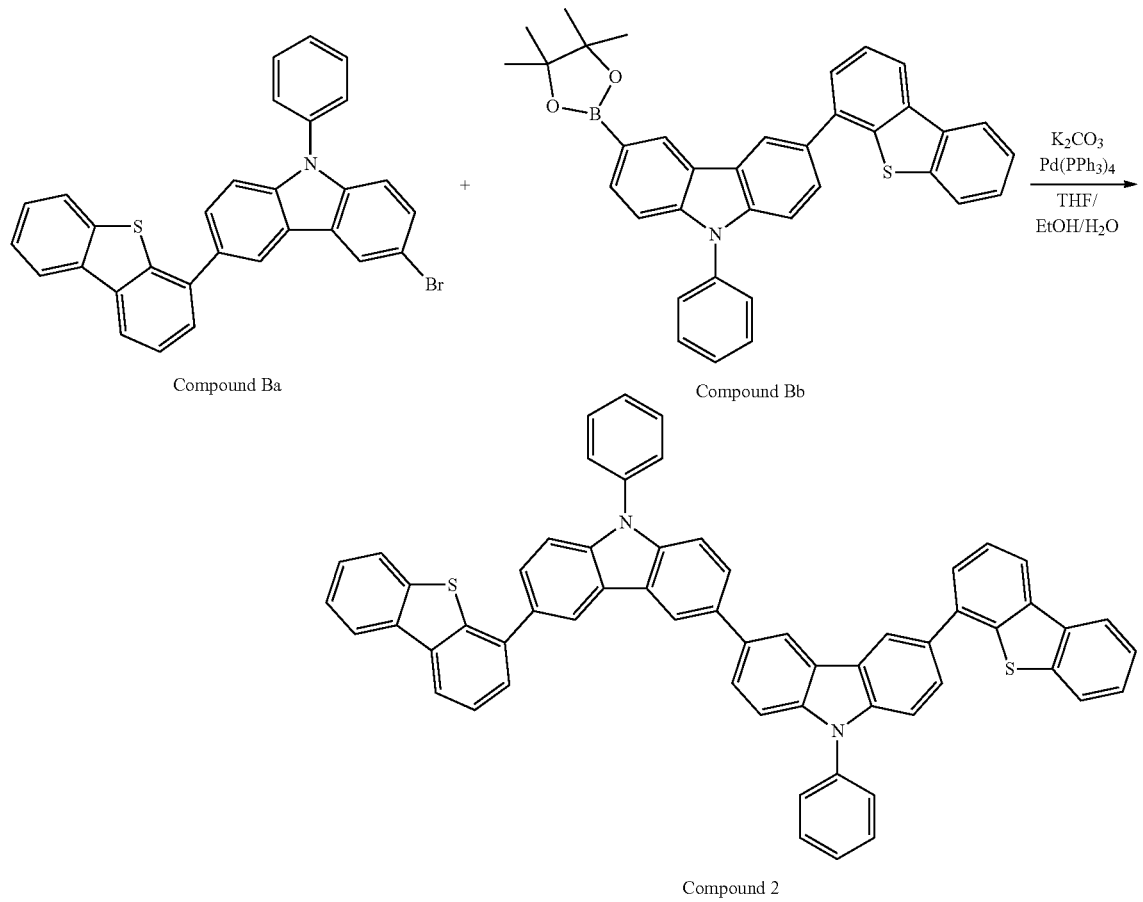

After nitrogen was charged in the 1 L three-neck round bottom flask, compound Ba (39.6 mmol, 20.0 g), compound Bb (43.6 mmol, 24.1 g), 200 mL of tetrahydrofuran (THF), and 100 mL of ethanol (EtOH) were added and agitated for 30 minutes. Further, potassium carbonate ($K_2CO_3$) (158.4 mmol, 21.9 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 1.54 mmol, 1.8 g) was added to the 1 L three-neck round bottom flask, light was blocked and reflux was performed for 5 hours. The reaction mixture was cooled, extracted and concentrated by using ethyl acetate (EA) and distilled water, dissolved in 100 mL of tetrahydrofuran (THF), and added to 1 L of methanol, followed by agitation for 30 minutes and filtration to obtain 27.6 g of compound 2 that was the light grey solid (yield 82%).

MALDI-TOF: m/z=848.2319 ($C_{60}H_{36}N_2S_2$=848.23)

Example 3

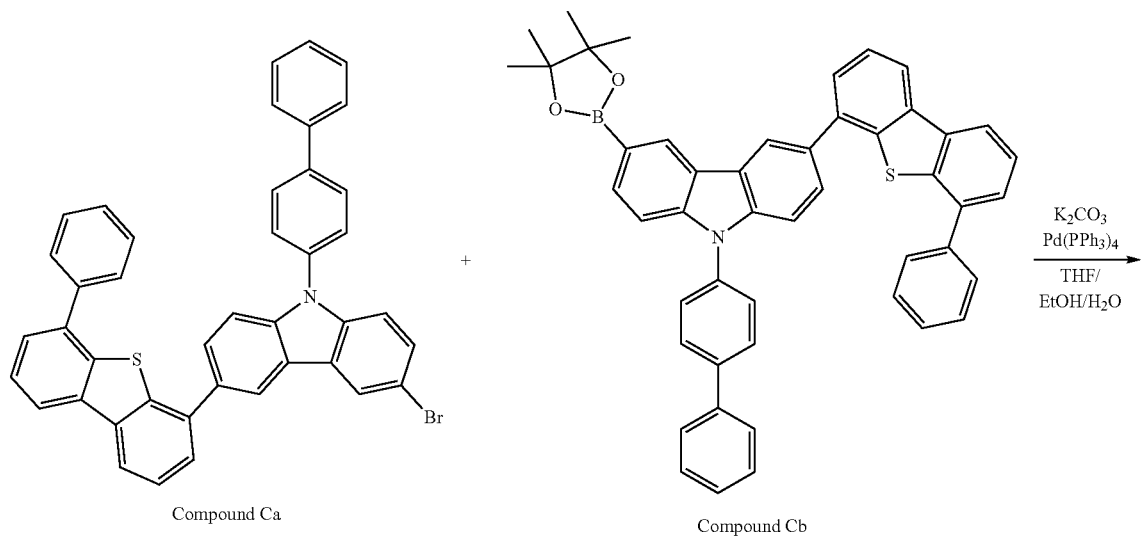

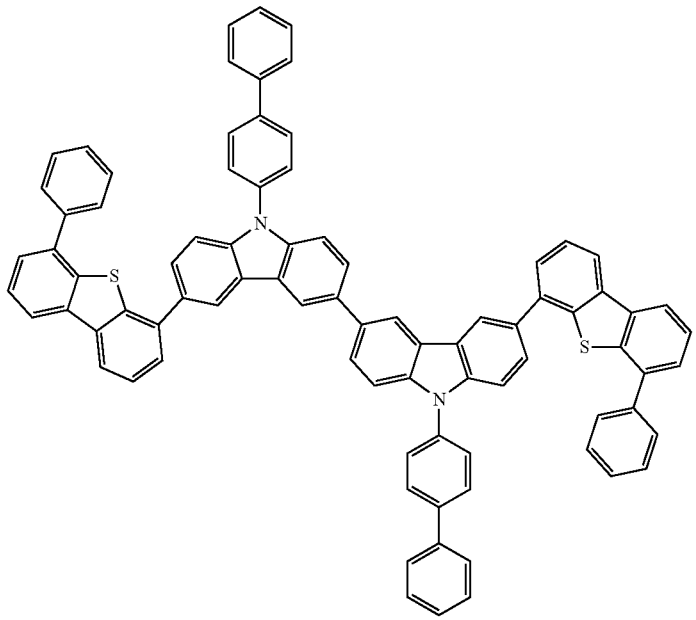

Compound 3

After nitrogen was charged in the 1 L three-neck round bottom flask, compound Ca (30.5 mmol, 20.0 g), compound Cb (33.5 mmol, 23.6 g), 200 mL of tetrahydrofuran (THF), and 100 mL of ethanol (EtOH) were added and agitated for 30 minutes. Further, potassium carbonate ($K_2CO_3$) (121.8 mmol, 16.8 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.6 mmol, 0.7 g) was added to the 1 L three-neck round bottom flask, light was blocked and reflux was performed for 8 hours. The reaction mixture was cooled, extracted and concentrated by using ethyl acetate (EA) and distilled water, dissolved in 100 mL of tetrahydrofuran (THF), and added to 1 L of methanol, followed by agitation for 1 hour and filtration to obtain 28.5 g of compound 3 that was the light grey solid (yield 81%).

MALDI-TOF: m/z=1152.5292 ($C_{84}H_{52}N_2S_2$=1152.36)

Example 4

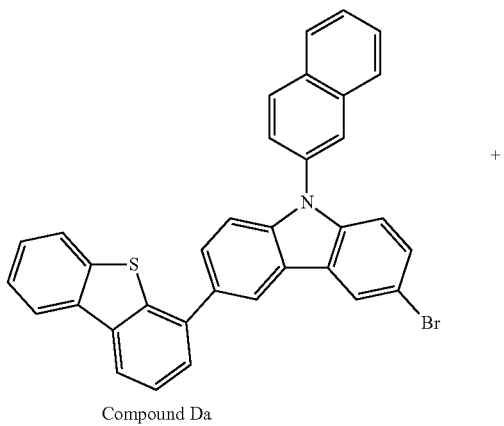

Compound Da

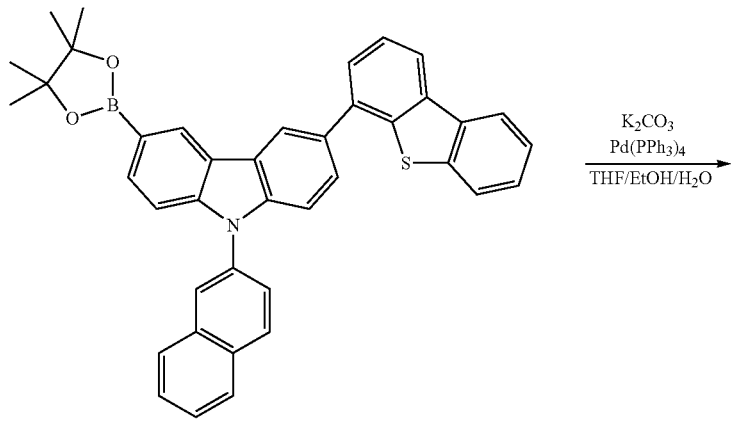

Compound Db

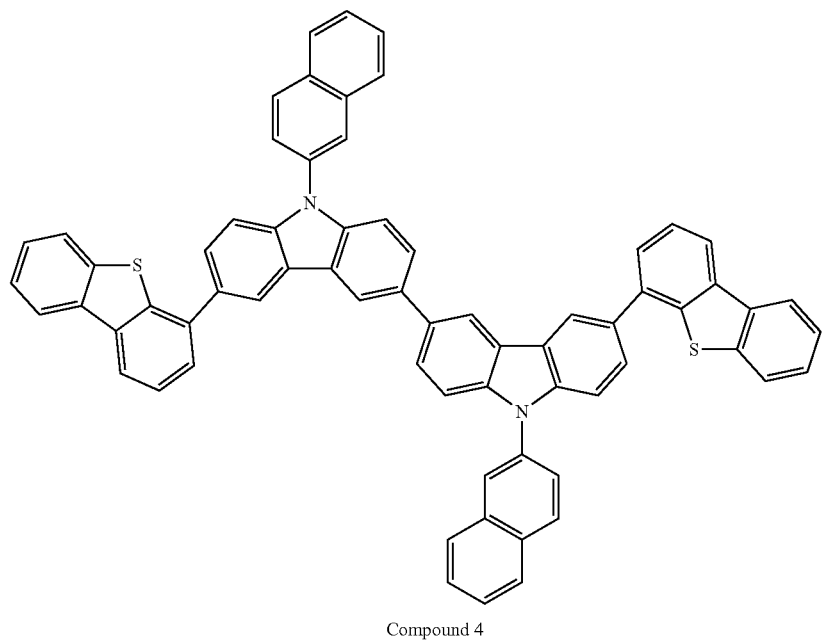

Compound 4

After nitrogen was charged in the 1 L three-neck round bottom flask, compound Da (36.1 mmol, 20.0 g), compound Db (39.7 mmol, 23.9 g), 200 mL of tetrahydrofuran (THF), and 100 mL of ethanol (EtOH) were added and agitated for 30 minutes. Further, potassium carbonate ($K_2CO_3$) (144.3 mmol, 19.9 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.7 mmol, 0.8 g) was added to the 1 L three-neck round bottom flask, light was blocked and reflux was performed for 4 hours. The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 27.5 g of compound 4 that was the light grey solid (yield 79%).

MALDI-TOF: m/z=948.5489 ($C_{68}H_{40}N_2S_2$=948.26)

Example 5

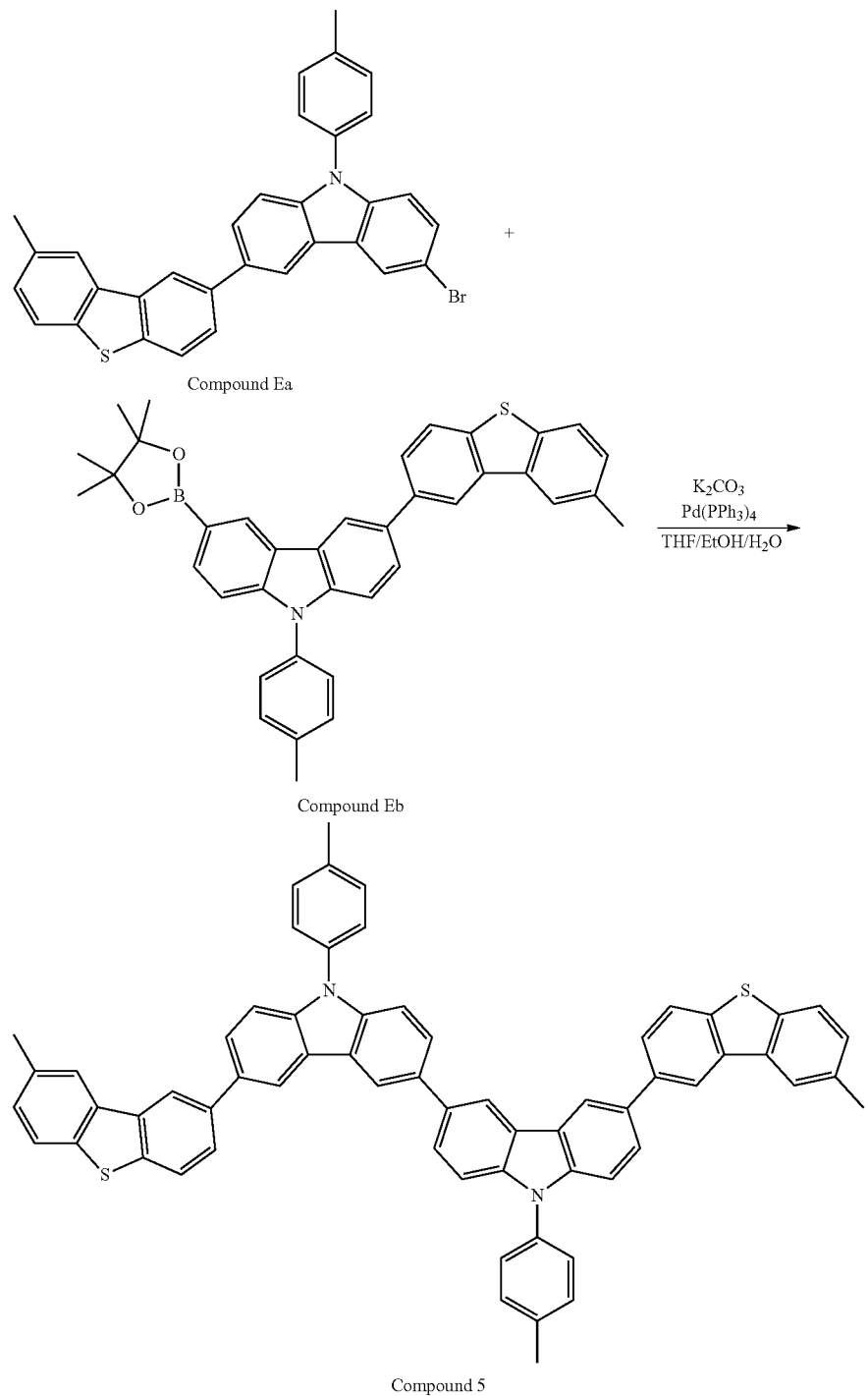

After nitrogen was charged in the 1 L three-neck round bottom flask, compound Ea (37.6 mmol, 20.0 g), compound Eb (41.3 mmol, 24.0 g), 200 mL of tetrahydrofuran (THF), and 100 mL of ethanol (EtOH) were added and agitated for 30 minutes. Further, potassium carbonate ($K_2CO_3$) (150.2 mmol, 20.8 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.8 mmol, 0.9 g) was added to the 1 L three-neck round bottom flask, light was blocked and reflux was performed for 7 hours. The reaction mixture was cooled, extracted and concentrated by using ethyl acetate (EA) and distilled water, dissolved in 100 mL of tetrahydrofuran (THF), and added to 1 L of methanol, followed by agitation for 30 minutes and filtration to obtain 28.2 g of compound 5 that was the light grey solid (yield 83%).

MALDI-TOF: m/z=904.6587 ($C_{64}H_{44}N_2S_2$=904.29)

Example 6

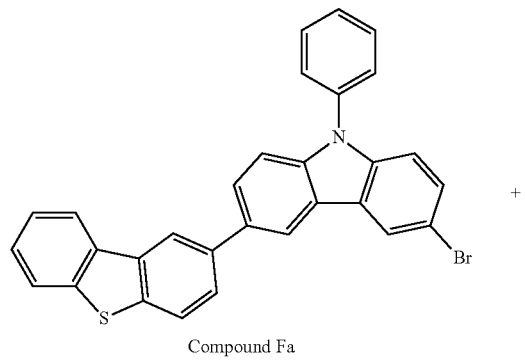

Compound Fa

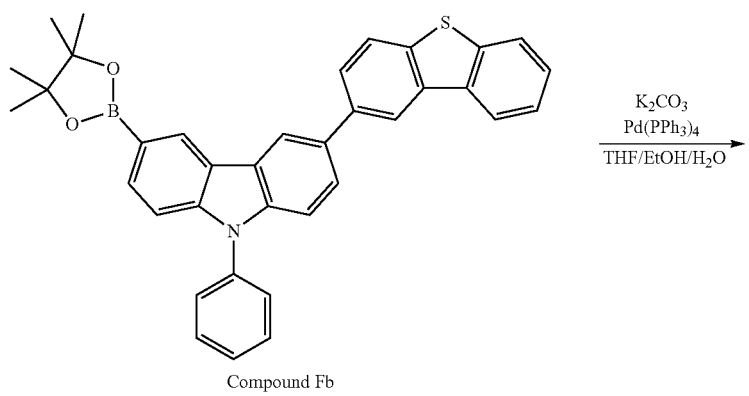

Compound Fb

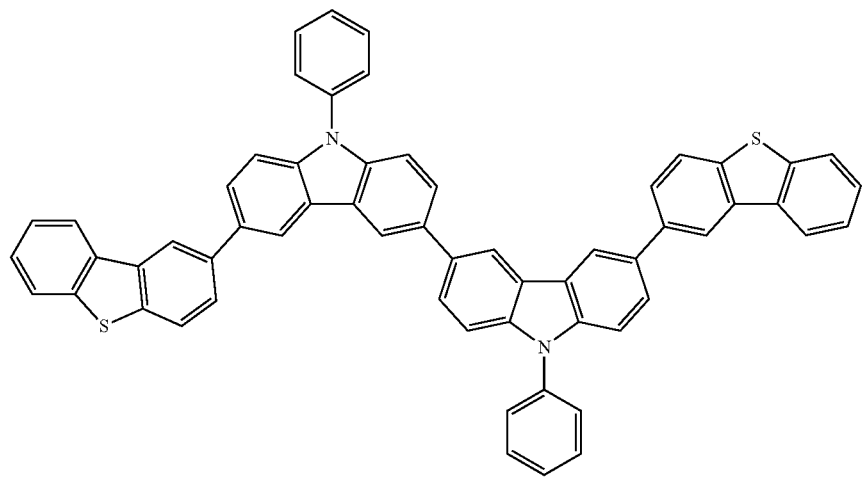

Compound 6

After nitrogen was charged in the 1 L three-neck round bottom flask, compound Fa (39.6 mmol, 20.0 g), compound Fb (43.6 mmol, 24.0 g), 200 mL of tetrahydrofuran (THF), and 100 mL of ethanol (EtOH) were added and agitated for 30 minutes. Further, potassium carbonate ($K_2CO_3$) (158.6 mmol, 21.9 g) was dissolved in 100 mL of water ($H_2O$), and then the solution was added to the 1 L three-neck round bottom flask. Subsequently, after tetrakis(triphenylphosphine)palladium (Pd(PPh$_3$)$_4$, 0.8 mmol, 0.9 g) was added to the 1 L three-neck round bottom flask, light was blocked and reflux was performed for 8 hours. The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 26.9 g of compound 6 that was the light grey solid (yield 80%).

MALDI-TOF: m/z=848.2637 ($C_{60}H_{36}N_2S_2$=848.23)

Example 7

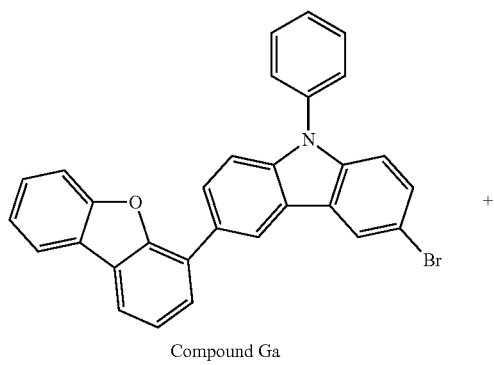

Compound Ga

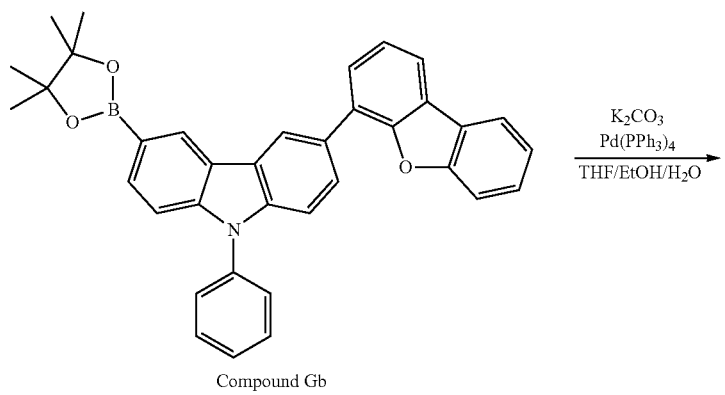

Compound Gb

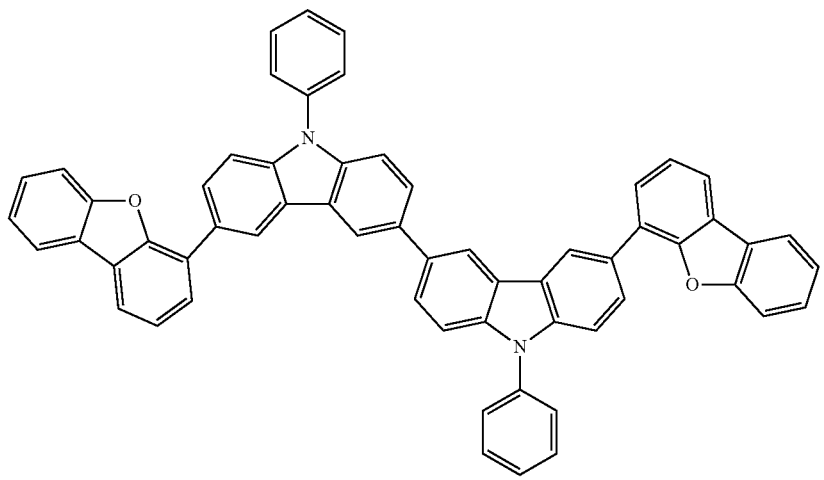

Compound 7

After nitrogen was charged in the 1 L three-neck round bottom flask, compound Ga (41.0 mmol, 20.0 g), compound Gb (45.0 mmol, 24.1 g), 200 mL of tetrahydrofuran (THF), and 100 mL of ethanol (EtOH) were added and agitated for 30 minutes. Further, potassium carbonate ($K_2CO_3$) (163.8 mmol, 22.6 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.8 mmol, 1.0 g) was added to the 1 L three-neck round bottom flask, light was blocked and reflux was performed for 5 hours. The reaction mixture was cooled, extracted and concentrated by using ethyl acetate (EA) and distilled water, dissolved in 100 mL of tetrahydrofuran (THF), and added to 1 L of methanol, followed by agitation for 40 minutes and filtration to obtain 27.8 g of compound 7 that was the light grey solid (yield 83%).

MALDI-TOF: m/z=816.6564 ($C_{60}H_{36}N_2O_2$=816.28)

Example 8

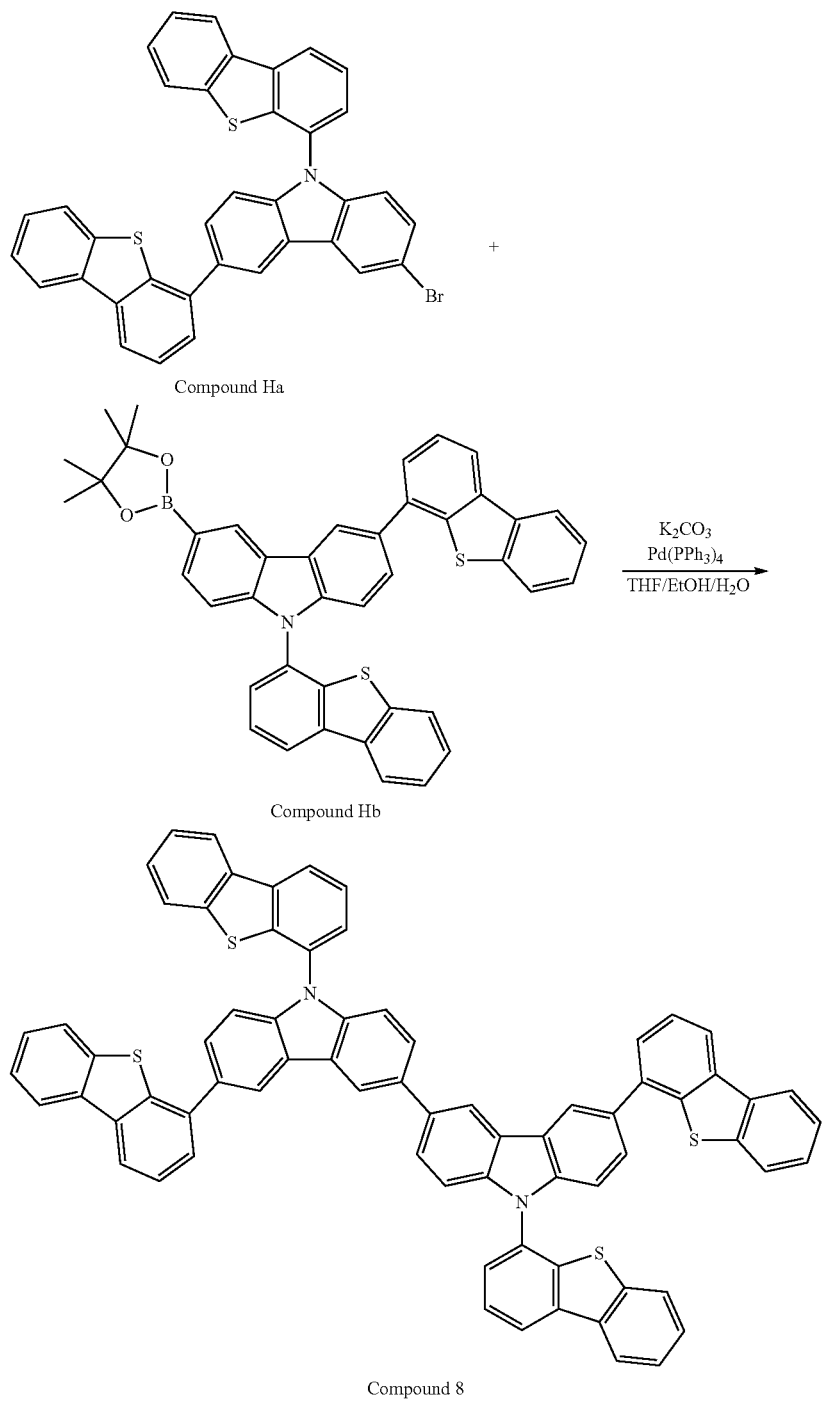

After nitrogen was charged in the 1 L three-neck round bottom flask, compound Ha (32.8 mmol, 20.0 g), compound Hb (36.0 mmol, 23.7 g), 200 mL of tetrahydrofuran (THF), and 100 mL of ethanol (EtOH) were added and agitated for 30 minutes. Further, potassium carbonate ($K_2CO_3$) (131.0 mmol, 18.1 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.7 mmol, 0.8 g) was added to the 1 L three-neck round bottom flask, light was blocked and reflux was performed for 10 hours. The reaction mixture was cooled, extracted and concentrated by using ethyl acetate (EA) and distilled water, dissolved in 100 mL of tetrahydrofuran (THF), and added to 1 L of methanol, followed by agitation for 1 hour and filtration to obtain 27.1 g of compound 8 that was the light grey solid (yield 78%).

MALDI-TOF: m/z=1060.1911 ($C_{72}H_{40}N_2S_4$=1060.21)

Example 9

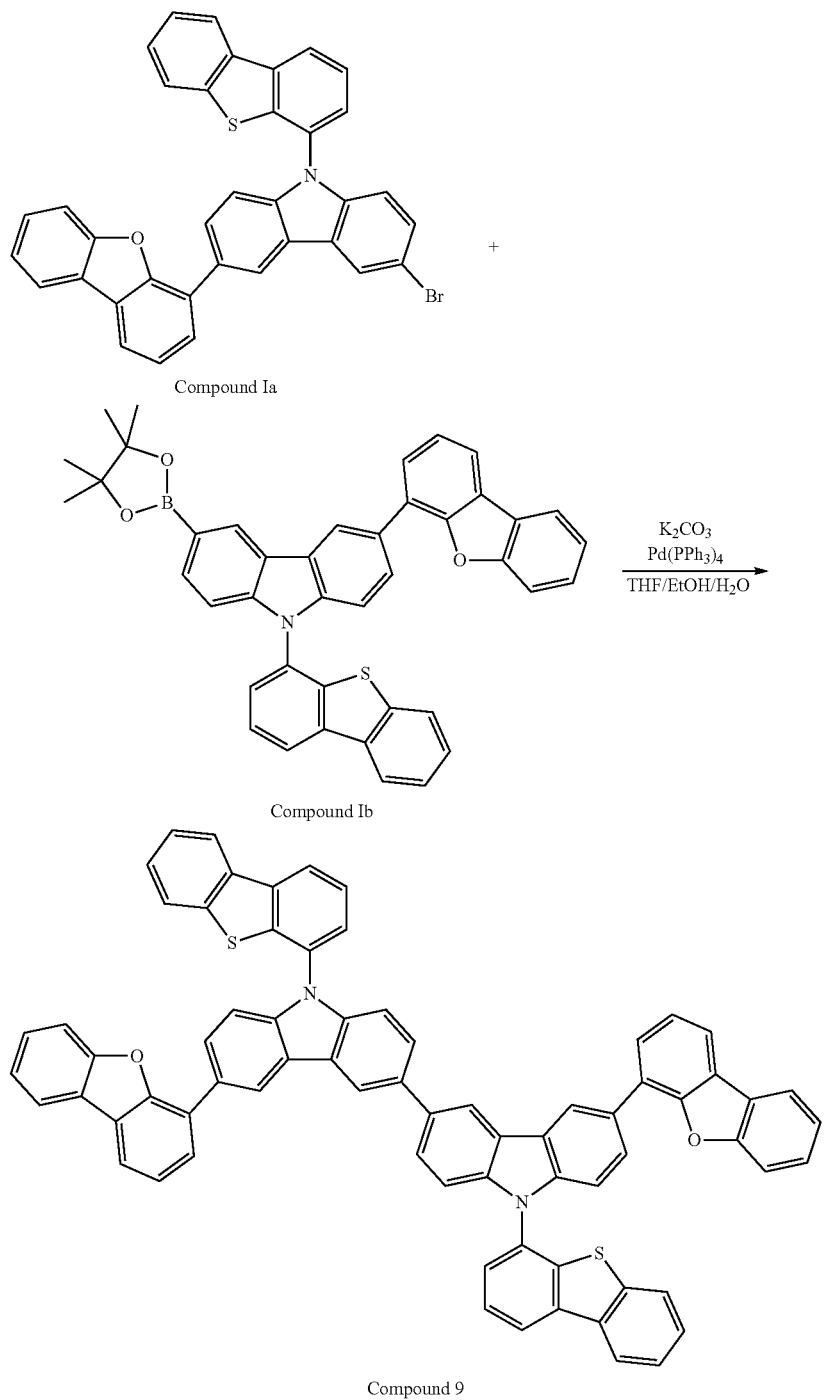

After nitrogen was charged in the 1 L three-neck round bottom flask, compound Ia (33.6 mmol, 20.0 g), compound Ib (37.0 mmol, 23.7 g), 200 mL of tetrahydrofuran (THF), and 100 mL of ethanol (EtOH) were added and agitated for 30 minutes. Further, potassium carbonate ($K_2CO_3$) (134.6 mmol, 18.6 g) was dissolved in 100 mL of water ($H_2O$), and then the solution was added to the 1 L three-neck round bottom flask. Subsequently, after tetrakis(triphenylphosphine)palladium (Pd(PPh$_3$)$_4$, 0.7 mmol, 0.8 g) was added to the 1 L three-neck round bottom flask, light was blocked and reflux was performed for 8 hours. The reaction mixture was cooled, extracted and concentrated by using ethyl acetate (EA) and distilled water, dissolved in 100 mL of tetrahydrofuran (THF), and added to 1 L of methanol, followed by agitation for 30 minutes and filtration to obtain 27.7 g of compound 9 that was the light grey solid (yield 80%).

MALDI-TOF: m/z=1029.2425 ($C_{72}H_{40}N_2O_2S_2$=1028.25)

Example 10

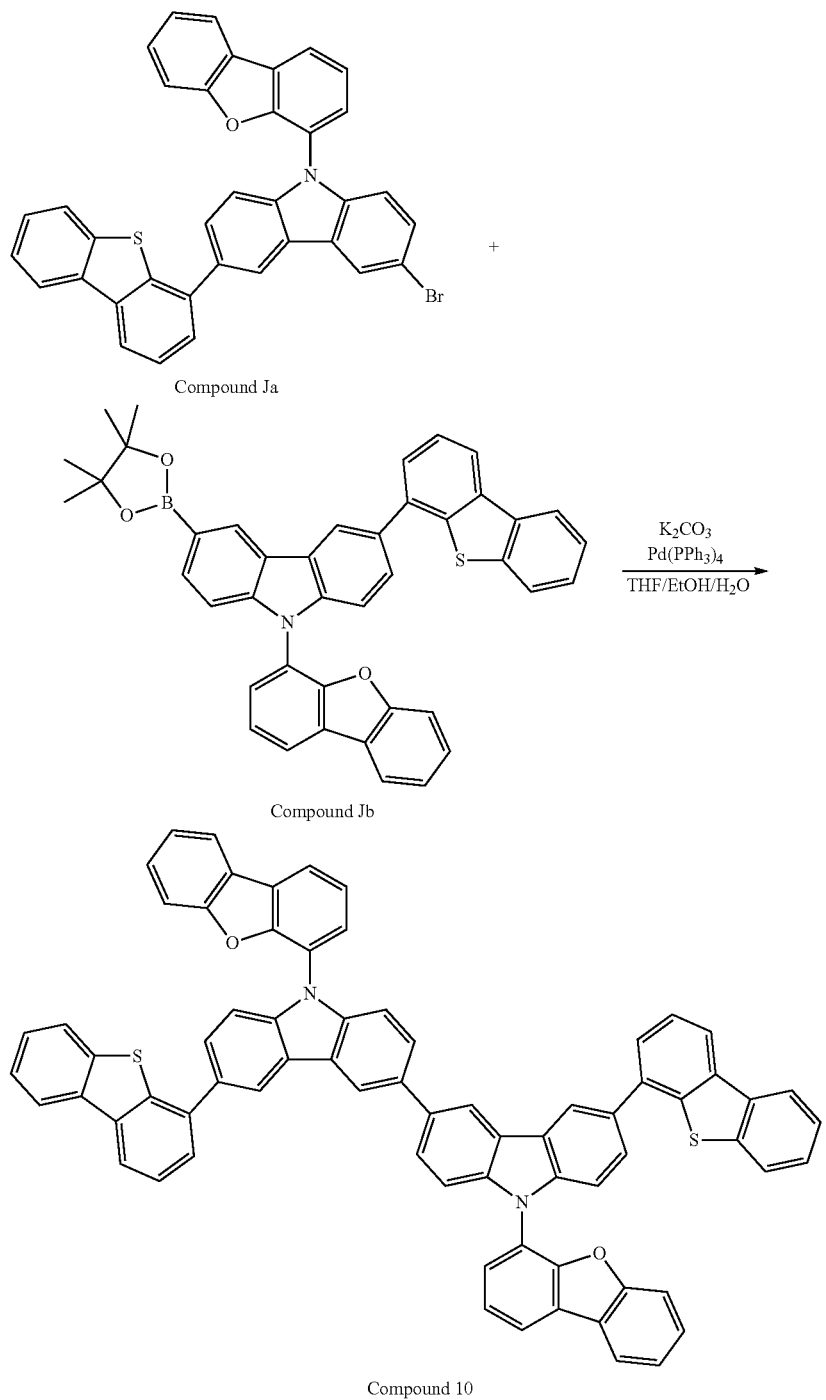

After nitrogen was charged in the 1 L three-neck round bottom flask, compound Ja (33.6 mmol, 20.0 g), compound Jb (37.0 mmol, 23.7 g), 200 mL of tetrahydrofuran (THF), and 100 mL of ethanol (EtOH) were added and agitated for 30 minutes. Further, potassium carbonate ($K_2CO_3$) (134.6 mmol, 18.6 g) was dissolved in 100 mL of water ($H_2O$), and then the solution was added to the 1 L three-neck round bottom flask. Subsequently, after tetrakis(triphenylphosphine)palladium (Pd(PPh$_3$)$_4$, 0.7 mmol, 0.8 g) was added to the 1 L three-neck round bottom flask, light was blocked and reflux was performed for 9 hours. The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 28.0 g of compound 10 that was the light grey solid (yield 81%).

MALDI-TOF: m/z=1029.3885 ($C_{72}H_{40}N_2O_2S_2$= 1028.25)

Example 11

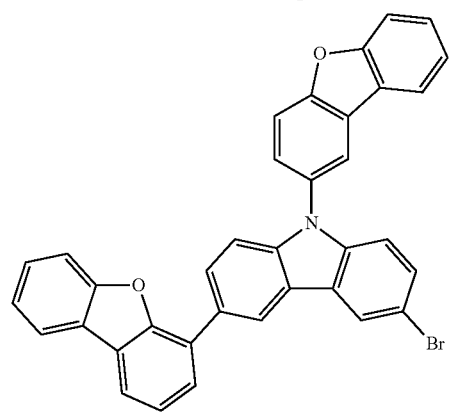

Compound Ka

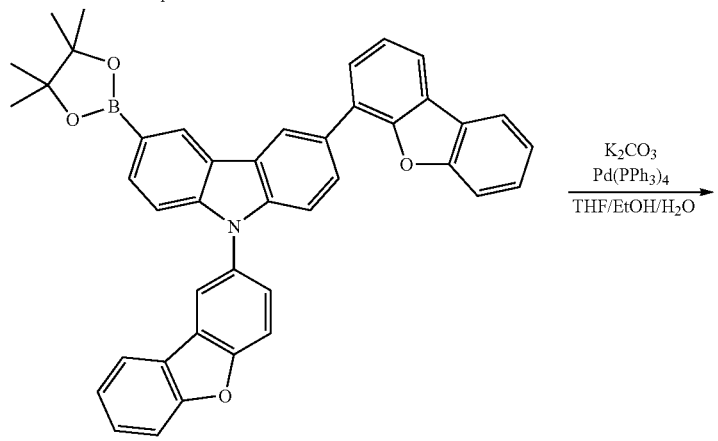

Compound Kb

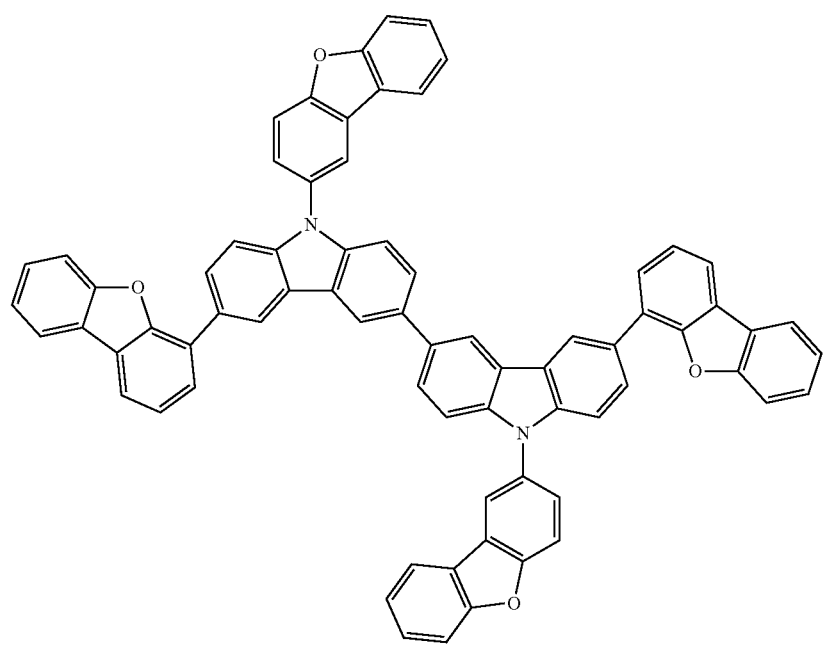

Compound 11

After nitrogen was charged in the 1 L three-neck round bottom flask, compound Ka (34.6 mmol, 20.0 g), compound Kb (38.0 mmol, 23.8 g), 200 mL of tetrahydrofuran (THF), and 100 mL of ethanol (EtOH) were added and agitated for 30 minutes. Further, potassium carbonate ($K_2CO_3$) (138.3 mmol, 19.1 g) was dissolved in 100 mL of water ($H_2O$), and then the solution was added to the 1 L three-neck round bottom flask. Subsequently, after tetrakis(triphenylphosphine)palladium (Pd(PPh$_3$)$_4$, 0.7 mmol, 0.8 g) was added to the 1 L three-neck round bottom flask, light was blocked and reflux was performed for 8 hours. The reaction mixture was cooled, extracted and concentrated by using ethyl acetate (EA) and distilled water, dissolved in 100 mL of tetrahydrofuran (THF), and added to 1 L of methanol, followed by agitation for 30 minutes and filtration to obtain 28.3 g of compound 11 that was the light grey solid (yield 82%).

MALDI-TOF: m/z=996.3124 (C$_{72}$H$_{40}$N$_2$O$_4$=996.30)

Example 12

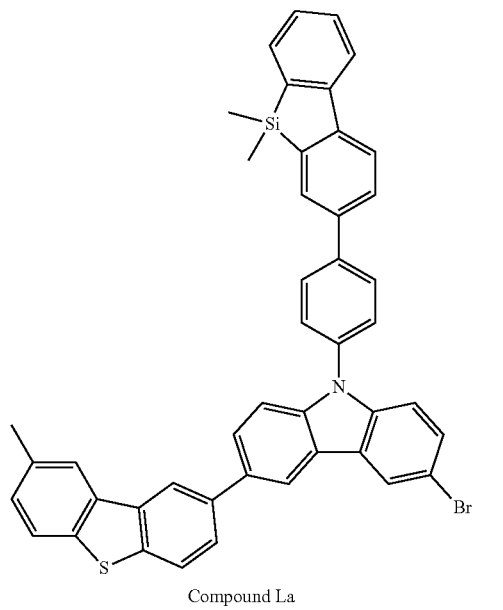

Compound La

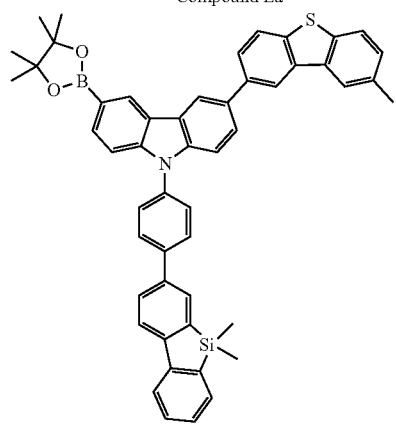

Compound Lb

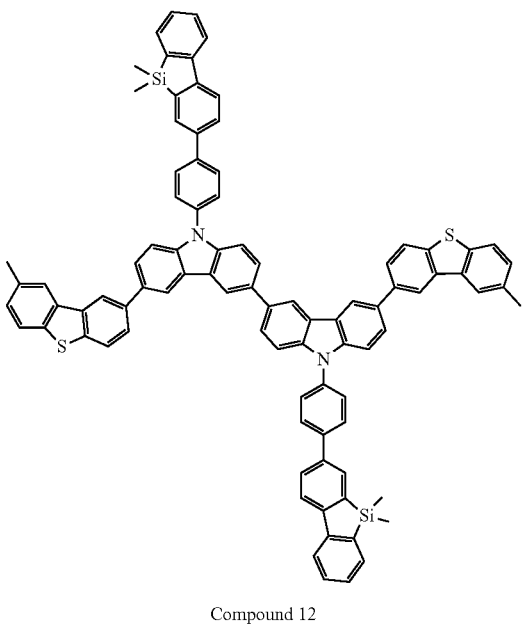 [SMILES: Cc1ccc2sc3ccc(-c4ccc5c(c4)c4cc(-c6ccc7c(c6)c6cc(-c8ccc9sc%10ccc(C)cc%10c9c8)ccc6n7-c6ccc(-c7ccc8c(c7)[Si](C)(C)c7ccccc7-8)cc6)ccc4n5-c4ccc(-c5ccc6c(c5)[Si](C)(C)c5ccccc5-6)cc4)cc3c2c1]

Compound 12

After nitrogen was charged in the 1 L three-neck round bottom flask, compound La (27.5 mmol, 20.0 g), compound Lb (30.3 mmol, 23.4 g), 200 mL of tetrahydrofuran (THF), and 100 mL of ethanol (EtOH) were added and agitated for 30 minutes. Further, potassium carbonate (K$_2$CO$_3$) (110.1 mmol, 15.2 g) was dissolved in 100 mL of water (H$_2$O), and then the solution was added to the 1 L three-neck round bottom flask. Subsequently, after tetrakis(triphenylphosphine)palladium (Pd(PPh$_3$)$_4$, 0.7 mmol, 0.8 g) was added to the 1 L three-neck round bottom flask, light was blocked and reflux was performed for 8 hours. The reaction mixture was cooled, extracted and concentrated by using ethyl acetate (EA) and distilled water, dissolved in 100 mL of tetrahydrofuran (THF), and added to 1 L of methanol, followed by agitation for 40 minutes and filtration to obtain 27.8 g of compound 12 that was the light grey solid (yield 78%).

MALDI-TOF: m/z=1292.4312 (C$_{90}$H$_{64}$N$_2$S$_2$Si$_2$=1292.40)

Example 13

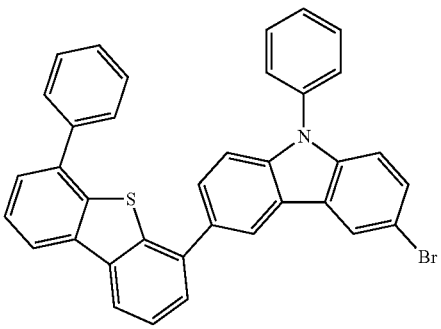

Compound Ma

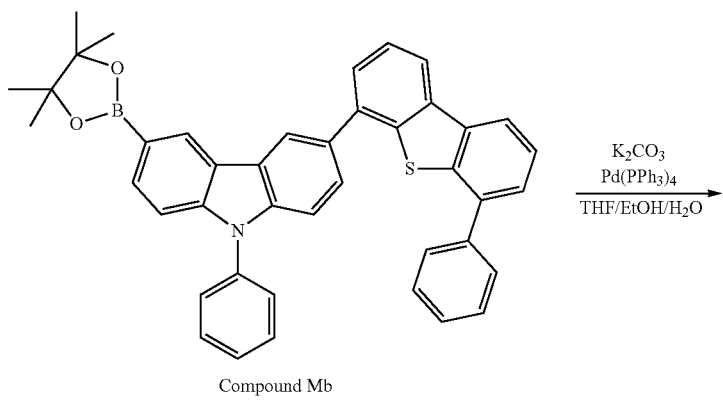

Compound Mb

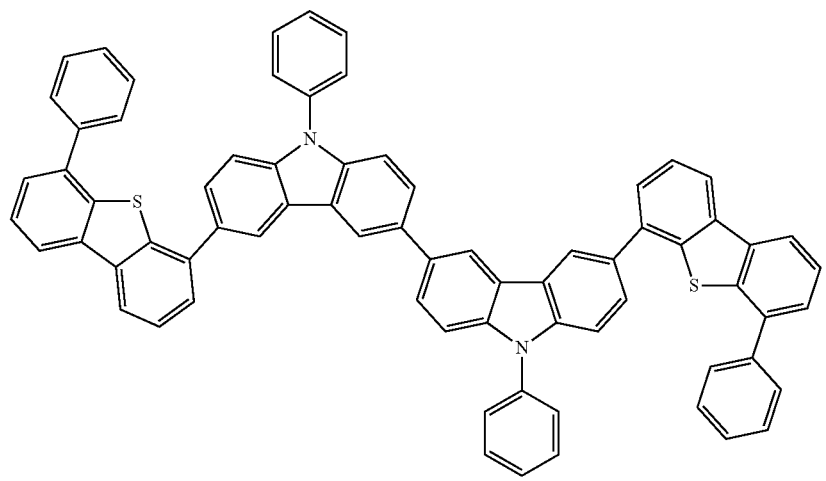

Compound 13

After nitrogen was charged in the 1 L three-neck round bottom flask, compound Ma (34.5 mmol, 20.0 g), compound Mb (37.9 mmol, 23.8 g), 200 mL of tetrahydrofuran (THF), and 100 mL of ethanol (EtOH) were added and agitated for 30 minutes. Further, potassium carbonate ($K_2CO_3$) (137.8 mmol, 19.0 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.7 mmol, 0.8 g) was added to the 1 L three-neck round bottom flask, light was blocked and reflux was performed for 6 hours. The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 27.9 g of compound 13 that was the light grey solid (yield 81%).

MALDI-TOF: m/z=1000.6598 ($C_{72}H_{44}N_2S_2$=1000.29)

Example 14

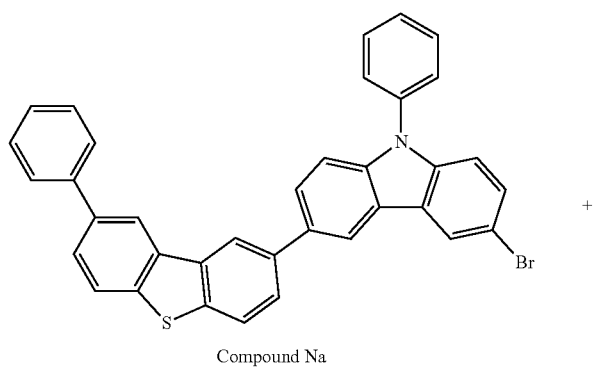

Compound Na

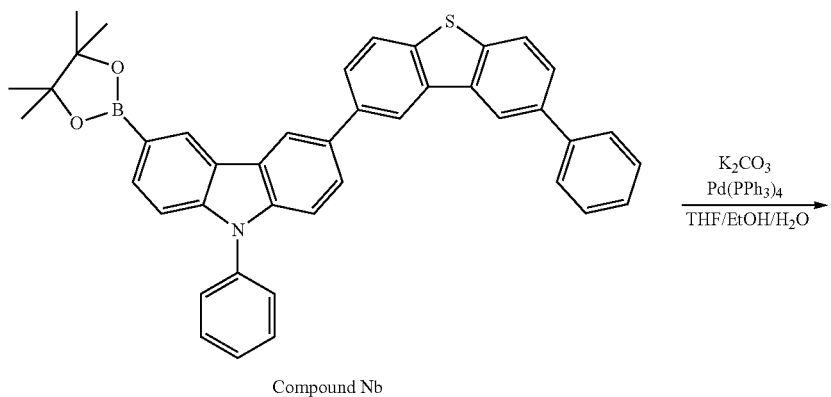

Compound Nb

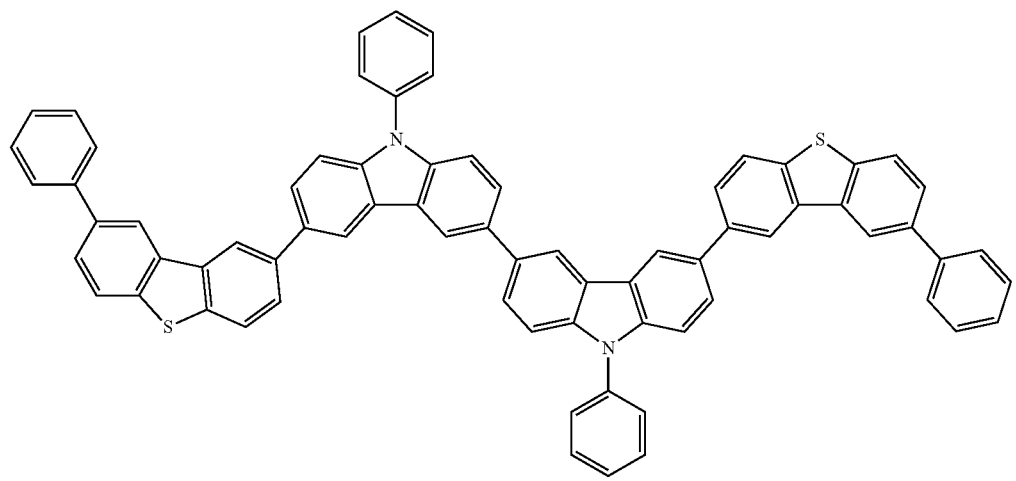

Compound 14

After nitrogen was charged in the 1 L three-neck round bottom flask, compound Na (34.5 mmol, 20.0 g), compound Nb (37.9 mmol, 23.8 g), 200 mL of tetrahydrofuran (THF), and 100 mL of ethanol (EtOH) were added and agitated for 30 minutes. Further, potassium carbonate ($K_2CO_3$) (137.8 mmol, 19.0 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 0.7 mmol, 0.8 g) was added to the 1 L three-neck round bottom flask, light was blocked and reflux was performed for 6 hours. The reaction mixture was cooled, extracted and concentrated by using ethyl acetate (EA) and distilled water, dissolved in 100 mL of tetrahydrofuran (THF), and added to 1 L of methanol, followed by agitation for 30 minutes and filtration to obtain 27.6 g of compound 14 that was the light grey solid (yield 80%).

MALDI-TOF: m/z=1000.5798 ($C_{72}H_{44}N_2S_2$=1000.29)

Comparative Example 1

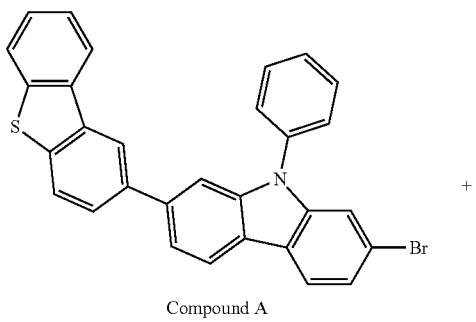

Compound A

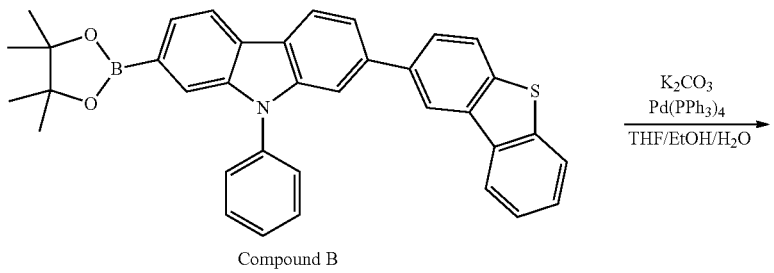

Compound B

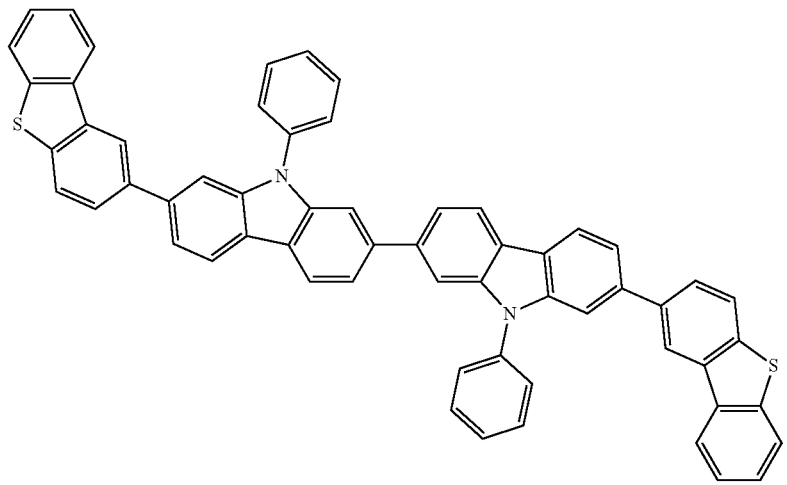

Comparative Compound 1

After nitrogen was charged in the 1 L three-neck round bottom flask, compound A (67.4 mmol, 34.0 g), compound B (74.1 mmol, 40.9 g), 340 mL of tetrahydrofuran (THF), and 170 mL of ethanol (EtOH) were added and agitated for 30 minutes. Further, potassium carbonate ($K_2CO_3$) (269.6 mmol, 37.3 g) was dissolved in 170 mL of water ($H_2O$), and then the solution was added to the 1 L three-neck round bottom flask. Subsequently, after tetrakis(triphenylphosphine)palladium ($Pd(PPh_3)_4$, 2.7 mmol, 3.1 g) was added to the 1 L three-neck round bottom flask, light was blocked and reflux was performed for 6 hours. The reaction mixture was cooled, extracted and concentrated by using ethyl acetate (EA) and distilled water, dissolved in 170 mL of tetrahydrofuran (THF), and added to 1,700 mL of methanol, followed by agitation for 20 minutes and filtration to obtain 40.1 g of comparative compound 1 that was the light grey solid (yield 70%).

MALDI-TOF: m/z=848.2359 ($C_{60}H_{36}N_2S_2$=848.23)

Comparative Example 2

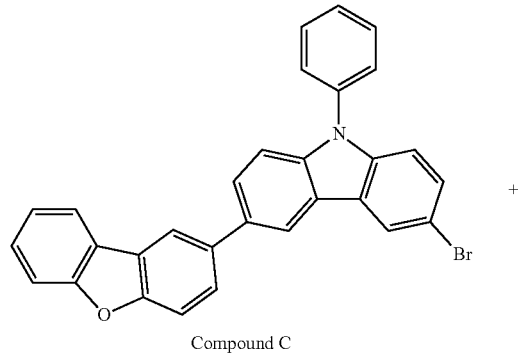

Compound C

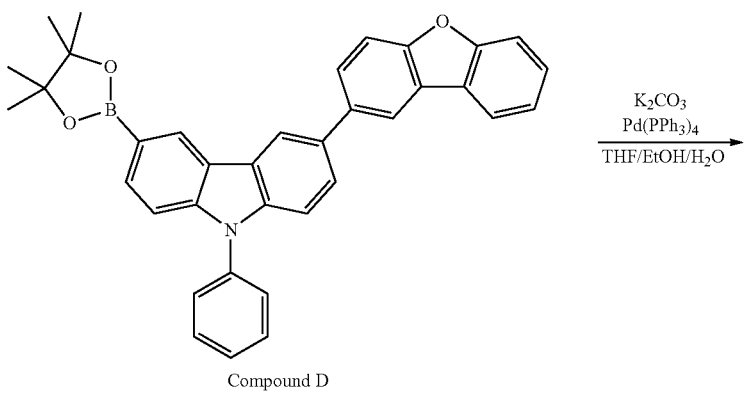

Compound D

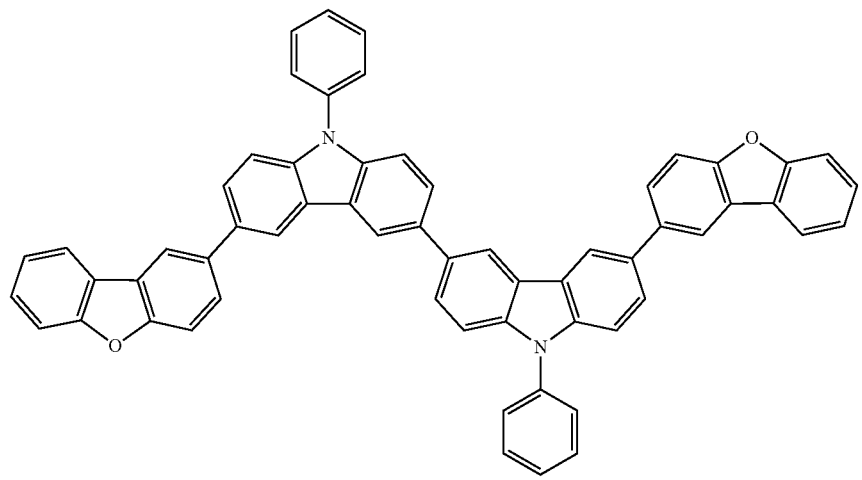

Comparative Compound 2

After nitrogen was charged in the 1 L three-neck round bottom flask, compound C (41.0 mmol, 20.0 g), compound D (45.0 mmol, 24.1 g), 200 mL of tetrahydrofuran (THF), and 100 mL of ethanol (EtOH) were added and agitated for 30 minutes. Further, potassium carbonate ($K_2CO_3$) (163.8 mmol, 22.6 g) was dissolved in 100 mL of water ($H_2O$), and then the solution was added to the 1 L three-neck round bottom flask. Subsequently, after tetrakis(triphenylphosphine)palladium ($Pd(PPh_3)_4$, 1.6 mmol, 1.9 g) was added to the 1 L three-neck round bottom flask, light was blocked and reflux was performed for 6 hours. The reaction mixture was cooled, extracted and concentrated by using ethyl acetate (EA) and distilled water, dissolved in 100 mL of tetrahydrofuran (THF), and added to 1000 mL of methanol, followed by agitation for 20 minutes and filtration to obtain 23.4 g of comparative compound 2 that was the light grey solid (yield 70%).

MALDI-TOF: m/z=816.2810 ($C_{60}H_{36}N_2O_2$=816.28)

Comparative Example 3

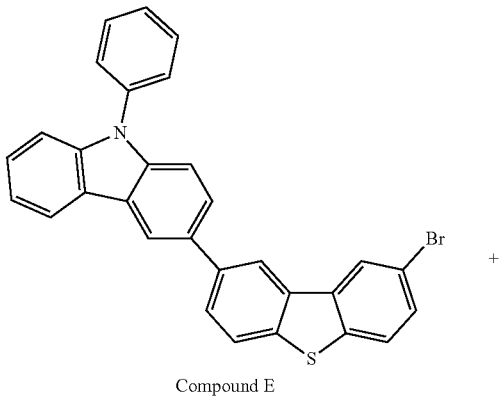

Compound E

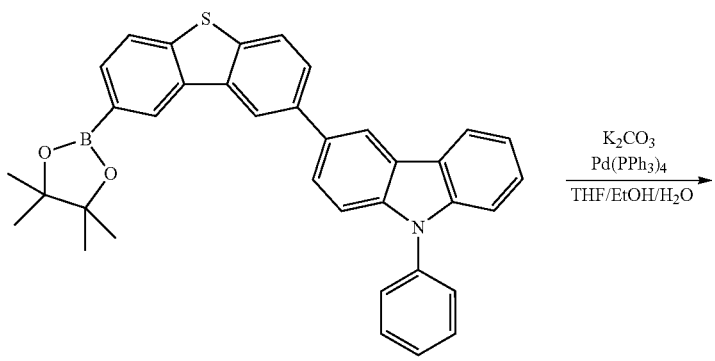

Compound F

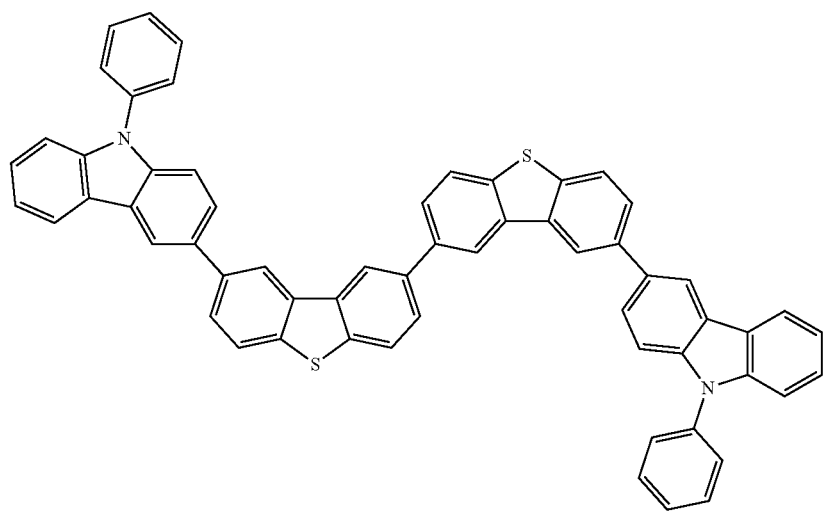

Comparative Compound 3

After nitrogen was charged in the 1 L three-neck round bottom flask, compound E (15.9 mmol, 8.0 g), compound F (17.4 mmol, 9.6 g), 80 mL of tetrahydrofuran (THF), and 40 mL of ethanol (EtOH) were added and agitated for 30 minutes. Further, potassium carbonate ($K_2CO_3$) (63.4 mmol, 8.8 g) was dissolved in 40 mL of water ($H_2O$), and then the solution was added to the 1 L three-neck round bottom flask. Subsequently, after tetrakis(triphenylphosphine)palladium ($Pd(PPh_3)_4$, 0.6 mmol, 0.7 g) was added to the 1 L three-neck round bottom flask, light was blocked and reflux was performed for 6 hours. The reaction mixture was cooled, extracted and concentrated by using ethyl acetate (EA) and distilled water, dissolved in 40 mL of tetrahydrofuran (THF), and added to 400 mL of methanol, followed by agitation for 20 minutes and filtration to obtain 11.4 g of comparative compound 3 that was the light grey solid (yield 85%).

MALDI-TOF: m/z=848.2353 ($C_{60}H_{36}N_2S_2$=848.23)

Comparative Example 4

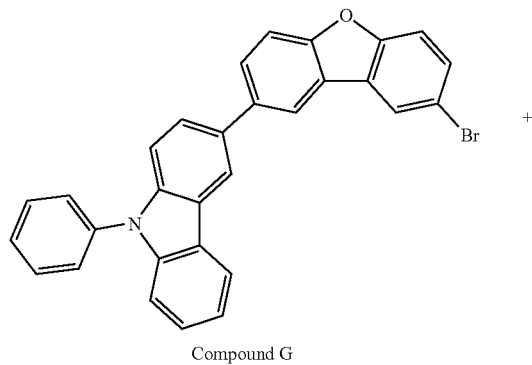

Compound G

-continued

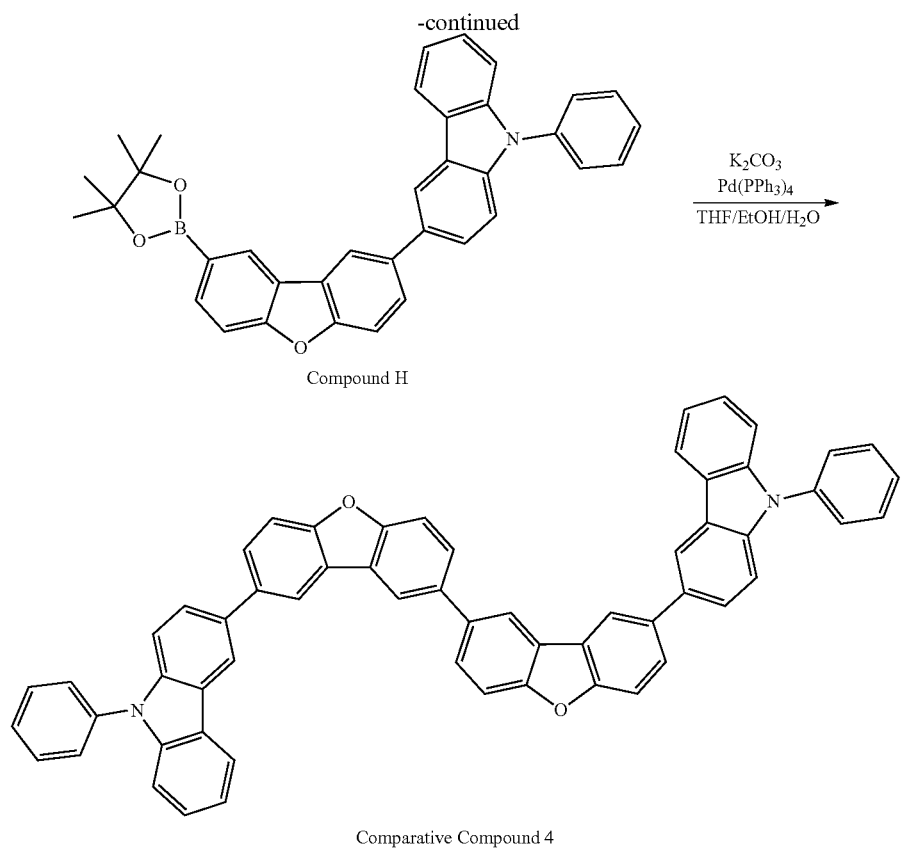

Compound H

Comparative Compound 4

After nitrogen was charged in the 1 L three-neck round bottom flask, compound G (61.4 mmol, 30.0 g), compound H (67.6 mmol, 36.2 g), 300 mL of tetrahydrofuran (THF), and 150 mL of ethanol (EtOH) were added and agitated for 30 minutes. Further, potassium carbonate ($K_2CO_3$) (245.7 mmol, 34.0 g) was dissolved in 150 mL of water ($H_2O$), and then the solution was added to the 1 L three-neck round bottom flask. Subsequently, after tetrakis(triphenylphosphine)palladium ($Pd(PPh_3)_4$, 2.5 mmol, 2.8 g) was added to the 1 L three-neck round bottom flask, light was blocked and reflux was performed for 6 hours. The reaction mixture was cooled, extracted and concentrated by using ethyl acetate (EA) and distilled water, dissolved in 150 mL of tetrahydrofuran (THF), and added to 1,500 mL of methanol, followed by agitation for 20 minutes and filtration to obtain 35.1 g of comparative compound 4 that was the light grey solid (yield 70%).

MALDI-TOF: m/z=816.2834 ($C_{60}H_{36}N_2O_2$=816.28)

Comparative Example 5

The following compound was prepared according to the synthesis method disclosed in Japanese Patent Application Laid-Open No. 2012-175025.

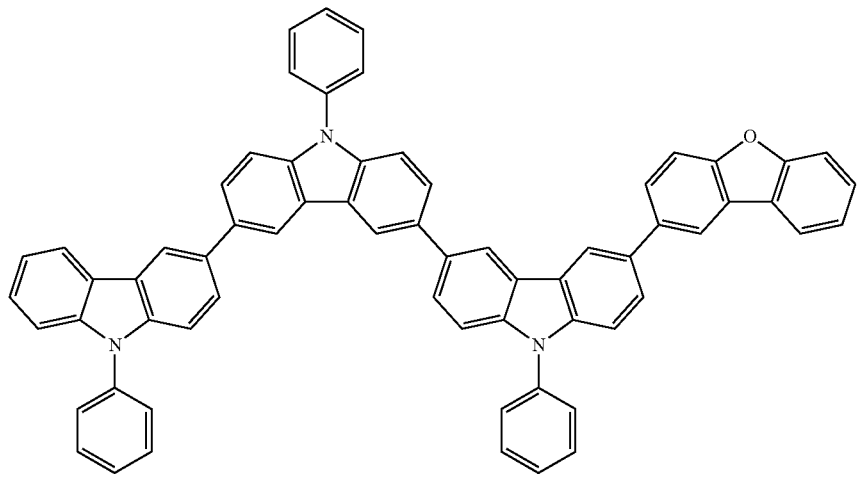 [SMILES: c1ccc(-n2c3ccccc3c3cc(-c4ccc5c(c4)c4cc(-c6ccc7c(c6)c6cc(-c8ccc9oc%10ccccc%10c9c8)ccc6n7-c6ccccc6)ccc4n5-c4ccccc4)ccc32)cc1]

Comparative Example 6

The following compound was prepared according to the synthesis method disclosed in PCT Publication No. WO12/008281.

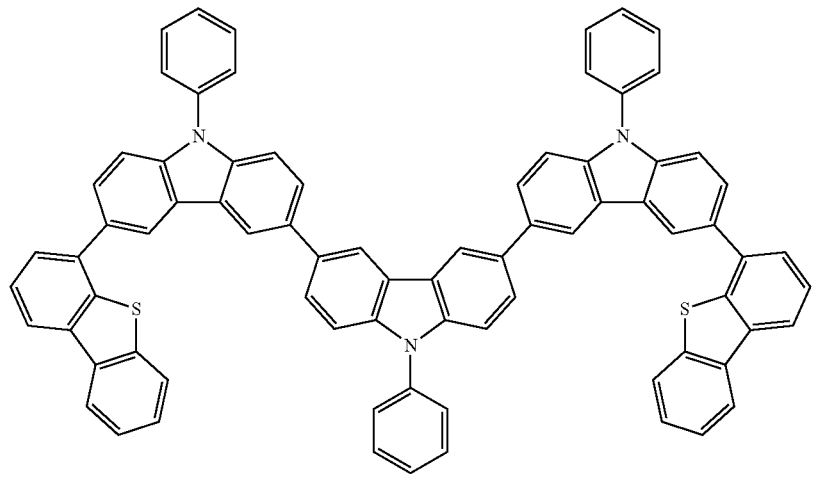 [SMILES: c1ccc(-n2c3ccc(-c4ccc5c(c4)c4cc(-c6cccc7c6sc6ccccc67)ccc4n5-c4ccccc4)cc3c3cc(-c4ccc5c(c4)c4cc(-c6cccc7c6sc6ccccc67)ccc4n5-c4ccccc4)ccc32)cc1]

Comparative Example 7

The following compound was prepared according to the synthesis method disclosed in Japanese Patent Application Laid-Open No. 2012-049518.

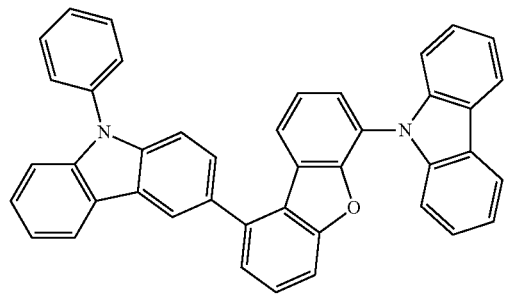 [SMILES: c1ccc(-n2c3ccccc3c3cc(-c4cccc5oc6c(-n7c8ccccc8c8ccccc87)cccc6c45)ccc32)cc1]

Comparative Example 8

The following compound was prepared according to the synthesis method disclosed in Japanese Patent Application Laid-Open No. 2012-049518.

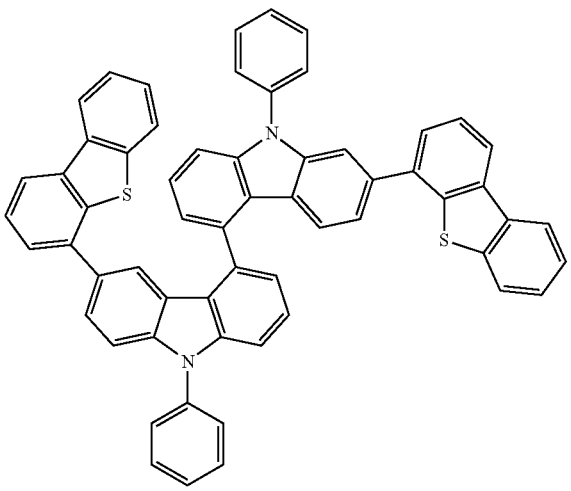 [SMILES: c1ccc(-n2c3ccc(-c4cccc5c4sc4ccccc45)cc3c3c(-c4cccc5c4c4ccc(-c6cccc7c6sc6ccccc67)cc4n5-c4ccccc4)cccc32)cc1]

Comparative Examples 9 to 12

The compounds having the structures of the following Chemical Formulas a, b, c, and d were commercially obtained or manufactured to be used as Comparative Examples 9 to 12.

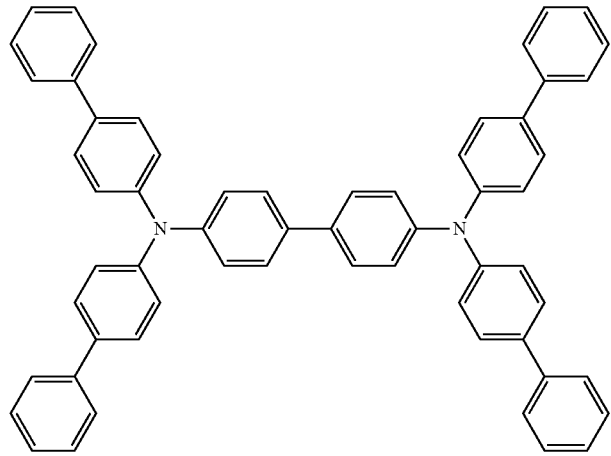
[Chemical Formula a]
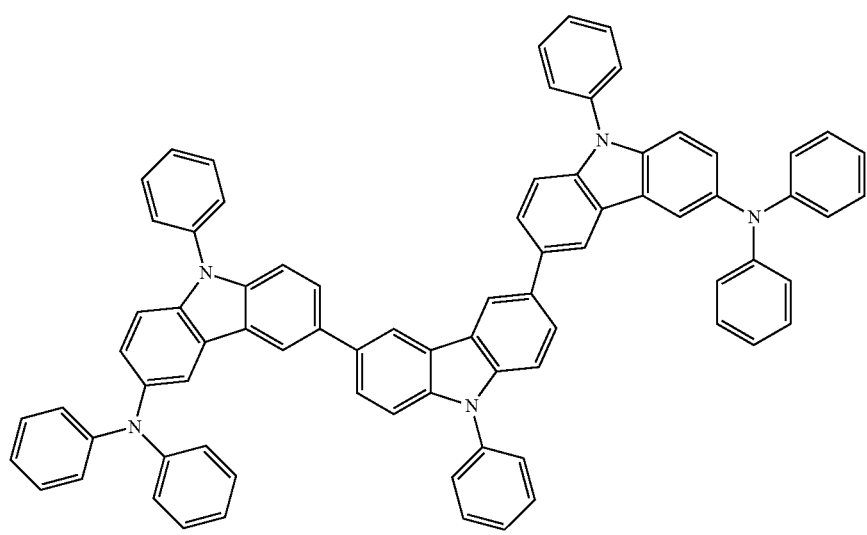
[Chemical Formula b]
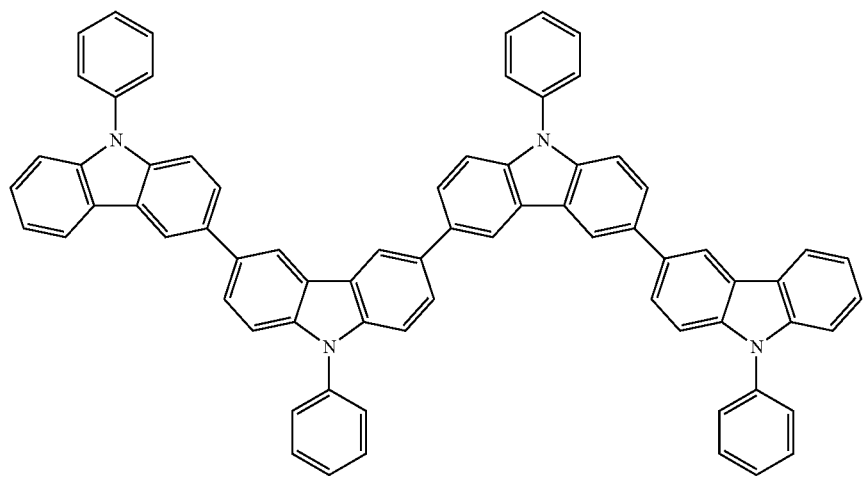
[Chemical Formula c]

-continued

[Chemical Formula d]

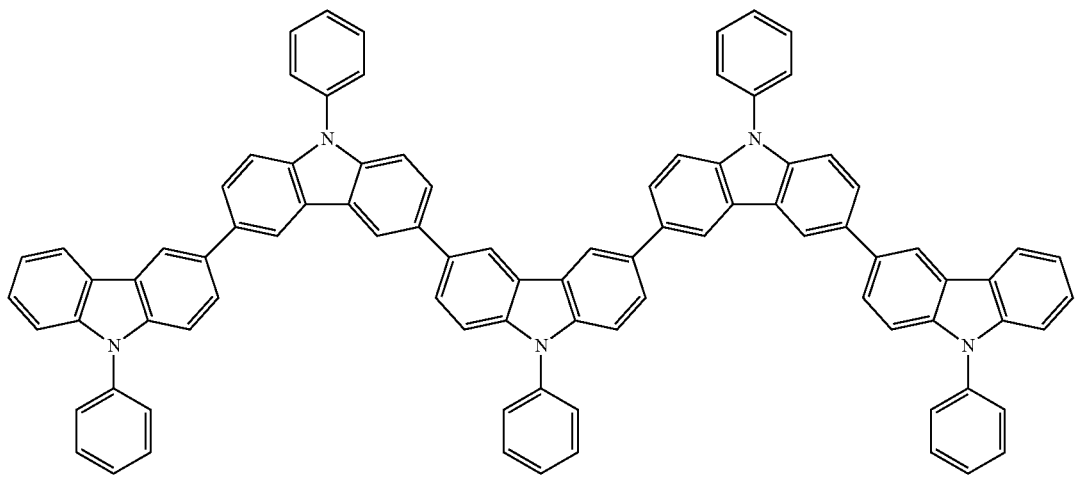

Manufacturing of Light Emitting Diodes A-1 to A-10

On the first electrode formed of indium tin oxide (ITO), the compound according to Example 1 as the host material was evaporated at the rate of 1 Å/sec, and simultaneously, the P-type dopant (HAT-CN) represented by the following Chemical Formula 13 was co-evaporated at the ratio of about 5 parts by weight based on 100 parts by weight of the host material to form the first layer having the thickness of 100 Å. On the first layer, the compound according to Example 1 was evaporated in the thickness of 300 Å to form the second layer.

On the second layer, mCBP represented by the following Chemical Formula 14 and Ir(ppy)$_3$ represented by Chemical Formula 15 were co-evaporated at the weight ratio of 100:9 to form the light emitting layer having the thickness of about 300 Å, and on the light emitting layer, mCBP was evaporated again in the thickness of about 50 Å to form the blocking layer.

Then, on the blocking layer, BPhen represented by the following Chemical Formula 16 and Alq$_3$ represented by the following Chemical Formula 17 were co-evaporated at the weight ratio of 50:50 to form the electron transport layer having the thickness of about 400 Å. Subsequently, on the electron transport layer, the electron injection layer having the thickness of about 10 Å was formed by using Liq represented by the following Chemical Formula 18.

On the electron injection layer, the second electrode using the aluminum thin film having the thickness of 1,000 Å was formed.

[Chemical Formula 13]

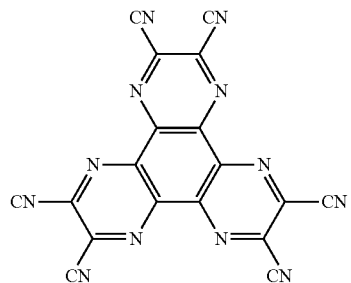

-continued

[Chemical Formula 14]

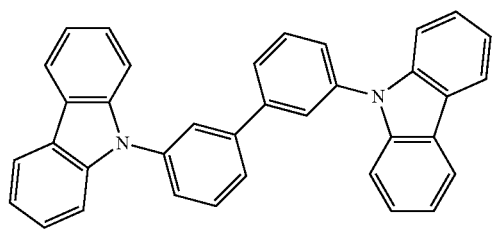

[Chemical Formula 15]

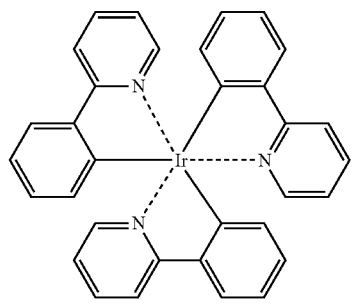

[Chemical Formula 16]

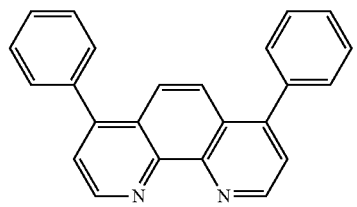

[Chemical Formula 17]

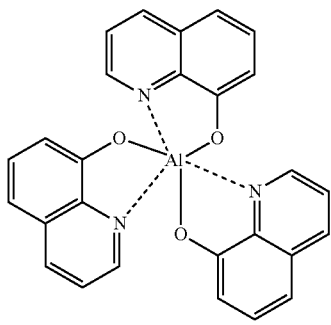

[Chemical Formula 18]

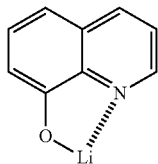

Green light emitting diode A-1 including the compound according to Example 1 of the present invention was manufactured by the aforementioned method.

Further, light emitting diodes A-2 to A-4 were manufactured through the process that was substantially the same as the process of manufacturing the light emitting diode A-1, except that the first layer and the second layer were formed by using each of the compounds according to Examples 3, 4, and 8 as the host material.

Manufacturing of Comparative Elements 1 to 4

Comparative elements 1 to 4 were manufactured through the process that was substantially the same as the process of manufacturing light emitting diode A-1, except that the first layer and the second layer were formed by using the compounds according to Comparative Examples 9 to 12 represented by Chemical Formulas a to d as the host material.

Evaluation of Power Efficiency and Life-Span of Light Emitting Diode-1

With respect to each of light emitting diodes A-1 to A-4 according to the present invention and comparative elements 1 to 4, after the sealant for UV curing was dispensed at the edge of the cover glass to which the moisture absorbent (getter) was attached in the globe box under the nitrogen atmosphere, each of the light emitting diodes and the comparative elements was adhered to the cover glass, and UV light was radiated to perform curing. With respect to each of light emitting diodes A-1 to A-4 and comparative elements 1 to 4 as prepared in the above, power efficiency was measured based on the value when luminance was 500 cd/m$^2$. The result is described in Table 1.

Further, the life-span of each of light emitting diodes A-1 to A-4 and comparative elements 1 to 4 was measured by using the life-span measurement apparatus installed in the oven for measurement constantly maintaining the temperature of about 85° C. The result is described in Table 1.

In Table 1, a unit of the measurement result of power efficiency is lm/W. Further, in Table 1, in the case where initial luminance of the light emitting diode is 1,000 cd/m$^2$, $T_{75}$ means a time required until luminance of the light emitting diode becomes 75% of the initial luminance. The value of the life-span may be converted into the life-span expected in the case where measurement is performed under another measurement condition based on the conversion equation publicly known to a person with skill in the art.

TABLE 1

| Element No. | Power efficiency [lm/W] | Life-span ($T_{75}$@85° C.[hr]) |
|---|---|---|
| Light emitting diode A-1 | 32.1 | 832 |
| Light emitting diode A-2 | 31.4 | 812 |
| Light emitting diode A-3 | 30.6 | 791 |
| Light emitting diode A-4 | 30.8 | 783 |
| Comparative element 1 | 9.2 | 227 |
| Comparative element 2 | 10.3 | 234 |
| Comparative element 3 | 9.5 | 244 |
| Comparative element 4 | 8.5 | 225 |

Referring to Table 1, it can be seen that power efficiency of light emitting diodes A-1 to A-4 is about 32.1 lm/W, about 31.4 lm/W, about 30.6 lm/W, and about 30.8 lm/W, respectively. That is, it can be seen that power efficiency of each of the light emitting diodes manufactured by using the compounds according to Examples 1, 3, 4, and 8 of the present invention is at least about 30.0 lm/W. On the other hand, it can be seen that since power efficiency of comparative elements 1 to 4 is about 8.5 lm/W to about 10.3 lm/W, the power efficiency of the light emitting diodes manufactured by using the compounds according to the Examples of the present invention is better than the power efficiency of comparative elements 1 to 4.

Further, it can be seen that the life-span of each of the light emitting diodes manufactured by using the compounds according to the Examples of the present invention is at least about 783 hours, and as compared to the life-span of comparative elements 1 to 4 of about 244 hours or less, the life-spans of the light emitting diodes including the compounds according to the Examples of the present invention are better than the life-spans of comparative elements 1 to 4.

Further, considering that evaluation of the life-span property of the light emitting diode is performed under the acceleration condition (severe condition) of 85° C., from the fact that that the life-span property of the light emitting diodes including the compounds according to the Examples of the present invention is better than that of comparative elements 1 to 4, it can be seen that heat resistance of the light emitting diode manufactured by using the compound according to the present invention is better than that of comparative elements 1 to 4.

Manufacturing of Light Emitting Diodes B-1 to B-4

On the first electrode formed of indium tin oxide (ITO), the P-type dopant (HAT-CN) represented by Chemical Formula 13 was evaporated in the thickness of about 100 Å to form the first layer, and on the first layer, NPB (N,N'-diphenyl-N,N'-bis(1-naphthyl)-1,1'-biphenyl-4,4'-diamine) was evaporated in the thickness of about 300 Å to form the second layer.

On the second layer, the first blocking layer having the thickness of about 100 Å was formed of the compound according to Example 1, on the first blocking layer, mCBP represented by Chemical Formula 14 and Ir(ppy)$_3$ represented by Chemical Formula 15 were co-evaporated at the weight ratio of 100:9 to form the light emitting layer having the thickness of about 300 Å, and on the light emitting layer, mCBP was evaporated again in the thickness of about 50 Å to form the second blocking layer.

Then, on the second blocking layer, BPhen represented by Chemical Formula 16 and Alq$_3$ represented by Chemical Formula 17 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 18.

On the electron injection layer, the second electrode using the aluminum thin film having the thickness of 1,000 Å was formed to manufacture green light emitting diode B-1 including the compound according to Example 1 of the present invention.

Light emitting diodes B-2, B-3, and B-4 were manufactured through the process that was substantially the same as the process of manufacturing the light emitting diode B-1, except that the first blocking layer was manufactured by using each of the compounds according to Examples 3, 4, and 8 of the present invention.

Manufacturing of Comparative Elements 5 and 6

Comparative element 5 was manufactured through the process that was substantially the same as the process of manufacturing the light emitting diode B-1, except that the first blocking layer was manufactured by using the compound according to Comparative Example 10 represented by Chemical Formula b.

Further, comparative element 6 was manufactured through the process that was substantially the same as the process of manufacturing the light emitting diode B-1, except that the first blocking layer was manufactured by using the compound according to Comparative Example 11 represented by Chemical Formula c.

Evaluation of power efficiency and life-span of light emitting diode-2

With respect to each of light emitting diodes B-1 to B-4 and comparative elements 5 and 6 according to the present invention as prepared in the above, power efficiency was measured based on the value when luminance is 500 cd/m$^2$ by the method that was substantially the same as in the power efficiency measurement experiment of light emitting diodes A-1 to A-4.

Further, the life-span of each of light emitting diodes B-1 to B-4 and comparative elements 5 and 6 was measured by the method that was substantially the same as in the aforementioned life-span evaluation experiment of light emitting diodes A-1 to A-4.

The results of power efficiency and the life-span of each of the light emitting diodes B-1 to B-4 and comparative elements 5 and 6 are described in Table 2. In Table 2, a unit of the measurement result of power efficiency is lm/W. Further, in Table 2, in the case where initial luminance of the light emitting diode is 1,000 cd/m$^2$, $T_{75}$ means a time required until luminance of the light emitting diode becomes 75% of the initial luminance. The value of the life-span may be converted into the life-span expected in the case where measurement is performed under another measurement condition based on the conversion equation publicly known to the person with skill in the art.

TABLE 2

| Element No. | Power efficiency [lm/W] | Life-span ($T_{75}$@85° C.[hr]) |
| --- | --- | --- |
| Light emitting diode B-1 | 34.9 | 714 |
| Light emitting diode B-2 | 34.7 | 681 |
| Light emitting diode B-3 | 33.1 | 664 |
| Light emitting diode B-4 | 33.5 | 656 |
| Comparative element 5 | 11.2 | 212 |
| Comparative element 6 | 12.5 | 218 |

Referring to Table 2, it can be seen that power efficiency of light emitting diodes B-1 to B-4 manufactured by using the compounds according to the present invention is about 34.9 lm/W, about 34.7 lm/W, about 33.1 lm/W, and about 33.5 lm/W, respectively, and thus is at least about 33.1 lm/W, but power efficiency of comparative element 5 is just about 11.2 lm/W and power efficiency of comparative element 6 is just about 12.5 lm/W.

Further, it can be seen that the life-span of each of light emitting diodes B-1 to B-4 is at least about 656 hours, and as compared to the life-spans of comparative elements 5 and 6 which are about 212 hours and about 218 hours, respectively, the life-spans of the light emitting diodes manufactured by using the compounds according to the present invention are relatively longer than those of comparative elements 5 and 6.

Further, considering that evaluation of the life-span property of the light emitting diode is performed under the acceleration condition (severe condition) of 85° C., from the fact that the life-span property of the light emitting diode including the compound according to the present invention is longer than that of comparative elements 5 and 6, it can be seen that heat resistance of the light emitting diode manufactured by using the compound according to the present invention is excellent.

Manufacturing of light emitting diodes C-1 to C-4

On the first electrode formed of indium tin oxide (ITO), NPB as the host material was evaporated at the rate of 1 Å/sec, and simultaneously, the P-type dopant (HAT-CN) represented by Chemical Formula 13 was co-evaporated at the ratio of about 5 parts by weight based on 100 parts by weight of the host material to form the first layer having the thickness of 100 Å. On the first layer, NPB was evaporated in the thickness of 300 Å to form the second layer. On the second layer, the first blocking layer having the thickness of about 100 Å was formed of the compound according to Example 1, on the first blocking layer, mCBP represented by Chemical Formula 14 and Ir(ppy)$_3$ represented by Chemical Formula 15 were co-evaporated at the weight ratio of 100:9 to form the light emitting layer having the thickness of about 300 Å, and on the light emitting layer, mCBP was evaporated again in the thickness of about 50 Å to form the second blocking layer.

Then, on the second blocking layer, BPhen represented by Chemical Formula 16 and Alq$_3$ represented by Chemical Formula 17 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 18.

On the electron injection layer, the second electrode using the aluminum thin film having the thickness of 1,000 Å was formed to manufacture green light emitting diode C-1 including the compound according to Example 1 of the present invention.

Light emitting diodes C-2, C-3, and C-4 were manufactured through the process that was substantially the same as the process of manufacturing the light emitting diode C-1, except that the first blocking layer was manufactured by using each of the compounds according to Examples 5, 6, and 9 of the present invention.

Manufacturing of Comparative Elements 7 and 8

Comparative element 7 was manufactured through the process that was substantially the same as the process of manufacturing the light emitting diode C-1, except that the first blocking layer was manufactured by using the compound according to Comparative Example 10 represented by Chemical Formula b.

Comparative element 8 was manufactured through the process that was substantially the same as the process of manufacturing the light emitting diode C-1, except that the first blocking layer was manufactured by using the compound according to Comparative Example 11 represented by Chemical Formula c.

Evaluation of Power Efficiency and Life-Span of Light Emitting Diode-3

With respect to each of light emitting diodes C-1 to C-4 and comparative elements 7 and 8 as prepared in the above, power efficiency was measured based on the value when luminance is 500 cd/m$^2$ by the method that was substantially the same as in the power efficiency measurement experiment of light emitting diodes A-1 to A-4.

Further, the life-span of each of light emitting diodes C-1 to C-4 and comparative elements 7 and 8 was measured by the method that was substantially the same as in the aforementioned life-span evaluation experiment of light emitting diodes A-1 to A-4.

The results of power efficiency and the life-span of each of the light emitting diodes C-1 to C-4 and comparative elements 7 and 8 are described in Table 3. In Table 3, a unit of the measurement result of power efficiency is lm/W. Further, in Table 3, in the case where initial luminance of the light emitting diode is 1,000 cd/m$^2$, $T_{75}$ means a time required until luminance of the light emitting diode becomes 75% of the initial luminance. The value of the life-span may be converted into the life-span expected in the case where measurement is performed under another measurement condition based on the conversion equation publicly known to the person with skill in the art.

TABLE 3

| Element No. | Power efficiency [lm/W] | Life-span ($T_{75}$@85° C.[hr]) |
|---|---|---|
| Light emitting diode C-1 | 36.1 | 739 |
| Light emitting diode C-2 | 32.3 | 734 |
| Light emitting diode C-3 | 31.2 | 656 |
| Light emitting diode C-4 | 30.1 | 633 |
| Comparative element 7 | 12.6 | 218 |
| Comparative element 8 | 13.1 | 220 |

Referring to Table 3, it can be seen that the power efficiency of light emitting diodes C-1 to C-4 is about 36.1 lm/W, about 32.3 lm/W, about 31.2 lm/W, and about 30.1 lm/W, respectively, but the power efficiency of comparative element 7 is just about 12.6 lm/W and the power efficiency of comparative element 8 is just about 13.1 lm/W. Therefore, it can be seen that power efficiency of the light emitting diodes including the compound according to the present invention is better than that of comparative elements 7 and 8.

Further, it can be seen that the life-spans of light emitting diodes C-1 to C-4 are about 739 hours, about 734 hours, about 656 hours, and about 633 hours, respectively, but the life-span of comparative element 7 is just about 218 hours and the life-span of comparative element 8 is just about 220 hours. Therefore, it can be seen that life-spans of the light emitting diodes including the compound according to the present invention are longer than those of comparative elements 7 and 8.

Further, considering that evaluation of the life-span property of the light emitting diode is performed under the acceleration condition (severe condition) of 85° C., from the fact that the life-span property of the light emitting diode including the compound according to the present invention is better than that of comparative elements 7 and 8, it can be seen that heat resistance of the light emitting diode manufactured by using the compound according to the present invention is good.

Manufacturing of Light Emitting Diodes D-1 to D-4

On the first electrode formed of indium tin oxide (ITO), the compound according to Example 1 as the host material was evaporated at the rate of 1 Å/sec, and simultaneously, the P-type dopant (HAT-CN) represented by Chemical Formula 13 was co-evaporated at the ratio of about 5 parts by weight based on 100 parts by weight of the host material to form the first layer having the thickness of 100 Å. On the first layer, NPB was evaporated in the thickness of 300 Å to form the second layer. On the second layer, mCBP represented by Chemical Formula 14 and Ir(ppy)$_3$ represented by Chemical Formula 15 were co-evaporated at the weight ratio of 100:9 to form the light emitting layer having the thickness of about 300 Å, and on the light emitting layer, mCBP was evaporated again in the thickness of about 50 Å to form the blocking layer.

Then, on the blocking layer, BPhen represented by Chemical Formula 16 and Alq$_3$ represented by Chemical Formula 17 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 18.

On the electron injection layer, the second electrode using the aluminum thin film having the thickness of 1,000 Å was formed to manufacture green light emitting diode D-1 including the compound according to Example 1 of the present invention.

Light emitting diodes D-2, D-3, and D-4 were manufactured through the process that was substantially the same as the process of manufacturing light emitting diode D-1, except that the first layer was manufactured by using each of the compounds according to Examples 3, 4, and 8 of the present invention.

Manufacturing of Comparative Elements 9 and 10

Comparative element 9 was manufactured through the process that was substantially the same as the process of manufacturing light emitting diode D-1, except that a light emitting diode was manufactured by using the compound according to Comparative Example 10 represented by Chemical Formula b as the host material of the first layer.

Comparative element 10 was manufactured through the process that was substantially the same as the process of manufacturing light emitting diode D-1, except that a light emitting diode was manufactured by using the compound according to Comparative Example 11 represented by Chemical Formula c as the host material of the first layer.

Evaluation of Power Efficiency and Life-Span of Light Emitting Diode-4

With respect to each of light emitting diodes D-1 to D-4 and comparative elements 9 and 10 as prepared in the above, power efficiency was measured based on the value when luminance is 500 cd/m$^2$ by the method that was substantially the same as in the power efficiency measurement experiment of light emitting diodes A-1 to A-4.

Further, the life-span of each of light emitting diodes D-1 to D-4 and comparative elements 9 and 10 was measured by the method that was substantially the same as in the aforementioned life-span evaluation experiment of light emitting diodes A-1 to A-4.

The results of power efficiency and the life-span of each of the light emitting diodes D-1 to D-4 and comparative elements 9 and 10 are described in Table 4. In Table 4, a unit of the measurement result of power efficiency is lm/W. Further, in Table 4, in the case where initial luminance of the light emitting diode is 1,000 cd/m$^2$, $T_{75}$ means a time required until luminance of the light emitting diode becomes 75% of the initial luminance. The value of the life-span may be converted into the life-span expected in the case where measurement is performed under another measurement condition based on the conversion equation publicly known to the person with skill in the art.

TABLE 4

| Element No. | Power efficiency [lm/W] | Life-span ($T_{75}$@85° C.[hr]) |
| --- | --- | --- |
| Light emitting diode D-1 | 30.7 | 760 |
| Light emitting diode D-2 | 30.5 | 731 |
| Light emitting diode D-3 | 29.1 | 715 |
| Light emitting diode D-4 | 29.5 | 707 |
| Comparative element 9 | 9.3 | 202 |
| Comparative element 10 | 8.9 | 193 |

Referring to Table 4, it can be seen that the power efficiency of each of light emitting diodes D-1 to D-4 is at least about 29.1 lm/W, but power efficiency of comparative element 9 is just about 9.3 lm/W and power efficiency of comparative element 10 is just about 8.9 lm/W. Therefore, it can be seen that power efficiency of the light emitting diodes using the compound according to the present invention is better than that of comparative elements 9 and 10.

Further, it can be seen that the life-span of each of light emitting diodes D-1 to D-4 is at least about 707 hours, but the life-span of comparative element 9 is just about 202 hours and the life-span of comparative element 10 is just about 193 hours. Therefore, it can be seen that the life-spans of the light emitting diodes using the compound according to the present invention are longer than those of comparative elements 9 and 10.

Further, considering that evaluation of the life-span property of the light emitting diode is performed under the acceleration condition (severe condition) of 85° C., from the fact that the life-span property of the light emitting diode including the compound according to the present invention is better than that of comparative elements 9 and 10, it can be seen that heat resistance of the light emitting diode manufactured by using the compound according to the present invention is good.

Manufacturing of Light Emitting Diodes E-1 to E-4

On the first electrode formed of indium tin oxide (ITO), NPB as the host material was evaporated at the rate of 1 Å/sec, and simultaneously, the P-type dopant (HAT-CN) represented by Chemical Formula 13 was co-evaporated at the ratio of about 5 parts by weight based on 100 parts by weight of the host material to form the first layer having the thickness of 100 Å. On the first layer, the compound according to Example 1 was evaporated in the thickness of 300 Å to form the second layer. On the second layer, mCBP represented by Chemical Formula 14 and Ir(ppy)$_3$ represented by Chemical Formula 15 were co-evaporated at the weight ratio of 100:9 to form the light emitting layer having the thickness of about 300 Å, and on the light emitting layer, mCBP was evaporated again in the thickness of about 50 Å to form the blocking layer.

Then, on the blocking layer, BPhen represented by Chemical Formula 16 and Alq$_3$ represented by Chemical Formula 17 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 18.

On the electron injection layer, the second electrode using the aluminum thin film having the thickness of 1,000 Å was formed to manufacture green light emitting diode E-1 including the compound according to Example 1 of the present invention.

Light emitting diodes E-2, E-3, and E-4 were manufactured through the process that was substantially the same as the process of manufacturing light emitting diode E-1, except that the second layer was manufactured by using each of the compounds according to Examples 3, 4, and 8 of the present invention.

Manufacturing of Comparative Elements 11 and 12

Comparative element 11 was manufactured through the process that was substantially the same as the process of manufacturing light emitting diode E-1, except that the second layer was manufactured by using the compound according to Comparative Example 10 represented by Chemical Formula b.

Comparative element 12 was manufactured through the process that was substantially the same as the process of manufacturing light emitting diode E-1, except that the second layer was manufactured by using the compound according to Comparative Example 11 represented by Chemical Formula c.

Evaluation of Power Efficiency and Life-Span of Light Emitting Diode-5

With respect to each of light emitting diodes E-1 to E-4 and comparative elements 11 and 12 as prepared in the above, power efficiency was measured based on the value when luminance is 500 cd/m$^2$ by the method that was substantially the same as in the power efficiency measurement experiment of light emitting diodes A-1 to A-4.

Further, the life-span of each of light emitting diodes E-1 to E-4 and comparative elements 11 and 12 was measured by the method that was substantially the same as in the aforementioned life-span evaluation experiment of light emitting diodes A-1 to A-4.

The results of power efficiency and the life-span of each of light emitting diodes E-1 to E-4 and comparative elements 11 and 12 are shown in Table 5. In Table 5, a unit of the measurement result of power efficiency is lm/W. Further, in Table 5, in the case where initial luminance of the light emitting diode is 1,000 cd/m$^2$, $T_{75}$ means a time required until luminance of the light emitting diode becomes 75% of the initial luminance. The value of the life-span may be converted into the life-span expected in the case where measurement is performed under another measurement condition based on the conversion equation publicly known to the person with skill in the art.

TABLE 5

| Element No. | Power efficiency [lm/W] | Life-span ($T_{75}$@85° C.[hr]) |
| --- | --- | --- |
| Light emitting diode E-1 | 30.0 | 762 |
| Light emitting diode E-2 | 29.8 | 728 |
| Light emitting diode E-3 | 28.5 | 711 |
| Light emitting diode E-4 | 28.7 | 705 |

TABLE 5-continued

| Element No. | Power efficiency [lm/W] | Life-span ($T_{75}$@85° C.[hr]) |
| --- | --- | --- |
| Comparative element 11 | 9.8 | 217 |
| Comparative element 12 | 9.2 | 209 |

Referring to Table 5, it can be seen that power efficiency of each of light emitting diodes E-1 to E-4 is at least about 28.5 lm/W, but power efficiency of comparative element 11 is just about 9.8 lm/W and power efficiency of comparative element 12 is just about 9.2 lm/W. Therefore, it can be seen that power efficiency of the light emitting diodes using the compound according to the present invention is better than those of comparative elements 11 and 12.

Further, it can be seen that the life-span of each of light emitting diodes E-1 to E-4 is at least about 705 hours or more, but the life-span of comparative element 11 is just about 217 hours and the life-span of comparative element 12 is just about 209 hours. Therefore, it can be seen that the life-spans of the light emitting diodes using the compound according to the present invention are longer than those of comparative elements 11 and 12.

Further, considering that evaluation of the life-span property of the light emitting diode is performed under the acceleration condition (severe condition) of 85° C., from the fact that the life-span property of the light emitting diode including the compound according to the present invention is better than that of comparative elements 11 and 12, it can be seen that heat resistance of the light emitting diode manufactured by using the compound according to the present invention is good.

Manufacturing of Light Emitting Diodes F-1 to F-14

On the first electrode formed of indium tin oxide (ITO), the compound according to Example 1 as the host material was evaporated at the rate of 1 Å/sec, and simultaneously, the P-type dopant (HAT-CN) represented by Chemical Formula 13 was co-evaporated at the ratio of about 5 parts by weight based on 100 parts by weight of the host material to form the first layer having the thickness of 100 Å. On the first layer, the compound according to Example 1 was evaporated in the thickness of 300 Å to form the second layer.

On the second layer, the compound represented by the following Chemical Formula 19 and the compound represented by the following Chemical Formula 20 were co-evaporated at the weight ratio of 100:5 to form the light emitting layer having the thickness of about 200 Å.

Then, on the light emitting layer, the compound represented by the following Chemical Formula 21 and Liq represented by Chemical Formula 18 were co-evaporated at the weight ratio of 50:50 to form the electron transport layer having the thickness of about 360 Å. Subsequently, on the electron transport layer, the electron injection layer having the thickness of about 10 Å was formed by using Liq represented by Chemical Formula 18.

On the electron injection layer, the second electrode using the aluminum thin film having the thickness of 1,000 Å was formed.

[Chemical Formula 19]

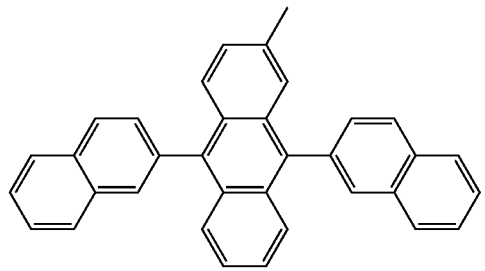

[Chemical Formula 20]

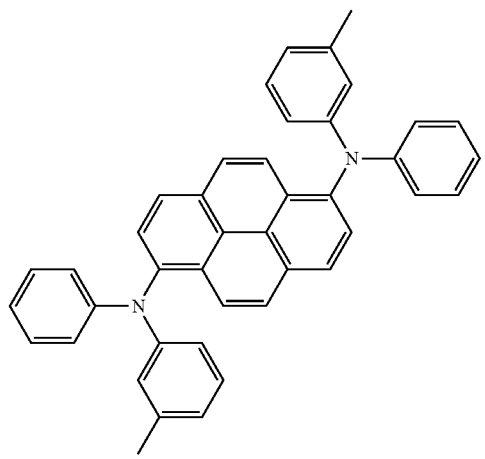

[Chemical Formula 21]

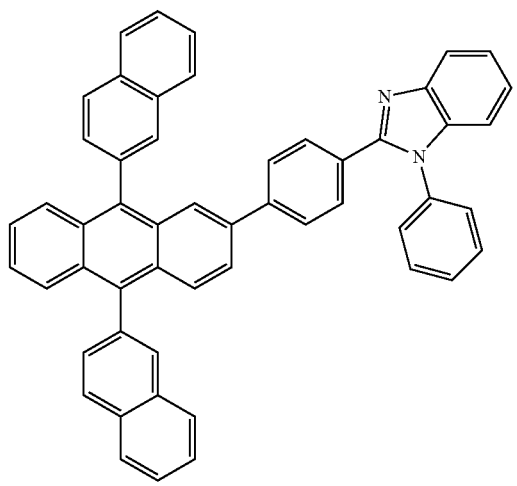

Blue light emitting diode F-1 including the compound according to Example 1 of the present invention was manufactured by the aforementioned method.

Further, light emitting diodes F-1 to F-14 were manufactured through the process that was substantially the same as the process of manufacturing light emitting diode F-1, except that the first layer and the second layer were formed by using each of the compounds according to Examples 2 to 14 as the host material.

Manufacturing of Comparative Elements 13 to 20

Comparative elements 13 to 20 were manufactured through the process that was substantially the same as the process of manufacturing light emitting diode F-1, except that the first layer and the second layer were formed by using the compounds according to Comparative Examples 1 to 8 as the host material.

Evaluation of Power Efficiency and Life-Span of Light Emitting Diode-6

With respect to each of light emitting diodes F-1 to F-14 and comparative elements 13 to 20, after the sealant for UV curing was dispensed at the edge of the cover glass to which the moisture absorbent (getter) was attached in the globe box under the nitrogen atmosphere, each of the light emitting diodes and the comparative elements was adhered to the cover glass, and UV light was radiated to perform curing. With respect to each of light emitting diodes F-1 to F-14 and comparative elements 13 to 20 as prepared in the above, power efficiency was measured based on the value when luminance was 500 cd/m$^2$. The result is described in Table 6.

Further, the life-span of each of light emitting diodes F-1 to F-14 and comparative elements 13 to 20 was measured by using the life-span measurement apparatus installed in the oven for measurement constantly maintaining the temperature of about 85° C. The result is described in Table 6.

In Table 6, a unit of the measurement result of power efficiency is lm/W. Further, in Table 6, in the case where initial luminance of the light emitting diode is 1,000 cd/m$^2$, $T_{75}$ means a time required until luminance of the light emitting diode becomes 75% of the initial luminance. The value of the life-span may be converted into the life-span expected in the case where measurement is performed under another measurement condition based on the conversion equation publicly known to the person with skill in the art.

TABLE 6

| Element No. | Power efficiency [lm/W] | Life-span ($T_{75}$@85° C.[hr]) |
|---|---|---|
| Light emitting diode F-1 | 8.70 | 145 |
| Light emitting diode F-2 | 7.60 | 121 |
| Light emitting diode F-3 | 8.50 | 135 |
| Light emitting diode F-4 | 8.00 | 130 |
| Light emitting diode F-5 | 7.40 | 141 |
| Light emitting diode F-6 | 7.10 | 120 |
| Light emitting diode F-7 | 7.00 | 115 |
| Light emitting diode F-8 | 8.20 | 127 |
| Light emitting diode F-9 | 7.10 | 118 |
| Light emitting diode F-10 | 7.80 | 122 |
| Light emitting diode F-11 | 6.90 | 116 |
| Light emitting diode F-12 | 7.30 | 133 |
| Light emitting diode F-13 | 8.40 | 147 |
| Light emitting diode F-14 | 7.20 | 137 |
| Comparative element 13 | 5.61 | 77 |
| Comparative element 14 | 5.90 | 81 |
| Comparative element 15 | 5.50 | 75 |
| Comparative element 16 | 5.00 | 69 |
| Comparative element 17 | 5.20 | 70 |
| Comparative element 18 | 4.90 | 61 |
| Comparative element 19 | 5.30 | 72 |
| Comparative element 20 | 4.10 | 52 |

Referring to Table 6, it can be seen that power efficiency of comparative element 13 (position No. 2 or 7) and comparative element 20 (position No. 4 or 5) including the compound having the substitution position between Cz and Cz, which is different from that of the compound according to the present invention, is about 5.61 lm/W and about 4.10 lm/W, respectively, and the life-spans are 77 hours and 52 hours, respectively. On the other hand, it can be seen that light emitting diodes F-1 to F-14 using the compounds according to the present invention where the substitution position between Cz and Cz is No. 3 or 6 exhibit power efficiency and the life-span that are better than those of comparative elements 13 and 20. Particularly, it can be seen that as compared to comparative element 13, in light emitting diode F-6 using the compound according to Example 6 of the present invention where only the substitution position between Cz and Cz is different, power efficiency is increased by about 27% and the life-span is lengthened by about 56%. Further, it can be seen that as compared to comparative element 20, in light emitting diode F-2 using the compound according to Example 2 of the present invention where only the substitution position between Cz and Cz is different, power efficiency is increased by about 85% and the life-span is lengthened by about 133%.

Further, it can be seen that power efficiency of comparative element 14 (position No. 3 or 6) including the compound having the substitution position of DBF, which is different from that of the compound according to the present invention, is about 5.90 lm/W and the life-span is about 81 hours. On the other hand, it can be seen that in light emitting diodes F-7, F-9, and F-11 using the compounds according to the present invention where the substitution position of DBF is No. 1 or 8, power efficiency is increased by at least 16% and the life-span is lengthened by at least 41%.

Meanwhile, from the fact that Cz is not positioned at the center but substituted at the side chain, it can be seen that power efficiency of comparative elements 15, 16, and 19 including the compound that is different from the compound according to the present invention is about 5.45 lm/W, about 5.01 lm/W, and about 5.27 lm/W, respectively, and the life-spans are about 75 hours, about 69 hours, and about 72 hours. On the other hand, it can be seen that light emitting diodes F-1 to F-14 using the compounds according to the present invention where Cz is positioned at the center exhibit power efficiency and the life-span that are better than those of comparative elements 15, 16, and 19. Particularly, it can be seen that as compared to comparative element 15 having the compound having the Cz-DBT-DBT-Cz structure, in light emitting diode F-2 using the compound having the DBT-Cz-Cz-DBT structure according to Example 2 of the present invention, power efficiency is increased by about 39% and the life-span is lengthened by about 61%. Further, it can be seen that as compared to comparative element 16 including the compound having the Cz-DBF-DBF-Cz structure, in light emitting diode F-7 using the compound having the DBF-Cz-Cz-DBF structure according to Example 7 of the present invention, power efficiency is increased by about 40% and the life-span is lengthened by about 67%.

Moreover, from the fact that three or more Czs are included in the structure, it can be seen that power efficiency of comparative elements 17 and 18 including the compound having the structure that is different from that of the compound according to the present invention is about 5.20 lm/W and about 4.90 lm/W, respectively, and the life-spans are about 70 hours and about 61 hours. On the other hand, it can be seen that light emitting diodes F-1 to F-14 using the compounds having only two Czs according to the present invention exhibit power efficiency and the life-span that are better than those of comparative elements 17 and 18. Particularly, it can be seen that as compared to comparative element 18 including the compound having the DBT-Cz-Cz-Cz-DBT structure, in light emitting diode F-2 using the compound having the DBT-Cz-Cz-DBT structure according to Example 2 of the present invention, power efficiency is increased by about 55% and the life-span is lengthened by about 98% as compared to comparative element 18.

Manufacturing of Light Emitting Diodes G-1 to G-14

On the first electrode formed of indium tin oxide (ITO), the P-type dopant (HAT-CN) represented by Chemical Formula 13 was evaporated in the thickness of about 100 Å to form the first layer, and on the first layer, NPB (N,N'-diphenyl-N,N'-bis(1-naphthyl)-1,1'-biphenyl-4,4'-diamine) was evaporated in the thickness of about 300 Å to form the second layer.

On the second layer, the first blocking layer having the thickness of about 100 Å was formed of the compound according to Example 1, and on the first blocking layer, the compound represented by Chemical Formula 19 and the compound represented by Chemical Formula 20 were co-evaporated at the weight ratio of 100:5 to form the light emitting layer having the thickness of about 200 Å. Then, on the light emitting layer, the compound represented by Chemical Formula 21 and Liq represented by Chemical Formula 18 were co-evaporated at the weight ratio of 50:50 to form the electron transport layer having the thickness of about 360 Å. Subsequently, on the electron transport layer, the electron injection layer having the thickness of about 10 Å was formed by using Liq represented by Chemical Formula 18.

On the electron injection layer, the second electrode using the aluminum thin film having the thickness of 1,000 Å was formed to manufacture blue light emitting diode G-1 including the compound according to Example 1 of the present invention.

Light emitting diodes G-2 to G-14 were manufactured through the process that was substantially the same as the process of manufacturing light emitting diode G-1, except that the first blocking layer was manufactured by using each of the compounds according to Examples 2 to 14 of the present invention.

Manufacturing of Comparative Elements 21 and 28

Comparative elements 21 to 28 were manufactured through the process that was substantially the same as the process of manufacturing light emitting diode G-1, except that the first blocking layer was manufactured by using the compound according to Comparative Examples 1 to 8.

Evaluation of Power Efficiency and Life-Span of Light Emitting Diode-7

With respect to each of light emitting diodes G-1 to G-14 and comparative elements 21 to 28 as prepared in the above, power efficiency was measured based on the value when luminance is 500 cd/m² by the method that was substantially the same as in the power efficiency measurement experiment of light emitting diodes F-1 to F-14.

Further, the life-span of each of light emitting diodes G-1 to G-14 and comparative elements 21 to 28 was measured by the method that was substantially the same as in the aforementioned life-span evaluation experiment of light emitting diodes F-1 to F-14.

The results of power efficiency and the life-span of each of light emitting diodes G-1 to G-14 and comparative elements 21 to 28 are described in Table 7. In Table 7, a unit of the measurement result of power efficiency is lm/W. Further, in Table 7, in the case where initial luminance of the light emitting diode is 1,000 cd/m², $T_{75}$ means a time required until luminance of the light emitting diode becomes 75% of the initial luminance. The value of the life-span may be converted into the life-span expected in the case where measurement is performed under another measurement condition based on the conversion equation publicly known to the person with skill in the art.

TABLE 7

| Element No. | Power efficiency [lm/W] | Life-span ($T_{75}$@85° C.[hr]) |
|---|---|---|
| Light emitting diode G-1 | 7.62 | 127 |
| Light emitting diode G-2 | 6.64 | 107 |
| Light emitting diode G-3 | 7.39 | 120 |
| Light emitting diode G-4 | 7.03 | 114 |
| Light emitting diode G-5 | 6.70 | 123 |
| Light emitting diode G-6 | 6.39 | 105 |
| Light emitting diode G-7 | 6.12 | 102 |
| Light emitting diode G-8 | 7.19 | 111 |
| Light emitting diode G-9 | 6.21 | 104 |
| Light emitting diode G-10 | 6.85 | 109 |
| Light emitting diode G-11 | 6.10 | 102 |
| Light emitting diode G-12 | 6.32 | 117 |
| Light emitting diode G-13 | 7.30 | 131 |
| Light emitting diode G-14 | 6.50 | 125 |
| Comparative element 21 | 4.83 | 66 |
| Comparative element 22 | 5.07 | 69 |
| Comparative element 23 | 4.69 | 64 |
| Comparative element 24 | 4.31 | 59 |
| Comparative element 25 | 4.47 | 60 |
| Comparative element 26 | 4.21 | 52 |
| Comparative element 27 | 4.53 | 62 |
| Comparative element 28 | 3.53 | 45 |

Referring to Table 7, it can be seen that power efficiency of comparative element 21 (position No. 2 or 7) and comparative element 28 (position No. 4 or 5) including the compound having the substitution position between Cz and Cz, which is different from that of the compound according to the present invention, is about 4.83 lm/W and about 3.53 lm/W, respectively, and the life-spans are 66 hours and 45 hours, respectively. On the other hand, it can be seen that light emitting diodes G-1 to G-14 using the compounds according to the present invention where the substitution position between Cz and Cz is No. 3 or 6 exhibit power efficiency and the life-span that are better than those of comparative elements 21 and 28. Particularly, it can be seen that as compared to comparative element 21, in light emitting diode G-6 using the compound according to Example 6 of the present invention where only the substitution position between Cz and Cz is different, power efficiency is increased by about 32% and the life-span is lengthened by about 60%. Further, it can be seen that as compared to comparative element 28, in light emitting diode G-2 using the compound according to Example 2 of the present invention where only the substitution position between Cz and Cz is different, power efficiency is increased by about 88% and the life-span is lengthened by about 137%.

Further, it can be seen that power efficiency of comparative element 22 (position No. 3 or 6) including the compound having the substitution position of DBF, which is different from that of the compound according to the present invention, is about 5.07 lm/W and the life-span is about 69 hours. On the other hand, it can be seen that in light emitting diodes G-7, G-9, and G-11 using the compounds according to the present invention where the substitution position of DBF is No. 1 or 8, power efficiency is increased by about 20% and the life-span is lengthened by about 48% as compared to comparative element 22.

Meanwhile, from the fact that Cz is not positioned at the center but substituted at the side chain, it can be seen that power efficiency of comparative elements 23, 24, and 27 including the compound that is different from the compound according to the present invention is about 4.69 lm/W, about 4.31 lm/W, and about 4.53 lm/W, respectively, and the life-spans are about 64 hours, about 59 hours, and about 62 hours. On the other hand, it can be seen that light emitting diodes G-1 to G-14 using the compounds according to the present invention where Cz is positioned at the center exhibit power efficiency and the life-span that are better than those of comparative elements 23, 24, and 27. Particularly, it can be seen that as compared to comparative element 23 including the compound having the Cz-DBT-DBT-Cz structure, in light emitting diode G-2 using the compound having the DBT-Cz-Cz-DBT structure according to Example 2 of the present invention, power efficiency is increased by about 42% and the life-span is lengthened by about 67%. Further, it can be seen that as compared to comparative element 24 including the compound having the Cz-DBF-DBF-Cz structure, in light emitting diode G-7 using the compound having the DBF-Cz-Cz-DBF structure according to Example 7 of the present invention, power efficiency is increased by about 42% and the life-span is lengthened by about 73%.

Moreover, from the fact that three or more Czs are included in the structure, it can be seen that power efficiency of comparative elements 25 and 26 including the compound that is different from the compound according to the present invention is about 4.47 lm/W and about 4.21 lm/W, respectively, and the life-spans are about 60 hours and about 52 hours. On the other hand, it can be seen that light emitting diodes G-1 to G-14 using the compounds having only two Czs according to the present invention exhibit power efficiency and the life-span that are better than those of comparative elements 25 and 26. Particularly, it can be seen that as compared to comparative element 26 having the DBT-Cz-Cz-Cz-DBT structure, in light emitting diode G-2 using the compound having the DBT-Cz-Cz-DBT structure according to Example 2 of the present invention, power efficiency is increased by about 58% and the life-span is lengthened by about 105%.

Manufacturing of Light Emitting Diodes H-1 to H-14

On the first electrode formed of indium tin oxide (ITO), NPB as the host material was evaporated at the rate of 1 Å/sec, and simultaneously, the P-type dopant (HAT-CN) represented by Chemical Formula 13 was co-evaporated at the ratio of about 5 parts by weight based on 100 parts by weight of the host material to form the first layer having the thickness of 100 Å. On the first layer, NPB was evaporated in the thickness of 300 Å to form the second layer. On the second layer, the first blocking layer having the thickness of about 100 Å was formed of the compound according to Example 1, and on the first blocking layer, the compound represented by Chemical Formula 19 and the compound represented by Chemical Formula 20 were co-evaporated at the weight ratio of 100:5 to form the light emitting layer having the thickness of about 200 Å.

Then, on the light emitting layer, the compound represented by Chemical Formula 21 and Liq represented by Chemical Formula 18 were co-evaporated at the weight ratio of 50:50 to form the electron transport layer having the thickness of about 360 Å. Subsequently, on the electron transport layer, the electron injection layer having the thickness of about 10 Å was formed by using Liq represented by Chemical Formula 18.

On the electron injection layer, the second electrode using the aluminum thin film having the thickness of 1,000 Å was formed to manufacture blue light emitting diode H-1 including the compound according to Example 1 of the present invention.

Light emitting diodes H-2 to H-14 were manufactured through the process that was substantially the same as the process of manufacturing light emitting diode H-1, except that the first blocking layer was manufactured by using each of the compounds according to Examples 2 to 14 of the present invention.

Manufacturing of Comparative Elements 29 to 36

Comparative elements 29 to 36 were manufactured through the process that was substantially the same as the process of manufacturing light emitting diode H-1, except that the first blocking layer was manufactured by using the compound according to Comparative Examples 1 to 8.

Evaluation of Power Efficiency and Life-Span of Light Emitting Diode-8

With respect to each of light emitting diodes H-1 to H-14 and comparative elements 29 to 36 as prepared in the above, power efficiency was measured based on the value when luminance is 500 cd/m$^2$ by the method that was substantially the same as in the power efficiency measurement experiment of light emitting diodes F-1 to F-14.

Further, the life-span of each of light emitting diodes H-1 to H-14 and comparative elements 29 to 36 was measured by the method that was substantially the same as in the aforementioned life-span evaluation experiment of light emitting diodes F-1 to F-14.

The results of power efficiency and the life-span of each of the light emitting diodes H-1 to H-14 and comparative elements 29 to 36 are described in Table 8. In Table 8, a unit of the measurement result of power efficiency is lm/W. Further, in Table 8, in the case where initial luminance of the light emitting diode is 1,000 cd/m$^2$, $T_{75}$ means a time required until luminance of the light emitting diode becomes 75% of the initial luminance. The value of the life-span may be converted into the life-span expected in the case where measurement is performed under another measurement condition based on the conversion equation publicly known to the person with skill in the art.

TABLE 8

| Element No. | Power efficiency [lm/W] | Life-span ($T_{75}$@85° C.[hr]) |
|---|---|---|
| Light emitting diode H-1 | 7.70 | 128 |
| Light emitting diode H-2 | 6.50 | 101 |
| Light emitting diode H-3 | 7.40 | 114 |
| Light emitting diode H-4 | 7.10 | 112 |
| Light emitting diode H-5 | 6.80 | 120 |
| Light emitting diode H-6 | 6.30 | 98 |
| Light emitting diode H-7 | 6.10 | 96 |
| Light emitting diode H-8 | 7.10 | 111 |
| Light emitting diode H-9 | 6.20 | 99 |
| Light emitting diode H-10 | 6.90 | 103 |
| Light emitting diode H-11 | 6.00 | 95 |
| Light emitting diode H-12 | 6.20 | 113 |
| Light emitting diode H-13 | 7.20 | 133 |
| Light emitting diode H-14 | 6.40 | 125 |
| Comparative element 29 | 4.99 | 68 |
| Comparative element 30 | 5.25 | 72 |
| Comparative element 31 | 4.85 | 66 |
| Comparative element 32 | 4.46 | 61 |
| Comparative element 33 | 4.63 | 63 |
| Comparative element 34 | 4.36 | 54 |
| Comparative element 35 | 4.69 | 64 |
| Comparative element 36 | 3.65 | 47 |

Referring to Table 8, it can be seen that power efficiency of comparative element 29 (position No. 2 or 7) and comparative element 36 (position No. 4 or 5) including the compound having the substitution position between Cz and Cz, which is different from that of the compound according to the present invention, is about 4.99 lm/W and about 3.65 lm/W, respectively, and the life-spans are 68 hours and 47 hours, respectively. On the other hand, it can be seen that light emitting diodes H-1 to H-14 using the compounds according to the present invention where the substitution position between Cz and Cz is No. 3 or 6 exhibit power efficiency and the life-span that are better than those of comparative elements 29 and 36. Particularly, it can be seen that as compared to comparative element 29, in light emitting diode H-6 using the compound according to Example 6 of the present invention where only the substitution position between Cz and Cz is different, power efficiency is increased by about 26% and the life-span is lengthened by about 44%. Further, it can be seen that as compared to comparative element 36, in light emitting diode H-2 using the compound according to Example 2 of the present invention where only the substitution position between Cz and Cz is different, power efficiency is increased by about 78% and the life-span is lengthened by about 115%.

Further, it can be seen that power efficiency of comparative element 30 (position No. 3 or 6) including the compound having the substitution position of DBF, which is different from that of the compound according to the present invention, is about 5.25 lm/W and the life-span is about 72 hours. On the other hand, it can be seen that in light emitting diodes H-7, H-9, and H-11 using the compounds according to the present invention where the substitution position of DBF is No. 1 or 8, power efficiency is increased by about 14% and the life-span is lengthened by about 32% as compared to comparative element 30.

Meanwhile, from the fact that Cz is not positioned at the center but substituted at the side chain, it can be seen that power efficiency of comparative elements 31, 32, and 35 including the compound that is different from the compound according to the present invention is about 4.85 lm/W, about 4.46 lm/W, and about 4.69 lm/W, respectively, and the life-spans are about 66 hours, about 61 hours, and about 64 hours. On the other hand, it can be seen that light emitting diodes H-1 to H-14 using the compounds according to the present invention where Cz is positioned at the center exhibit power efficiency and the life-span that are better than those of comparative elements 31, 32, and 35. Particularly, it can be seen that as compared to comparative element 31 including the compound having the Cz-DBT-DBT-Cz structure, in light emitting diode H-2 using the compound having the DBT-Cz-Cz-DBT structure according to Example 2 of the present invention, power efficiency is increased by about 34% and the life-span is lengthened by about 53%. Further, it can be seen that as compared to comparative element 32 having the Cz-DBF-DBF-Cz structure, in light emitting diode H-7 using the compound having the DBF-Cz-Cz-DBF structure according to Example 7 of the present invention, power efficiency is increased by about 37% and the life-span is lengthened by about 57%.

Moreover, from the fact that three or more Czs are included in the structure, it can be seen that power efficiency of comparative elements 33 and 34 including the compound that is different from the compound according to the present invention is about 4.63 lm/W and about 4.36 lm/W, respectively, and the life-spans are about 63 hours and about 54 hours. On the other hand, it can be seen that light emitting diodes H-1 to H-14 using the compounds having only two Czs according to the present invention exhibit power efficiency and the life-span that are better than those of comparative elements 33 and 34. Particularly, it can be seen that as compared to comparative element 34 including the compound having the DBT-Cz-Cz-Cz-DBT structure, in light emitting diode H-2 using the compound having the DBT-Cz-Cz-DBT structure according to Example 2 of the present invention, power efficiency is increased by about 49% and the life-span is lengthened by about 87%.

According to the aforementioned description, a light emitting diode having improved power efficiency, life-span, and thermal stability may be manufactured by using the novel compound according to the present invention.

| EXPLANATION OF CODES | |
| --- | --- |
| 100, 102, 104: Light emitting diode | 10: Base substrate |
| 20: First electrode | 30, 32, 34: Hole transportable layer |
| 33a: First layer | 33b: Second layer |
| 40: Light emitting layer | 50: Second electrode |

What is claimed is:

1. A compound represented by the following Chemical Formula 1:

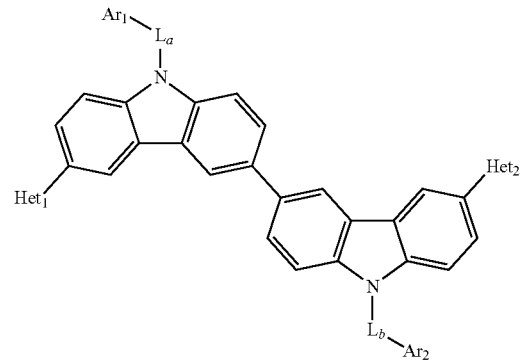

[Chemical Formula 1]

wherein in the Chemical Formula 1, $L_a$ and $L_b$ each independently represents *-$L_1$-$L_2$-$L_3$-$L_4$-*, $L_1$, $L_2$, $L_3$ and $L_4$ each independently represent a single bond, —O—, —S—, an arylene group having 6 to 20 carbon atoms, a heteroarylene group having 2 to 20 carbon atoms, or a cycloalkylene group having 3 to 20 carbon atoms, $Ar_1$ and $Ar_2$ each independently represent hydrogen, an alkyl group having 1 to 6 carbon atoms, an aryl group having 6 to 20 carbon atoms, a heteroaryl group having 2 to 20 carbon atoms, a cycloalkyl group having 3 to 20 carbon atoms, a heterocycloalkyl group having 2 to 20 carbon atoms, a bicycloalkyl group having 5 to 20 carbon atoms, the following Chemical Formula 2-1, or the following Chemical Formula 2-2,

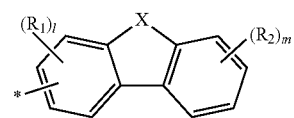

[Chemical Formula 2-1]

-continued

[Chemical Formula 2-2]

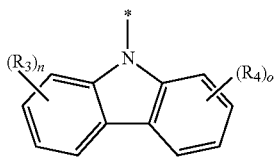

Het$_1$ and Het$_2$ each independently represent the following Chemical Formula 3 or the following Chemical Formula 4,

[Chemical Formula 3]

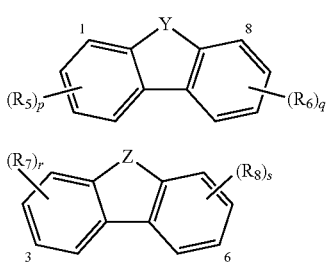

[Chemical Formula 4]

wherein, X represents N—W, O, S, or Si(R$_9$)(R$_{10}$),
W represents hydrogen, an alkyl group having 1 to 6 carbon atoms, an aryl group having 6 to 20 carbon atoms, a heteroaryl group having 2 to 20 carbon atoms, a cycloalkyl group having 3 to 20 carbon atoms, a heterocycloalkyl group having 2 to 20 carbon atoms, or a bicycloalkyl group having 5 to 20 carbon atoms,
Y represents S or O,
Z represents S,
R$_1$, R$_2$, R$_3$, R$_4$, R$_5$, R$_6$, R$_7$, R$_8$, R$_9$, and R$_{10}$ each independently represent an alkyl group having 1 to 6 carbon atoms, an aryl group having 6 to 20 carbon atoms, or a heteroaryl group having 2 to 20 carbon atoms,
l represents an integer of 0 to 3, m, n, and o each independently represent an integer of 0 to 4, any one of p and q represents an integer of 0 to 3 and the other represents an integer of 0 to 4, any one of r and s represents an integer of 0 to 3 and the other represents an integer of 0 to 4,
a substituent group represented by the Chemical Formula 3 is substituted by the compound of the Chemical Formula 1 at carbon position No. 1 or 8,
a substituent group represented by the Chemical Formula 4 is substituted by the compound of the Chemical Formula 1 at carbon position No. 3 or 6, and
in the aforementioned definitions of substituents in Chemical Formulas 1 to 4, the alkyl group, the aryl group, the heteroaryl group, the cycloalkyl group, the heterocycloalkyl group, and the bicycloalkyl group are each independently unsubstituted or substituted by one or more substituent groups selected from the group consisting of an alkyl group having 1 to 6 carbon atoms, an alkoxy group having 1 to 6 carbon atoms, an amine group unsubstituted or substituted by one or more alkyl groups having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

2. The compound of claim 1, wherein
the L$_a$ and the L$_b$ each independently represents the *-L$_1$-L$_2$-L$_3$-L$_4$-*,
the L$_1$, the L$_2$, the L$_3$, and the L$_4$ each independently represent the single bond or the arylene group having 6 to 20 carbon atoms,
the Ar$_1$ and the Ar$_2$ each independently represent the aryl group having 6 to 20 carbon atoms, the heteroaryl group having 2 to 20 carbon atoms, the following Chemical Formula 2-1, or the following Chemical Formula 2-2,

[Chemical Formula 2-1]

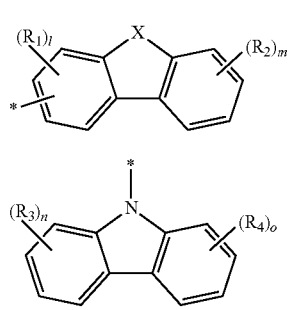

[Chemical Formula 2-2]

the Het$_1$ and the Het$_2$ each independently represent the following Chemical Formula 3 or the following Chemical Formula 4,

[Chemical Formula 3]

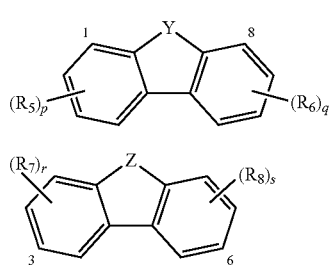

[Chemical Formula 4]

wherein,
the X represents the N—W, the O, the S, or the Si(R$_9$)(R$_{10}$),
the W represents the aryl group having 6 to 20 carbon atoms or the heteroaryl group having 2 to 20 carbon atoms,
the Y represents the S or the O,
the Z represents the S,
the R$_1$, the R$_2$, the R$_3$, the R$_4$, the R$_5$, the R$_6$, the R$_7$, the R$_8$, the R$_9$, and the R$_{10}$ each independently represent the alkyl group having 1 to 6 carbon atoms or the aryl group having 6 to 20 carbon atoms, and
the m, the n, the l, the o, the p, the q, the r, and the s each independently represent the integer of 0 to 2.

3. The compound of claim 1, wherein
the L$_a$ and the L$_b$ each independently represent the single bond or the arylene group having 6 to 20 carbon atoms,
the Ar$_1$ and the Ar$_2$ each independently represent the aryl group having 6 to 20 carbon atoms unsubstituted or substituted by the alkyl group having 1 to 6 carbon atoms or the aryl group having 6 to 20 carbon atoms; the heteroaryl group having 2 to 20 carbon atoms unsubstituted or substituted by the alkyl group having 1 to 6 carbon atoms or the aryl group having 6 to 20 carbon atoms; the following Chemical Formula 2-1, or the following Chemical Formula 2-2,

[Chemical Formula 2-1]

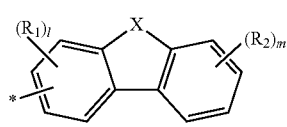

[Chemical Formula 2-2]

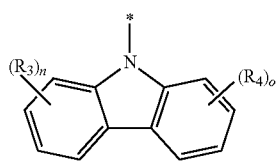

the Het$_1$ and the Het$_2$ each independently represent the following Chemical Formula 3 or the following Chemical Formula 4,

[Chemical Formula 3]

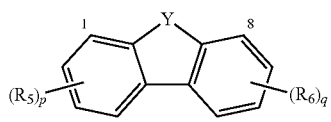

[Chemical Formula 4]

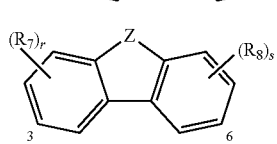

wherein, the X represents the O, the S, or the Si(R$_9$)(R$_{10}$), the Y represents the S or the O,
the Z represents the S,
the R$_1$, the R$_2$, the R$_3$, the R$_4$, the R$_5$, the R$_6$, the R$_7$, the R$_8$, the R$_9$, and the R$_{10}$ each independently represent the alkyl group having 1 to 6 carbon atoms or the aryl group having 6 to 20 carbon atoms, and the m, the n, the l, the o, the p, and the q each independently represent 0 or 1.

4. The compound of claim 1, wherein
the L$_a$ and the L$_b$ each independently represent the single bond or phenylene,
the Ar$_1$ and the Ar$_2$ each independently represent the phenyl group unsubstituted or substituted by the methyl group or the phenyl group; the naphthyl group; or the following Chemical Formula 2-1,

[Chemical Formula 2-1]

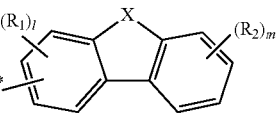

the Het$_1$ and the Het$_2$ each independently represent the following Chemical Formula 3 or the following Chemical Formula 4,

[Chemical Formula 3]

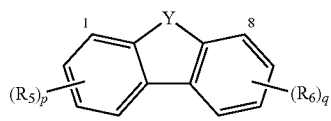

[Chemical Formula 4]

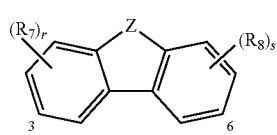

wherein, the X represents the O, the S, or the Si(R$_9$)(R$_{10}$), the Y represents the S or the O, the Z represents the S, the R$_5$ and the R$_7$ each independently represent the methyl group or the phenyl group, the R$_9$ and the R$_{10}$ each independently represent the methyl group, the p and the r each independently represent 0 or 1, and the l, the m, the q, and the s each independently represent 0.

5. The compound of claim 1, wherein the compound of the Chemical Formula 1 is represented by the following Chemical Formula 5:

[Chemical Formula 5]

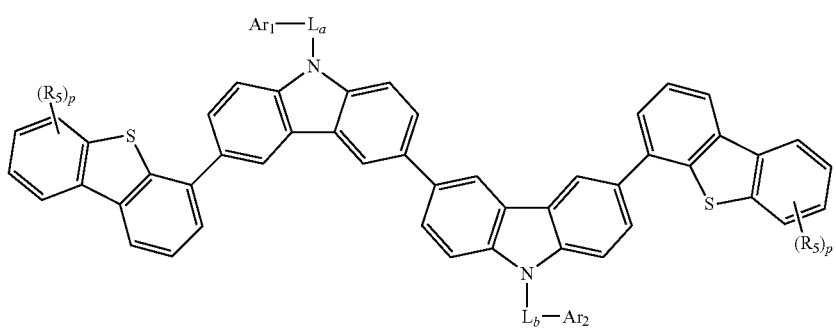

in the Chemical Formula 5,
the Ar$_1$, the Ar$_2$, the L$_a$, the L$_b$, the R$_5$, and the p are the same as those defined in claim 1,
the Ar$_1$ and the Ar$_2$ are the same as each other, and the L$_a$ and the L$_b$ are the same as each other.

6. The compound of claim 1, wherein the compound of the Chemical Formula 1 is represented by the following Chemical Formula 6:

[Chemical Formula 6]

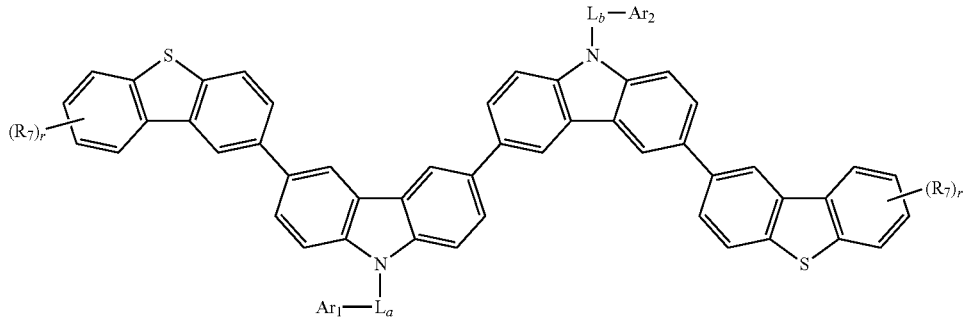

in the Chemical Formula 6,
the $Ar_1$, the $Ar_2$, the $L_a$, the $L_b$, the $R_7$, and the r are the same as those defined in claim 1,
the $Ar_1$ and the $Ar_2$ are the same as each other, and the $L_a$ and the $L_b$ are the same as each other.

7. The compound of claim 1, wherein the compound of the Chemical Formula 1 is represented by the following Chemical Formula 7:

[Chemical Formula 7]

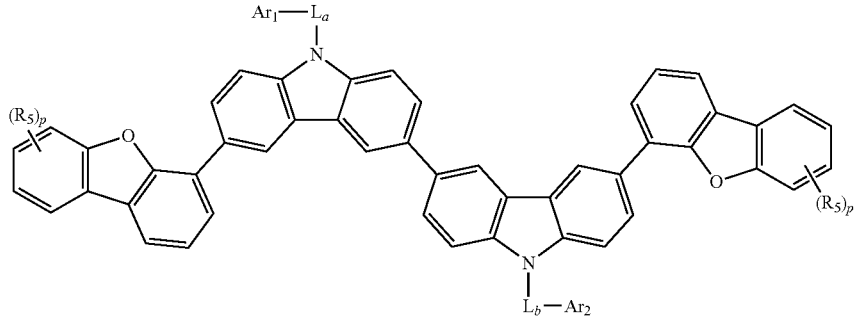

in the Chemical Formula 7,
the $Ar_1$, the $Ar_2$, the $L_a$, the $L_b$, the $R_5$, and p are the same as those defined in claim 1,
the $Ar_1$ and the $Ar_2$ are the same as each other, and the $L_a$ and the $L_b$ are the same as each other.

8. A light emitting diode comprising:
a first electrode;
a second electrode;
a light emitting layer disposed between the first electrode and the second electrode; and
a hole transportable layer disposed between the first electrode and the light emitting layer and including the compound according to claim 1.

9. The light emitting diode of claim 8, wherein the hole transportable layer further includes a P-type dopant.

10. The light emitting diode of claim 8, wherein the hole transportable layer includes: a first layer including the compound and a P-type dopant; and a second layer including the compound.

11. An electronic apparatus comprising: the light emitting diode according to claim 8.

12. The electronic apparatus of claim 11, wherein the electronic apparatus is a display device or a lighting device.

* * * * *